US012571805B2

(12) United States Patent
Witztum et al.

(10) Patent No.: US 12,571,805 B2
(45) Date of Patent: Mar. 10, 2026

(54) METHODS AND COMPOSITIONS FOR DETERMINING OxPL-ASSOCIATED DISEASES AND DISORDERS

(71) Applicant: The Regents of the University of California, Oakland, CA (US)

(72) Inventors: Joseph L. Witztum, San Diego, CA (US); Sotirios Tsimikas, Rancho Santa Fe, CA (US); Xiaoli Sun, San Antonio, TX (US)

(73) Assignee: The Regents of the University of California, Oakland, CA (US)

( * ) Notice: Subject to any disclaimer, the term of this patent is extended or adjusted under 35 U.S.C. 154(b) by 969 days.

(21) Appl. No.: 17/776,560

(22) PCT Filed: Nov. 14, 2020

(86) PCT No.: PCT/US2020/060627
§ 371 (c)(1),
(2) Date: May 12, 2022

(87) PCT Pub. No.: WO2021/097379
PCT Pub. Date: May 20, 2021

(65) Prior Publication Data
US 2022/0404378 A1 Dec. 22, 2022

Related U.S. Application Data

(60) Provisional application No. 62/935,550, filed on Nov. 14, 2019.

(51) Int. Cl.
*G01N 33/92* (2006.01)

(52) U.S. Cl.
CPC ................................... *G01N 33/92* (2013.01)

(58) Field of Classification Search
None
See application file for complete search history.

(56) References Cited

U.S. PATENT DOCUMENTS

2006/0177435 A1* 8/2006 Tsimikas ............ G01N 33/5308
435/7.1
2007/0122419 A1* 5/2007 Witztum .............. A61K 31/661
424/185.1

2009/0317819 A1* 12/2009 Tsimikas ................ G01N 33/92
435/6.14
2012/0264146 A1 10/2012 Mallat et al.
2019/0225709 A1 7/2019 Tsimikas et al.

FOREIGN PATENT DOCUMENTS

| JP | 2012-504406 A | 2/2012 |
| JP | 2018-531605 A | 11/2018 |
| WO | 2011/039578 A1 | 4/2011 |
| WO | 2012/010291 A1 | 1/2012 |

OTHER PUBLICATIONS

Seet et al. Free Radical Biology & Medicine 2010 48:560-566 (Year: 2010).*
Surma et al. Lipids in Heath and Disease 2021 20:141 (Year: 2021).*
Srivastava et al. Magnetic Resonance Imaging 2017 38:163-173 (Year: 2017).*
Giry, Murielle, European Search Report, Application No. 20887376. 0, European Patent Office, Nov. 6, 2023.
Kura, Y. et al., "Localization of oxidized phosphatidycholine in nonalcoholic fatty liver disease: Impact on disease progression", Hepatology, vol. 43, No. 3, Feb. 22, 2006, pp. 506-414.
Que, X. et al., "Oxidized phospholipids are proinflammatory and proatherogenic in hypercholesterolaemic mice", Nature, vol. 558, No. 7709, Jun. 14, 2018, pp. 301-306.
Sun, X. et al., "Neutralization of oxidized phospholipids ameliorates non-alcoholic steatohepatitis", Cell Metab., vol. 31, No. 1, Nov. 21, 2019, pp. 189-206.
Lindner, Nora, International Preliminary Report on Patentability and Written Opinion, The International Bureau of WIPO, PCT/US2020/060627, May 27, 2022.
Friedman et al., "Correlation of Antiphospholipid Antibody Recognition with the Structure of Synthetic Oxidized Phospholipids," J. of Biol. Chem., vol. 277, No. 9, pp. 7010-7020, 2001.
Young, Lee, International Search Report and Written Opinion, PCT/US2020/060627, United States Patent and Trademark Office, Mar. 1, 2021.
Kuramochi, Shunsuke, Office Action, Japan Patent Office, Application No. 2022-527051, Aug. 8, 2024.

* cited by examiner

*Primary Examiner* — Changhwa J Cheu

(74) *Attorney, Agent, or Firm* — Gavrilovich, Dodd & Lindsey LLP

(57) ABSTRACT

The disclosure provides for methods, compositions and kits that utilize total Oxidized phospholipids to determine whether a subject has liver disease.

26 Claims, 27 Drawing Sheets

Specification includes a Sequence Listing.

• Ldlr⁻/⁻

• E06-scFvLdlr⁻/⁻

Ldlr⁻/⁻     E06-scFvLdlr⁻/⁻

62.5% big T     28.6% big T

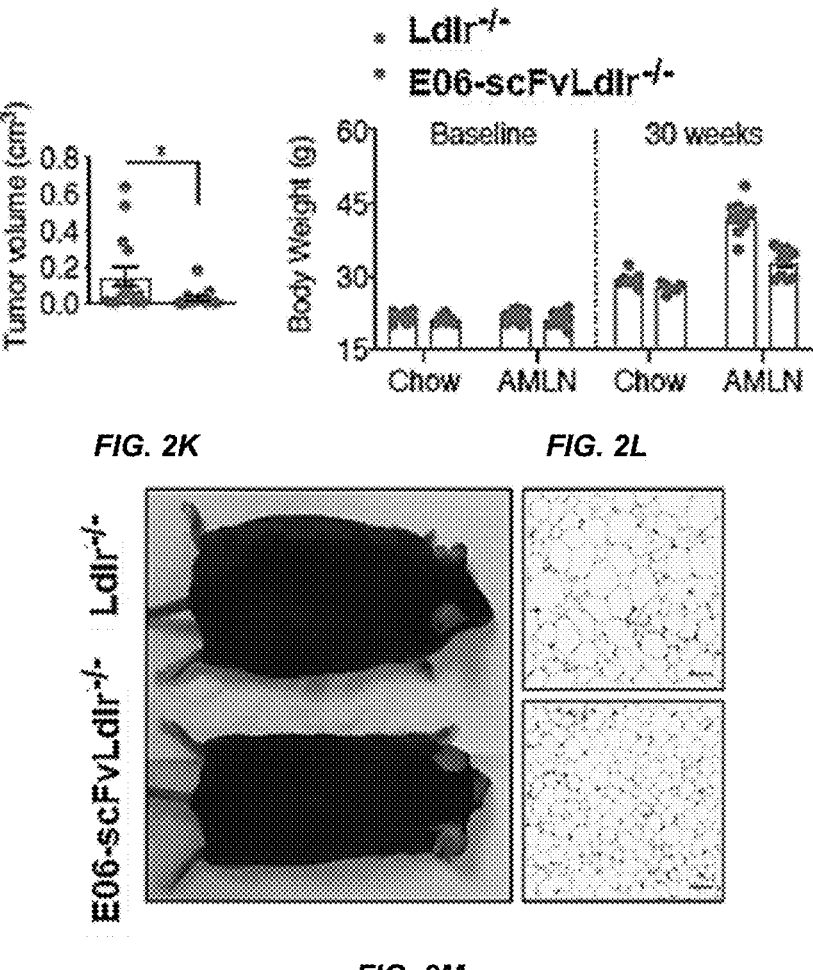
*FIG. 2K*          *FIG. 2L*
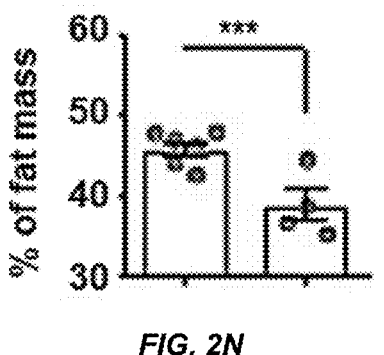
*FIG. 2M*
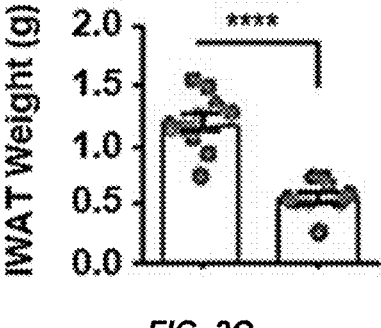
*FIG. 2N*          *FIG. 2O*

E06 induced genes (>1.5 fold, P-adj<0.05)

| Description | Log10(q) |
|---|---|
| Oxidative phosphorylation | -30.06 |
| Respiratory chain complex assembly | -28.53 |
| Monocarboxylic acid metabolism | -21.24 |
| Fatty acid metabolism | -20.87 |
| Fatty acid transport | -16.45 |
| NADH dehydrogenase complex assembly | -15.97 |
| Protein localization to mitochondrion | -13.67 |
| Cytochrome c oxidase | -7.82 |
| Cytochrome complex assembly | -7.87 |

Fatty acid transportation

Mitochondrial assembly

Oxidative phosphorylation

Expression (Z-scaled Log$_2$ (TPM+1))

● Ldlr$^{-/-}$
● E06-scFvLdlr$^{-/-}$

**

** tROS (fold)

OxPAPC

***

**

Ψm preservation (%)

OxPAPC

**

** mROS (fold)

OxPAPC

**

*

Fatty acid oxidation (fold)

OxPAPC

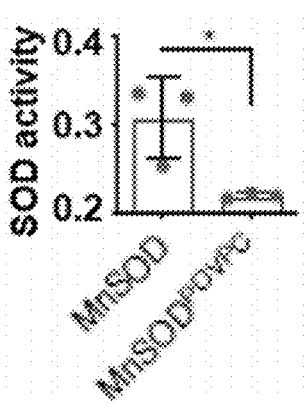
FIG. 4J
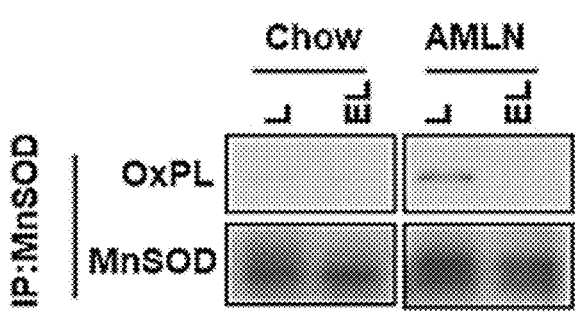
FIG. 4K
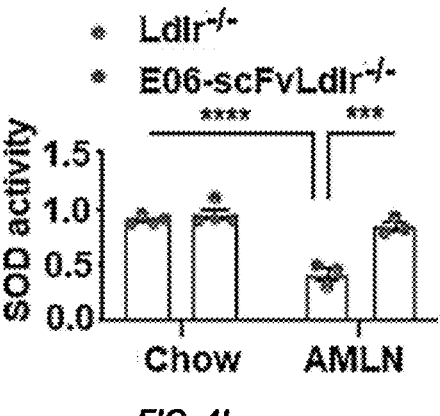
FIG. 4L
Zoom
FIG. 4N

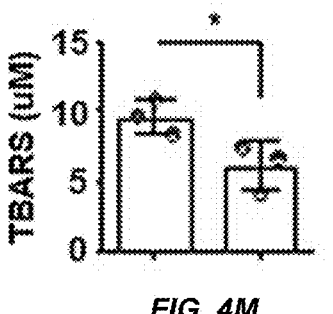
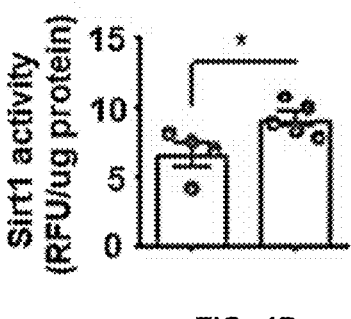
FIG. 4M    FIG. 4O    FIG. 4P
E906 upregulated mitochondrial genes
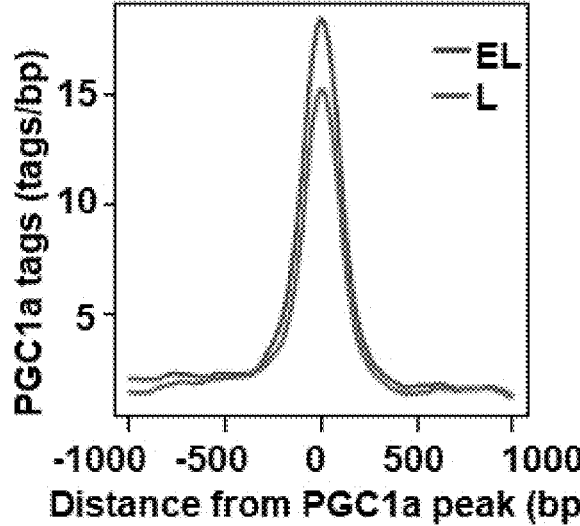
FIG. 4Q
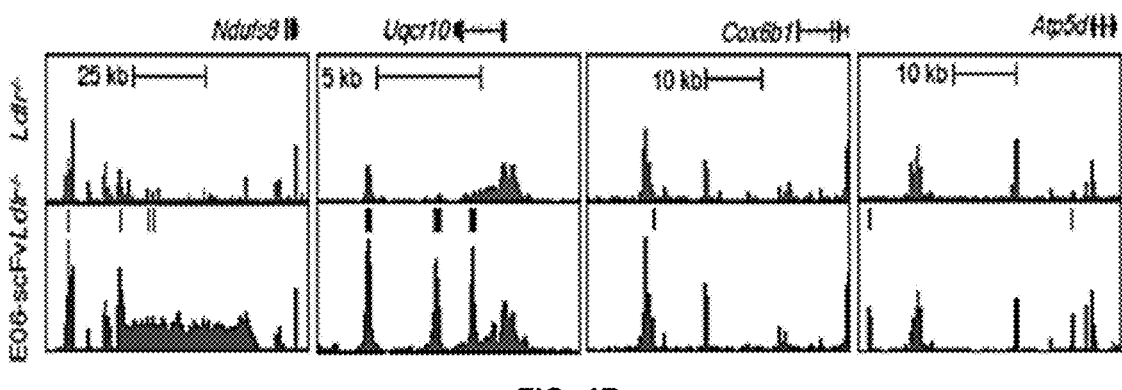
FIG. 4R

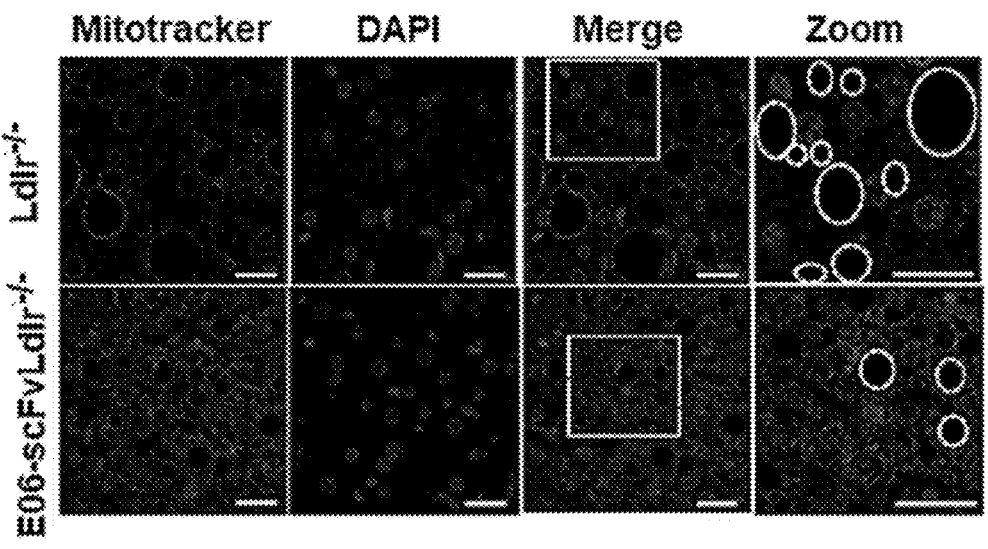
FIG. 4S
● Ldlr⁻/⁻
○ E06-scFvLdlr⁻/⁻
FIG. 4T
Recruited Macrophages
(CD45⁺F4/80⁻CD11bʰⁱLy6G⁻CD146⁻Live)
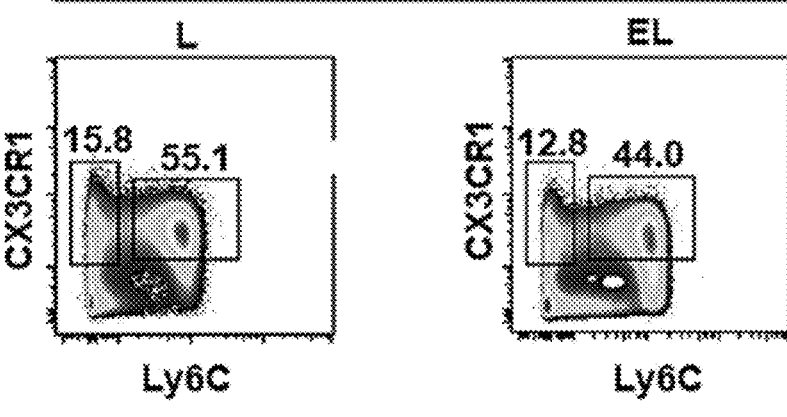
FIG.5A

Kupffer cell
(CD45⁺F4/80⁺CD11bⁱⁿᵗCD146⁻Live)

| E06 repressed genes (>1.5 fold, P-adj<0.05) | |
| --- | --- |
| Description | Log10(q) |
| Cell adhesion | -20.57 |
| Cytokine production | -19.17 |
| Leukocyte migration | -14.16 |
| Myeloid leukocyte activation | -13.55 |
| Inflammatory response | -12.13 |
| Leukocyte differentiation | -11.79 |
| Mononuclear cell proliferation | -10.02 |
| Chemotaxis | -9.61 |

E06 repressed genes (>1.5 fold, P-adj<0.05)

| Description | Log10(q) |
| --- | --- |
| Cell migration | -23.47 |
| Supramolecular fiber organization | -15.79 |
| Integrin cell surface interactions | -13.91 |
| Degradation of the ECM | -11.13 |
| Extracellular matrix organization | -10.54 |
| Collagen formation | -9.62 |
| Signaling by PDGF | -9.36 |

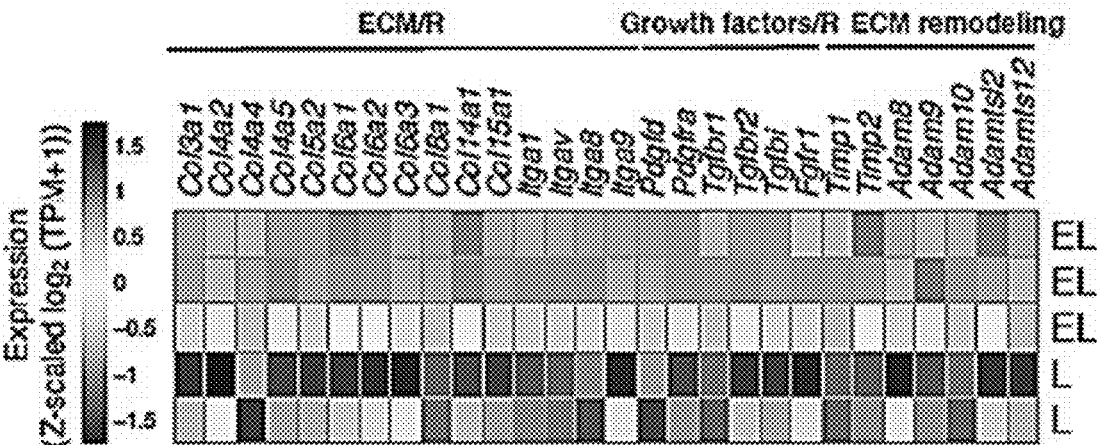
FIG. 6C
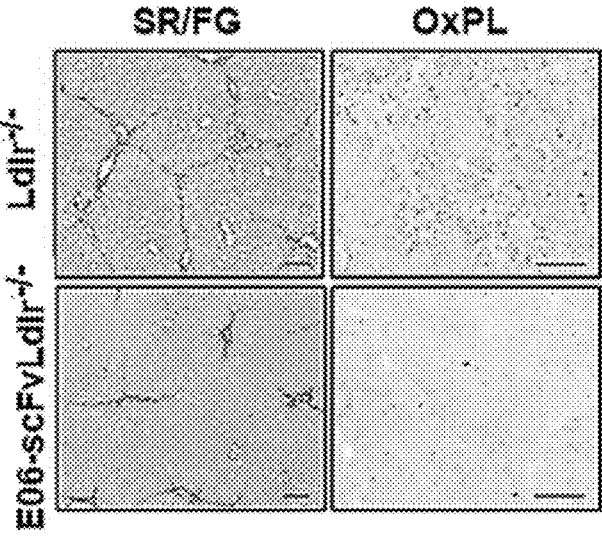
FIG. 6D
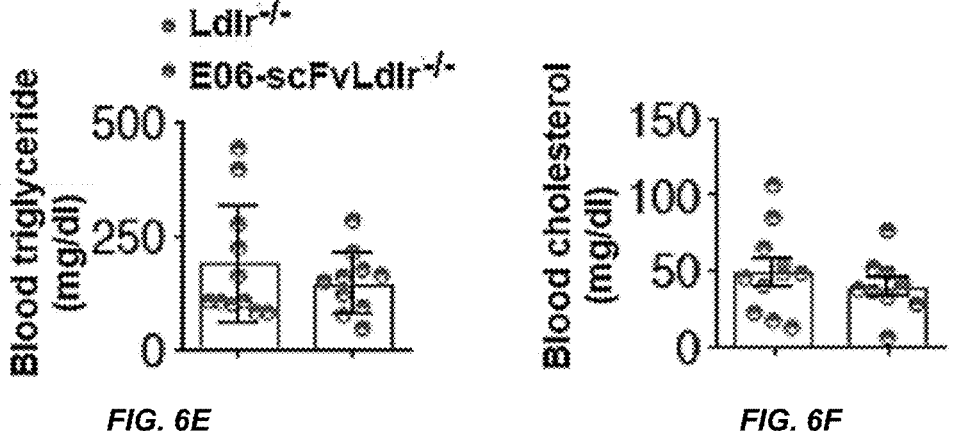
FIG. 6E                                    FIG. 6F

AMLN-NASH model

AMLN-HCC model

Age 8weeks                    NASH          Age 8 weeks                    HCC
                             38 weeks                                    56 weeks AMLN diet AMLN diet

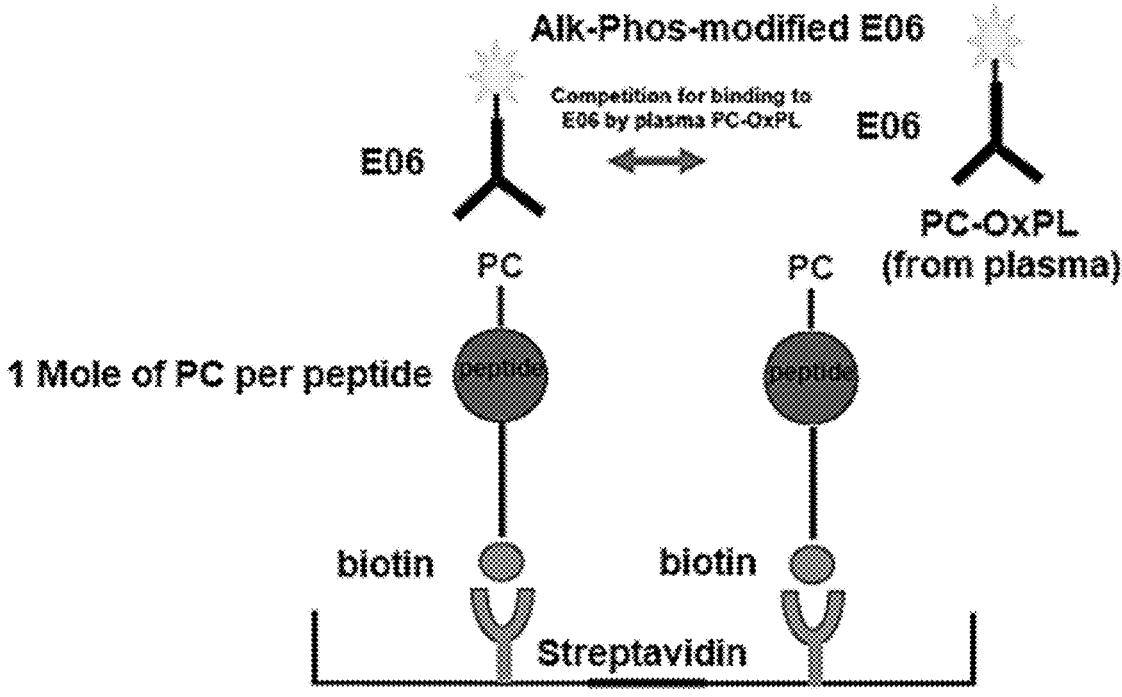

FIG. 11C

Total OxPL (mean +/- SEM)

p<0.00001 ANOVA

Baseline   6 mo post weight   12 mo post weight
                loss sugery          loss surgery

OxPL-apoB (mean +/- SEM)

p=0.048 ANOVA

Baseline   6 mo post weight   12 mo post weight
                loss sugery          loss surgery

OxPL-PLG (mean +/- SEM)

p=0.007 ANOVA

Baseline   6 mo post weight   12 mo post weight
                loss sugery          loss surgery

PLG (mean +/- SEM)

p=0.012 ANOVA

Baseline   6 mo post weight   12 mo post weight
                loss sugery          loss surgery

FIG. 12

SEQUENCE LISTING

```
<160> NUMBER OF SEQ ID NOS: 9

<210> SEQ ID NO 1
<211> LENGTH: 23
<212> TYPE: DNA
<213> ORGANISM: Artificial Sequence
<220> FEATURE:
<223> OTHER INFORMATION: D-Loop Forward Primer

<400> SEQUENCE: 1
aatctaccat cctccgtgaa acc                                          23

<210> SEQ ID NO 2
<211> LENGTH: 25
<212> TYPE: DNA
<213> ORGANISM: Artificial Sequence
<220> FEATURE:
<223> OTHER INFORMATION: D-Loop Reverse Primer

<400> SEQUENCE: 2
tcagtttagc tacccccaag tttaa                                        25

<210> SEQ ID NO 3
<211> LENGTH: 25
<212> TYPE: DNA
<213> ORGANISM: Artificial Sequence
<220> FEATURE:
<223> OTHER INFORMATION: Tert Forward Primer

<400> SEQUENCE: 3
ctagctcatg tgtcaagacc ctctt                                        25

<210> SEQ ID NO 4
<211> LENGTH: 20
<212> TYPE: DNA
<213> ORGANISM: Artificial Sequence
<220> FEATURE:
<223> OTHER INFORMATION: Tert Reverse Primer

<400> SEQUENCE: 4
gccagcacgt ttctctcgtt                                              20

<210> SEQ ID NO 5
<211> LENGTH: 20
<212> TYPE: DNA
<213> ORGANISM: Artificial Sequence
<220> FEATURE:
<223> OTHER INFORMATION: B2m Forward Primer

<400> SEQUENCE: 5
atgggaagcc gaacatactg                                              20

<210> SEQ ID NO 6
```

-continued

```
<211> LENGTH: 20
<212> TYPE: DNA
<213> ORGANISM: Artificial Sequence
<220> FEATURE:
<223> OTHER INFORMATION: B2m Reverse Primer

<400> SEQUENCE: 6
cagtctcagt gggggtgaat                                              20

<210> SEQ ID NO 7
<211> LENGTH: 20
<212> TYPE: DNA
<213> ORGANISM: Artificial Sequence
<220> FEATURE:
<223> OTHER INFORMATION: Non-NUMT Forward Primer

<400> SEQUENCE: 7
ctagaaaccc cgaaaccaaa                                              20

<210> SEQ ID NO 8
<211> LENGTH: 20
<212> TYPE: DNA
<213> ORGANISM: Artificial Sequence
<220> FEATURE:
<223> OTHER INFORMATION: Non-NUMT Reverse Primer

<400> SEQUENCE: 8
ccagctatca ccaagctcgt                                              20

<210> SEQ ID NO 9
<211> LENGTH: 20
<212> TYPE: PRT
<213> ORGANISM: Artificial Sequence
<220> FEATURE:
<223> OTHER INFORMATION: Peptide Linker

<400> SEQUENCE: 9

Ala Gly Gly Gly Gly Ser Gly Gly Gly Gly Ser Gly Gly Gly Gly Ser
1               5                   10                  15

Ala Ala Ala Tyr
            20
```

METHODS AND COMPOSITIONS FOR DETERMINING OxPL-ASSOCIATED DISEASES AND DISORDERS

CROSS REFERENCE TO RELATED APPLICATIONS

This application is a U.S. National Stage Application filed under 35 U.S.C. § 371 and claims priority to PCT/US2020/060627, filed Nov. 14, 2020, which application claims priority under 35 U.S.C. § 119 from Provisional Application Ser. No. 62/935,550, filed Nov. 14, 2019, the disclosures of which are incorporated herein by reference.

TECHNICAL FIELD

The invention relates generally to the diagnosis of liver disease and including differentiating between nonalcoholic fatty liver, nonalcoholic steatohepatitis, and normal controls.

INCORPORATION BY REFERENCE OF SEQUENCE LISTING

Accompanying this filing is a Sequence Listing entitled, "Sequence-listing_ST25" created on Nov. 14, 2020 and having 2,172 bytes of data, machine formatted on IBM-PC, MS-Windows operating system. The sequence listing is incorporated herein.

BACKGROUND

Non-alcoholic fatty liver disease (NAFLD) is the most common cause of chronic liver disease in the United States. It can be broadly sub-classified into nonalcoholic fatty liver (NAFL), which is thought to have minimal risk of progression to cirrhosis, and nonalcoholic steatohepatitis (NASH), which is thought to have an increased risk of progression to cirrhosis. The current diagnostic gold standard for differentiating whether a patient with NAFLD has NAFL versus NASH is liver biopsy. However, liver biopsy is an invasive procedure, which is limited by sampling variability, cost, and may be complicated by morbidity and even death rare.

Non-alcoholic fatty liver disease represents a spectrum of disease occurring in the absence of alcohol abuse and includes non-alcoholic steatohepatitis (NASH). A satisfactory treatment for fatty liver disease, such as NAFLD and NASH, is not presently available.

Accurate, non-invasive, biomarkers for the detection of liver disease and liver disease progression, e.g., progression to NASH, are currently also not available.

SUMMARY

The disclosure provides a method for determining and or distinguishing a disease or disorder associated with oxidized phospholipids (OxPL), the method comprising a) obtaining a sample; b) spiking the sample with labeled phosphocholine (labeled-PC) to obtain a spiked sample; c) contacting the spiked sample with a substrate comprising a known quantity of antibody, antibody fragment or non-immunoglobulin binding doamins that bind to OxPL under conditions such that OxPL and labeled-PC bind to the known quantity of antibody, antibody fragment or non-immunoglobulin binding doamins; d) contacting bound labeled-PC with an agent that measures the amount of labeled-PC; e) comparing the levels of labeled-PC to a standard curve; f) identifying an amount of total OxPL in the sample based upon the standard curve, wherein the amount is indicative of a disease or disorder associated with OxPL. In one embodiment, the sample is blood, plasma or serum. In another or further embodiment, a label of the labeled-PC is selected from the group consisting of an antigenic epitope, a protein, a peptide, a fluorescent molecule, a luminescent molecule, an enzyme, and a radiolabel. In still another embodiment, the method further comprises preparing a standard curve of labeled-PC using a substrate and various known quantities of labeled-PC. In yet another embodiment or further embodiment of any of the foregoing, the antibody is E06 or a fragment thereof or an antibody or binding domain that has the binding specificity of E06. In still another or further embodiment, the disease or disorder associated with OxPL is liver disease. In yet another embodiment or further embodiment, the liver disease is NALFD and/or NASH.

The disclosure also provides a method for determining and or distinguishing a liver disease in a subject, the method comprising (a) obtaining a sample from the subject; (b) spiking the sample with labeled phosphocholine (labeled-PC) to obtain a spiked sample; (c) contacting the spiked sample with a substrate comprising a known quantity of antibody, antibody fragment or non-immunoglobulin binding doamins that bind to OxPL under conditions such that OxPL and labeled-PC bind to the known quantity of antibody, antibody fragment or non-immunoglobulin binding doamins; (d) contacting bound labeled-PC with an agent that measures the amount of labeled-PC; (e) comparing the levels of labeled-PC to a standard curve; (f) identifying an amount of total OxPL in the sample based upon the standard curve, wherein the amount is indicative of whether the subject has liver disease. In one embodiment, the sample is blood, plasma or serum. In yet another or further embodiment, a label of the labeled-PC is selected from the group consisting of an antigenic epitope, a protein, a peptide, a fluorescent molecule, a luminescent molecule, an enzyme, and a radiolabel. In yet another embodiment, the method further comprises preparing a standard curve of labeled-PC using a substrate and various known quantities of labeled-PC. In yet another embodiment or further embodiment of any of the foregoing, the antibody is E06 or a fragment thereof or an antibody or binding domain that has the binding specificity of E06. In another or further embodiment of any of the foregoing, the liver disease is NALFD and/or NASH.

DESCRIPTION OF DRAWINGS

FIG. 1A-I OxPL accumulate in liver and serum of human and mouse models of NASH. (A) Human liver sections were classified in blinded fashion by an experienced liver pathologist and stained with E06 IgM, H&E, and Sirius Red/Fast Green (SR/FG) to determine OxPL accumulation, histology and collagen fiber deposition respectively in different stages of liver disease. Normal (no steatosis, Kleiner fibrosis score 0), NAFL (steatosis, Kleiner fibrosis score 0), NASH (steatosis, Kleiner fibrosis score 1-2), cirrhosis (steatosis, Kleiner fibrosis score 4). N=3-11. (B) Quantification of liver OxPL staining in (A), plotted against Kleiner fibrosis scores. (C) Plasma OxPL levels were determined in 82 subjects previously characterized for extent of liver disease by liver biopsy. N=15-29. (D) Plasma OxPL levels were determined in 322 outpatient subjects diagnosed as Normal (no steatosis by ultrasound with normal liver ALT and AST levels), NAFL (steatosis by ultrasound with normal liver ALT and AST levels) or NASH (steatosis and both elevated ALT and AST). N=100-118. (E) Healthy mouse model: 20 weeks old Ldlr$^{-/-}$ mice on chow diet; AMLN Model: Ldlr$^{-/-}$ mice were fed AMLN diet for 30 weeks starting at 8 weeks of age; AMLN-HCC Model: Ldlr$^{-/-}$ mice were fed AMLN diet for 48 weeks starting at 8 weeks of age; STAM Model: male Ldlr$^{-/-}$ mice were subcutaneously injected with 200 μg of streptozotocin (STZ) or vehicle within 48 hours after birth and fed with HFD for 4 weeks stating at 4 weeks of age; CCl$_4$ Model: Ldlr$^{-/-}$ mice were injected intraperitoneally with CCl$_4$ (0.5 ml/kg body weight, 1:5 diluted in corn oil) or vehicle (corn oil) twice a week for 4 weeks starting at 8 weeks of age. Paraffin-embedded mouse liver sections were stained with biotinylated-E06 IgM, haemotoxylin and eosin (H&E) and Sirius Red/Fast Green (SR/FG) to determine OxPL deposition, histology and collagen fiber deposition (red-on green background) respectively. N=6. (F) OxPL in serum of healthy (littermate control on chow diet) and AMLN-NASH mice. N=17. (G) Serum OxPL in healthy (littermate control on chow diet) and AMLN-HCC mice. N=17-21. (H) Serum OxPL in healthy (littermate control injected with vehicle on chow diet) and STAM-NASH mice. N=7-17. (I) Serum OxPL in healthy (littermate control injected with vehicle) and CCl$_4$-liver fibrosis mice. N=11-17. Data are mean±SEM. , P<0.01; , P<0.0001. Scale bar=100 μm. See also FIG. 7**.

FIG. 5A-K shows neutralization of OxPL suppresses AMLN diet-induced liver and systemic inflammation. Ldlr$^{-/-}$ (L) and E06-scFvLdlr$^{-/-}$ (EL) mice were fed with AMLN diet for 30 weeks starting at 8 weeks of age. (A, B) Flow cytometry of Ly6C$^{hi}$CD45$^+$F4/80$^-$ CD11b$^{hi}$Ly6G$^-$ CD146$^-$ Live and Ly6C$^{low}$CD45$^+$-F4/80$^-$CD11b$^{hi}$Ly6G$^-$ CD146⁻Live recruited macrophages (A), and Tim4⁺CD45⁺ F4/80⁺CD11b$^{int}$-CD146⁻ Live and Tim4⁻CD45⁺F4/80⁺ CD11b$^{int}$CD146⁻ Live macrophages (B) in the liver. N=5. (C, D) Statistical analysis of (A) and (B). N=5. (E-H) Comparison of indicated blood cytokines of indicated mice. N=5-10. (I) Comparison of RNA-seq in livers of indicated mice. Mean log$_2$ (TPM+1) values (y axis) are plotted versus log$_2$ Fold Change (x axis) of the transcripts of livers between L and EL mice. Transcripts exhibiting EL<L (>1.5 fold changes, p-adj<0.05) are red. Genes highlighted in green are the 23 genes most closely related to inflammation (EL<L, >1.5 fold change, p-adj<0.05). (J) Functional annotations associated with genes expressed lower in EL mice indicated in I (red dots). (K) Relative expression values (Z-scaled log$_2$ (TPM+1)) for the 23 genes highlighted in green in (I) are illustrated, including 7 macrophage marker genes, 15 cytokine/cytokine receptor (R)/inflammatory mediators and 1 apoptosis genes. Data are mean±SEM, * P<0.05. See also FIG. 10.

FIG. 6A-I shows targeting OxPL inhibits hepatic fibrosis. (A-C) Ldlr$^{-/-}$ (L) and E06-scFvLdlr$^{-/-}$ (EL) mice were fed AMLN diet for 30 weeks starting at 8 weeks of age. (A) Comparison of RNA-seq in livers of indicated mice. Mean log$_2$ (TPM+1) values (y axis) are plotted versus log$_2$ Fold Change (x axis) of the transcripts of livers between L and EL mice. Transcripts exhibiting EL<L (>1.5 fold change, p-adj<0.05) are red. Genes highlighted in purple are the downregulated genes closely related to fibrogenesis. (B) Functional annotations associated with genes expressed lower in EL mice (>1.5 fold changes, p-adj<0.05). (C) Relative expression values (Z-scaled log$_2$ (TPM+1)) of the 28 genes highlighted in purple in (A) are illustrated, including 15 extracellular matrix/receptor (ECM/R) genes, 6 growth factor/receptor (R) genes and 7 ECM remodeling genes. (D) L and EL mice were injected with CCl$_4$ (0.5 ml/kg body weight, 1:5 diluted in corn oil) for 4 weeks starting at 8 weeks of age. Paraffin-embedded mouse liver sections were stained with Sirius Red/Fast Green (SR/FG) to determine collagen fiber deposition and E06 IgM antibody to determine OxPL deposition. N=6. (E-H) Serum triglyceride (E), cholesterol (F) and ALT (G) levels, as well as body weight loss (H) of the same groups of mice described in (D) are shown. N=8-11. (I) Proposed model for roles of OxPL in the pathophysiology of NASH. Data are mean±SEM, *, P<0.05; **, P<0.01.

FIG. 7A-D shows mouse models of NASH and liver damage. Schematic diagram of experimental design for different mouse models. (A) AMLN-NASH Model. (B) AMLN-HCC Model. (C) STAM Model. (D) CC14 Model.

Figures 3A, 3B:
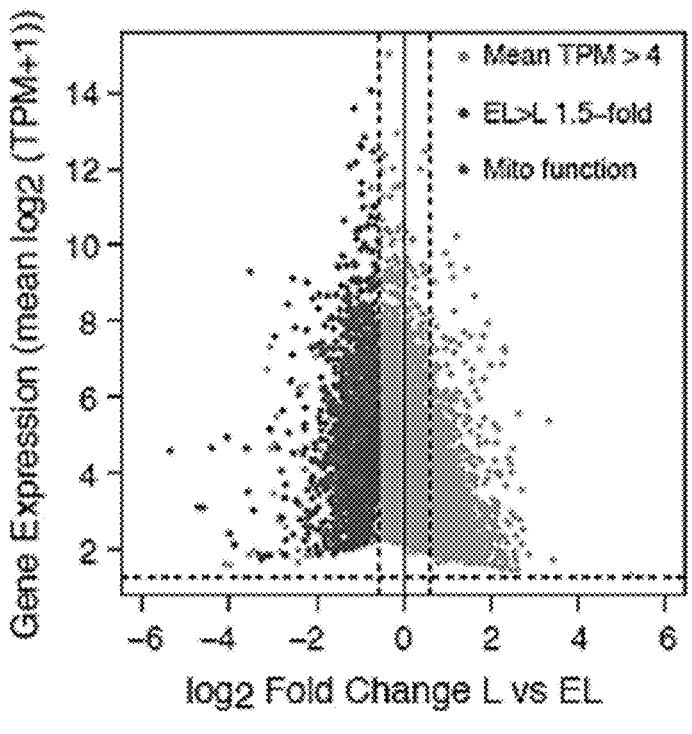
FIG. 3A-C shows neutralization of OxPL promotes mitochondrial biogenesis at the transcriptional level. (A) Comparison of RNA-seq for poly A transcripts in livers of Ldlr$^{-/-}$ (L) and E06-scFvLdlr$^{-/-}$ (EL) mice on AMLN diet for 30 weeks. Mean log$_2$ (TPM+1) values (y axis) are plotted versus log$_2$ Fold Change (x axis) of the transcripts of livers between L and EL mice (TPM, transcripts per kilobase million). All transcripts with mean TPM greater than 4 are in grey. Transcripts upregulated in EL mice (EL>L, >1.5-fold change, p-adj<0.05) are in blue. Genes highlighted in red are the 72 upregulated genes most closely related to mitochondrial functions. (B) Functional annotations associated with genes expressed more highly in EL mice (>1.5-fold change, p-adj<0.05). (C) Relative expression values (Z-scaled log$_2$ (TPM+1)) for the 72 genes highlighted in red in (A) are illustrated, including 62 oxidative phosphorylation genes, 6 mitochondrial assembly machinery genes and 4 fatty acid transportation genes.
Figures 3C, 4A, 4B, 4C, 4D:
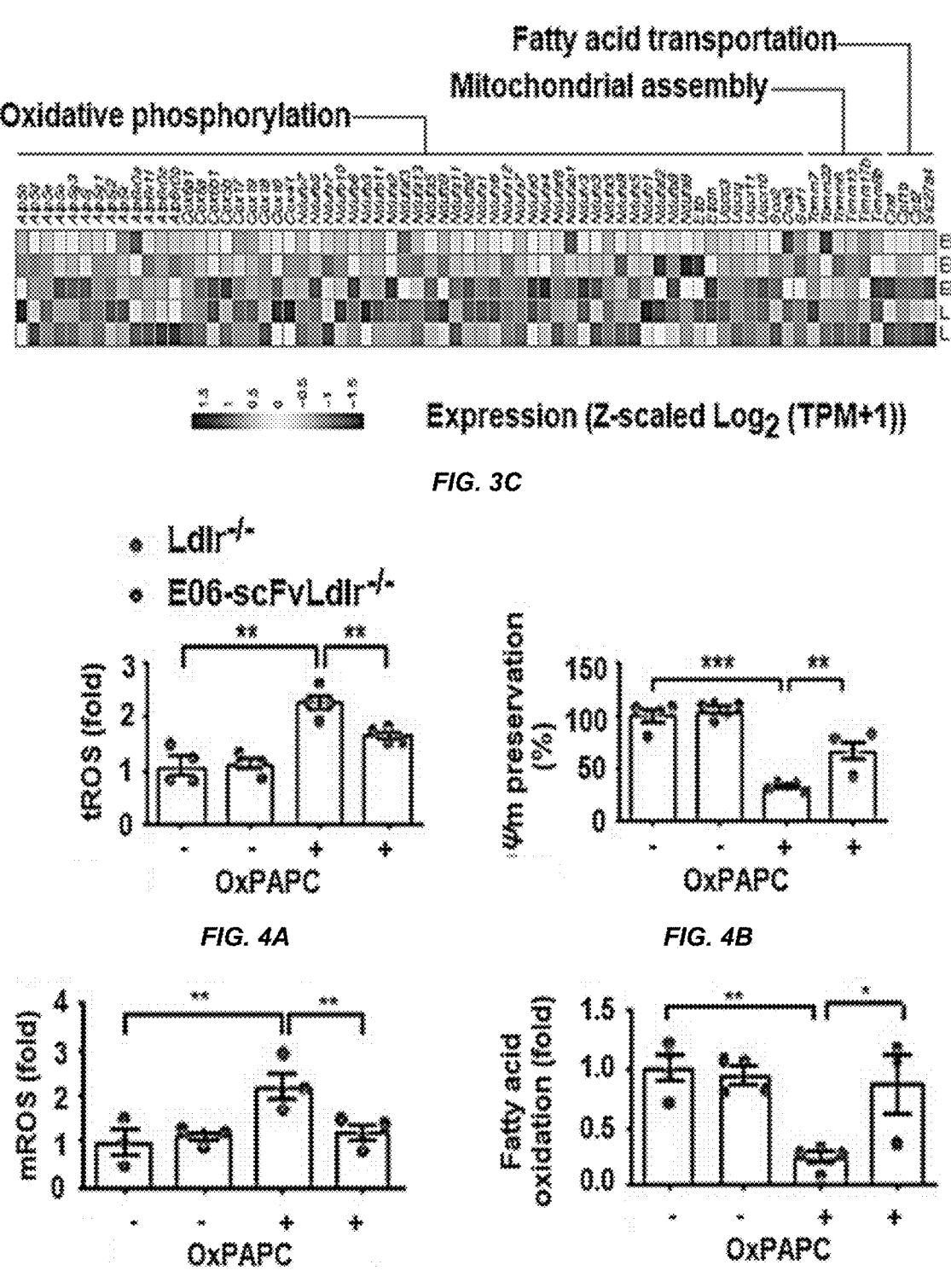
FIG. 4A-T shows neutralization of OxPL protects mitochondria. (A-D) Primary hepatocytes from Ldlr$^{-/-}$ and E06-scFvLdlr$^{-/-}$ mice were pretreated with Vehicle or OxPAPC (100 μg/mL) for 12 hours. Total ROS (A, tROS), mitochondrial membrane potential (B, Ψm preservation), mitochondrial ROS (C, mROS) and fatty acid oxidation (D) were measured. N=3-5. (E, F) Primary hepatocytes of Ldlr$^{-/-}$ mice were pretreated with Vehicle or 200 μM of MnTBAP for 1 hour, then with OxPAPC (100 μg/mL) for 4 hours. Mitochondrial membrane potential (E) and mitochondrial ROS (F) were measured. N=4-5. (G) Primary hepatocytes of Ldlr$^{-/-}$ mice treated with Vehicle, OxPAPC (20 μg/mL) or OxPAPC (1 hour pre-incubation with 50 μg/mL E06 IgM) for 1 hour were stained with E06 (green), MitoTracker (red) and DAPI (blue). Scale bar=20 μm. N=3. (H) Primary hepatocytes of Ldlr$^{-/-}$ mice were treated with Vehicle or OxPAPC (100 μg/mL) for 1 hour. MnSOD activity in the cell lysate was measured. N=3. (I) ELISA detection of E06 IgM binding to native MnSOD or POVPC modified MnSOD. N=3. (J) MnSOD activity was measured in vitro for recombinant native MnSOD and POVPC modified MnSOD. N=3. (K) Western blot with E06 of liver MnSOD isolated by immunoprecipitation from livers of chow or AMLN diet fed Ldlr$^{-/-}$ and E06-scFvLdlr$^{-/-}$ mice. (L) MnSOD activity measured in liver homogenates of chow or AMLN diet fed Ldlr$^{-/-}$ and E06-scFvLdlr$^{-/-}$ mice. N=3-4. (M) Thiobarbituric acid reactive substances (TBARS) in the plasma of 30 weeks AMLN diet fed mice. N=3. (N) Transmission electron micrographs of hepatic mitochondria of fresh liver tissue from indicated mice on AMLN diet. Asterisks indicate lipid droplets. Arrows indicates ballooned or rounded cristae (scale bar=1 μm or 0.3 μm as indicated). N=3. (O) NAD/NADH ratio in the livers of AMLN diet fed mice. N=3. (P) SIRT1 activity in the fresh liver tissue from indicated mice were measured. N=4-5. (Q) Normalized distribution of PGC1α ChIP-seq tag density, at promoters and enhancers within 3 kb of the transcription start site of E06 up-regulated mitochondrial genes (FIG. 3C) in Ldlr$^{-/-}$ (L) and E06-scFvLdlr$^{-/-}$ (EL) mice on AMLN diet. (R) UCSC genome browser images illustrating normalized tag counts for PGC1α at the indicated mitochondrial genes in same groups of mice described in (L). The tick marks indicate peaks up-regulated (>2 fold, p-adj<0.05) in E06-scFvLdlr$^{-/-}$ mice determined by DESeq2 using duplicate experiments. (S) Mitotracker staining of livers from indicated mice. Circles indicate lipid droplets. Scale bar=20 μm. (T) Fatty acid oxidation in the livers of indicated mice. N=3. Data are mean±SEM. * P<0.05;  P<0.01; *P<0.001. See also FIG. 9.
Figures 8E, 8F, 8G, 8H, 8I, 8J:
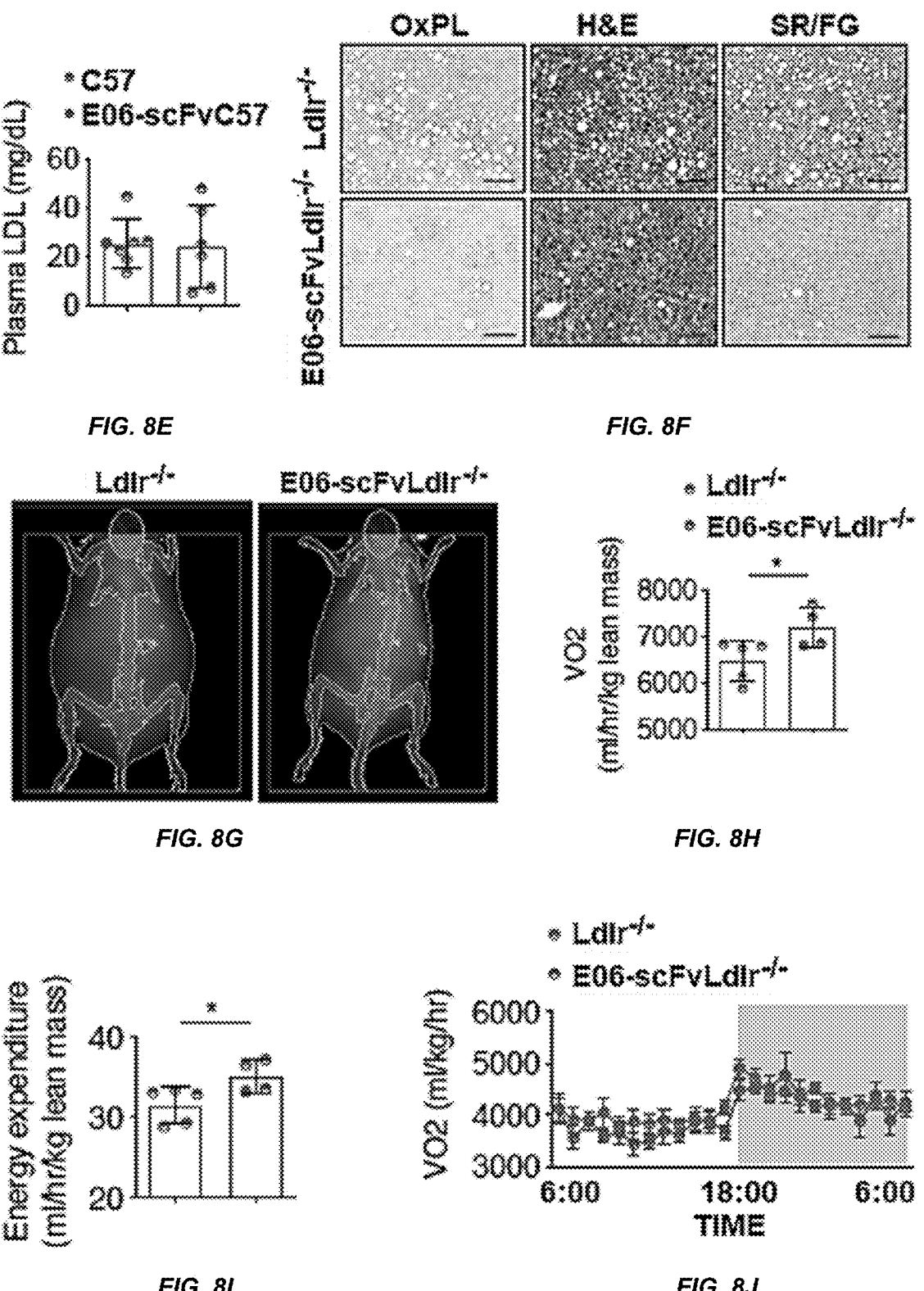
FIG. 8A-S shows neutralization of OxPL protects against hepatic fibrosis but does not affect lipid or glucose metabolism. (A, B) Serum cholesterol (A) and triglyceride (B) level of Ldlr$^{-/-}$ and E06-scFvLdlr$^{-/-}$ mice fed AMLN diet after 30 weeks. (C) Statistical analysis of liver fibrosis area (% of total area) in liver sections shown in FIG. 2A (SR/FG). (D) C57BL/6 (C57) and E06-scFv C57BL/6 (E06-scFvC57) mice were fed with AMLN diet for 30 weeks. Liver histology and fibrosis were shown. n=6-7. (E) Plasma LDL cholesterol levels of mice indicated in panel D. n=6-7. (F) Male Ldlr$^{-/-}$ and E06-scFvLdlr$^{-/-}$ mice were subcutaneously injected with 200 μg streptozotocin (STZ) within 48 hours after birth and fed with HFD for 4 weeks. OxPL accumulation, liver histology and fibrosis were shown. n=6. (G) DEXA imaging of same groups of mice in FIG. 2N. (H-I) ANCOVA analysis with lean body weight as covariant of oxygen consumption (H, VO2), and energy expenditure (I). (J) VO2 of respective mice fed on chow diet after 30 weeks. n=5. (K, L) Respiratory exchange rate (K, RER) and activity (L) of same groups of mice in FIG. 2 (RT). n=4-5. (M) Daily food intake of same groups of mice indicated in FIG. 10K-L. n=4-5. (N-Q) Serum NEFA (N), glycerol (O), fasting glucose (P), and insulin level (Q) of indicated mice. n=5-8. (R, S) Results of glucose tolerance tests (R) and insulin tolerance tests (S) in Ldlr$^{-/-}$ and E06-scFvLdlr$^{-/-}$ mice fed AMLN diet after 30 weeks. n=4-5. Data are mean±SEM. *, P<0.05. Scale bar=100 μm.
Figures 8K, 8L, 8M, 8N, 8O, 8P:
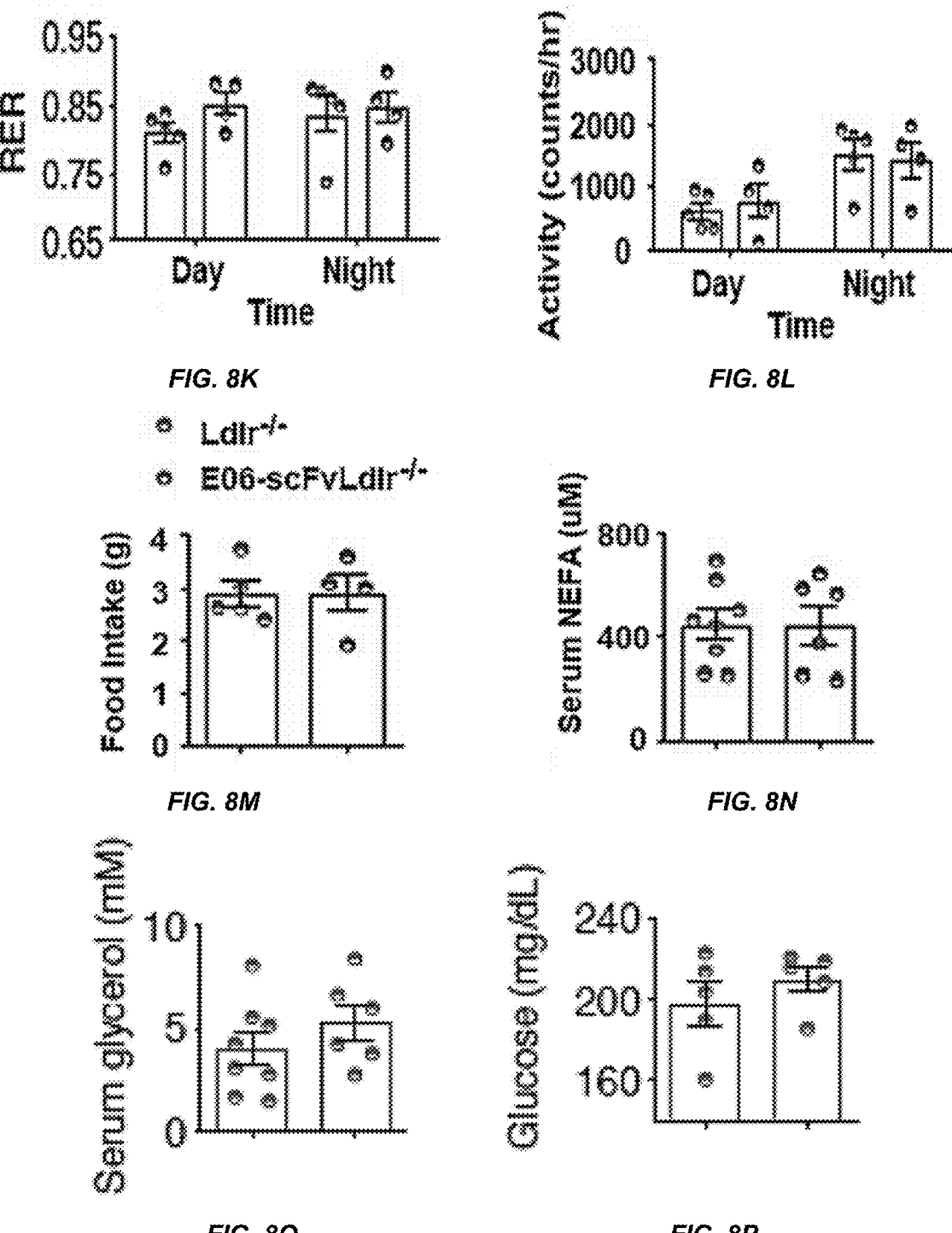
Figures 8Q, 8R, 8S, 9:
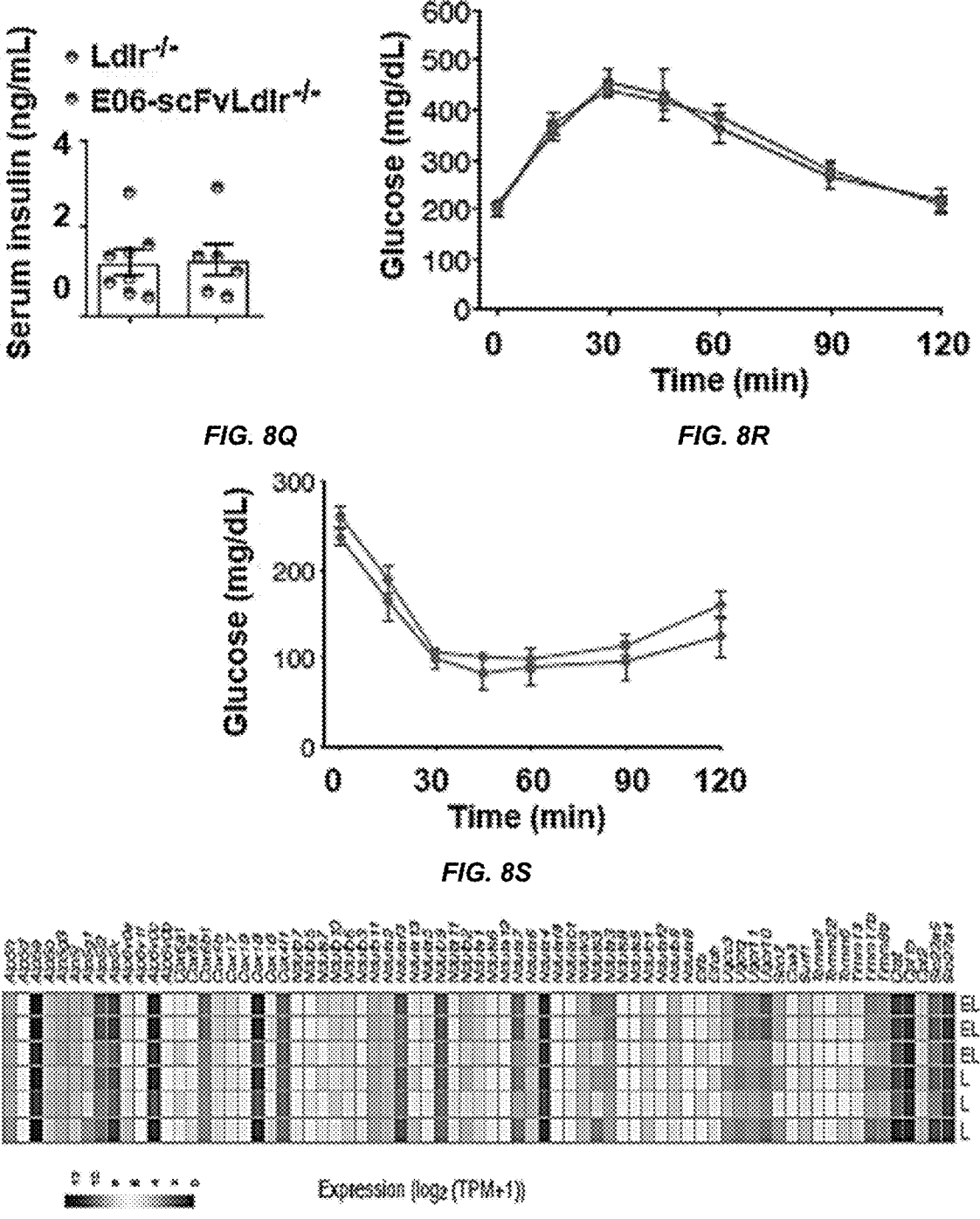

FIG. 9 shows liver RNAseq of chow diet-fed Ldlr$^{-/-}$ and E06-scFvLdlr$^{-/-}$ mice. Comparison of RNA-seq for poly A transcripts in livers of Ldlr$^{-/-}$ (L) and E06-scFvLdlr$^{-/-}$ (EL) mice on chow diet for 30 weeks. Relative expression values (log$_2$ (TPM+1)) for the mitochondrial genes shown in FIG. 3C are illustrated, including 62 oxidative phosphorylation genes, 6 mitochondrial assembly machinery genes and 4 fatty acid transportation genes.

Figures 10A, 10B, 10C, 10D, 10E, 10F:
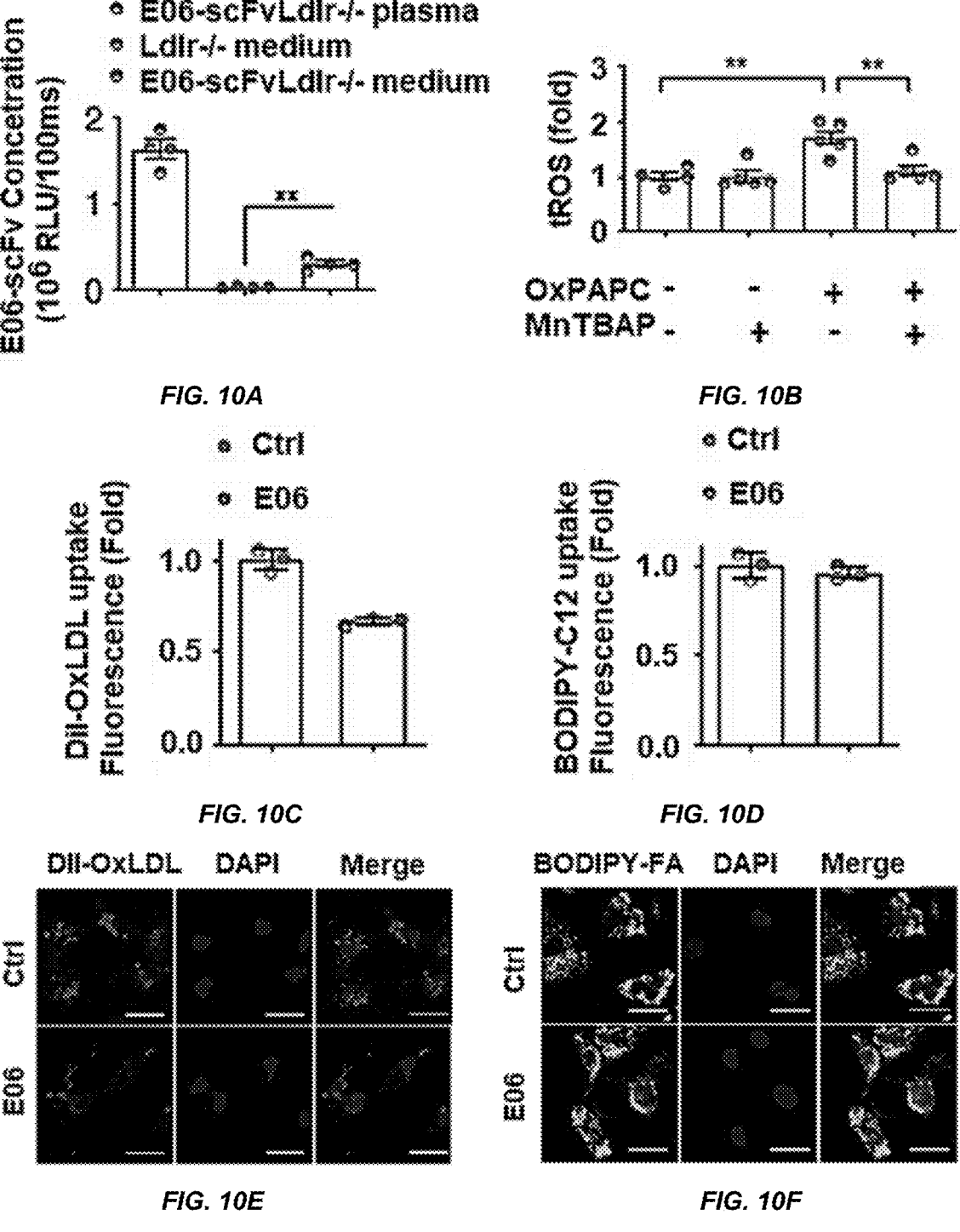
Figures 10G, 10H, 10I, 10J, 10K, 10L:
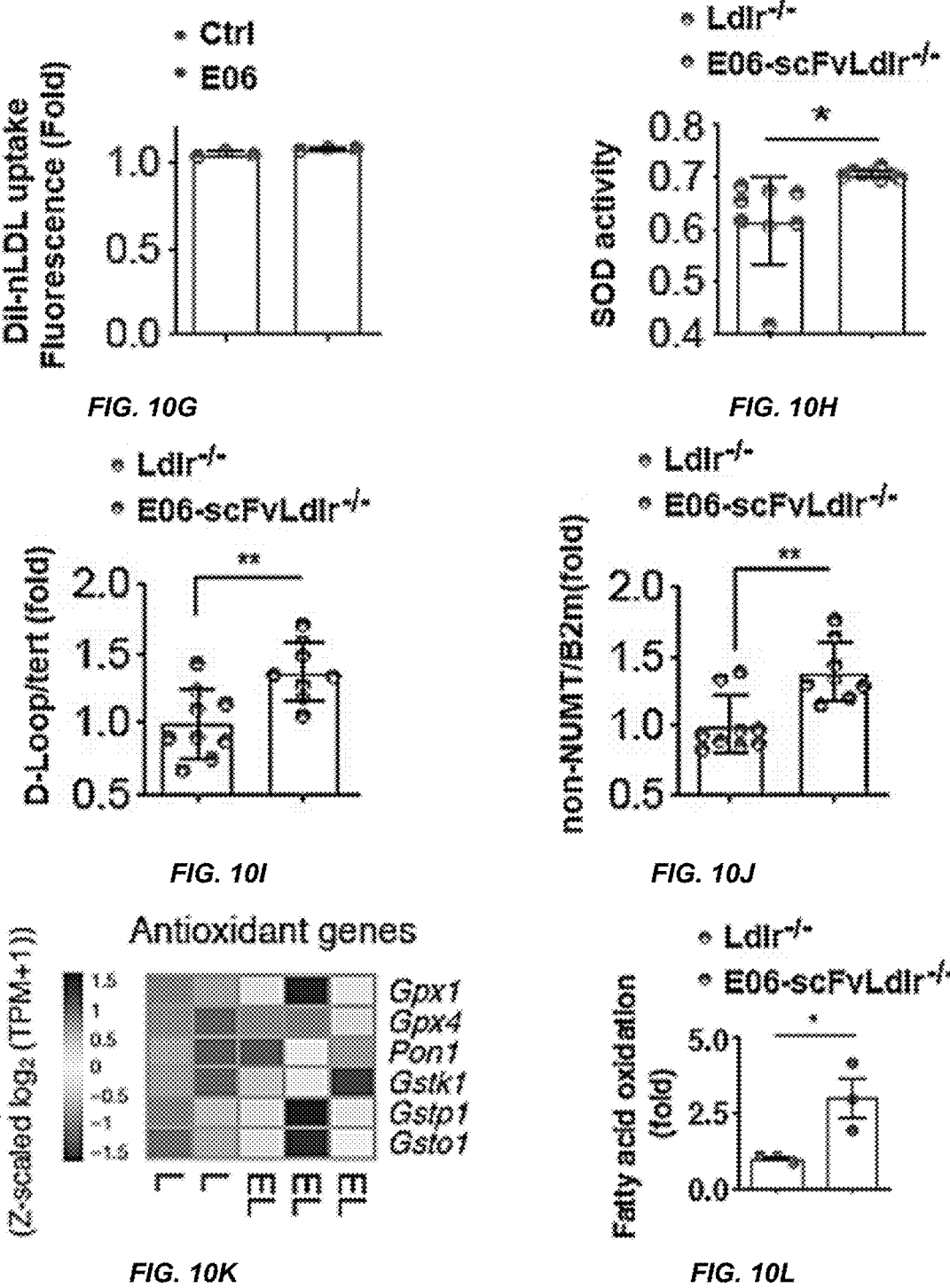
Figure 10O:
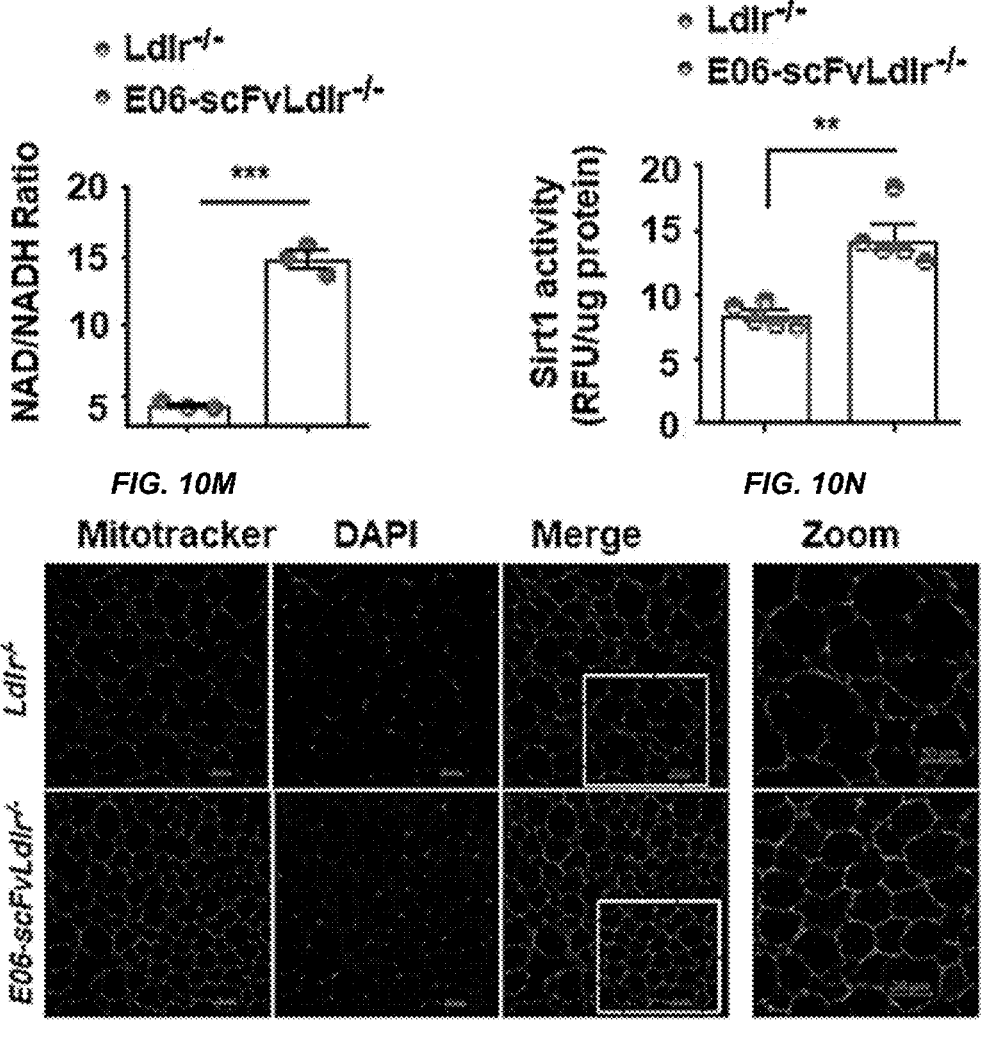

FIG. 10A-O shows neutralization of OxPL protects mitochondria in hepatocytes and adipose tissue. (A) Primary hepatocytes from 6 weeks old Ldlr$^{-/-}$ and E06-scFvLdlr$^{-/-}$ mice were cultured for 12 hours. Secreted E06-scFv in the medium and in the blood of E06-scFvLdlr$^{-/-}$ mice were measured by ELISA. (RLU/100 msec=relative light units per 100 milliseconds). n=4. (B) Primary hepatocytes of Ldlr$^{-/-}$ mice were pretreated with Vehicle or 200 μM of MnTBAP for 1 hour, then with OxPAPC (100 μg/mL) for 4 hours. Total ROS were measured. n=5. (C, D) HepG2 cells were starved for 4 hours. Dil-OxLDL (10 μg/mL) preincubated with 100 μg/mL IgM isotype control (Ctrl) or E06 IgM antibody for 1 hour were incubated with starved cells for 3 hours. Dil-OxLDL uptake was measured by Dil fluorescence (C) and confocal microscopy (D): Dil-OxLDL (red) and DAPI (blue). Scale bar=20 μm. n=3. (E, F) HepG2 cells were starved for 4 hours. BODIPY-fatty acid (FA) (1 μM in 1% BSA) preincubated with 100 μg/mL IgM isotype control (Ctrl) or E06 IgM antibody for 1 hour were incubated with starved cells for 30 min. BODIPY-FA uptake was measured by BODIPY fluorescence (E) and confocal microscopy (F): BODIPY-FA (green) and DAPI (blue). Scale barn=20 μm. n=3. (G) HepG2 cells were starved for 4 hours. Dil-Native LDL (Dil-nLDL, 10 μg/mL) preincubated with 100 μg/mL IgM isotype control (Ctrl) or E06 IgM antibody for 1 hour were incubated with starved cells for 3 hours. Dil-nLDL uptake was measured by Dil fluorescence. n=3. (H) SOD activity was measured in liver homogenates of STAM model:Ldlr$^{-/-}$ and E06-scFvLdlr$^{-/-}$ mice. n=8. (I, J) Relative total mtDNA amounts were quantified by quantitative PCR (qPCR) with primers specific for the mitochondrial D-loop region or a region of mtDNA that is not inserted into nuclear DNA (non-NUMT) and primers specific for nDNA (Tert, B2m) in liver of 30 weeks of AMLN diet-fed Ldlr$^{-/-}$ and E06-scFvLdlr$^{-/-}$ mice. n=8-9. (K) Relative expression values (Z-scaled log 2(TPM+1)) for the anti-oxidant enzymes in the liver of Ldlr$^{-/-}$(L) and E06-scFvLdlr$^{-/-}$ (EL) mice (>1.5 fold change, P-adj<0.05). (L, M) Fatty acid oxidation (L) and NAD/NADH ratio (M) in IWAT of same groups of mice in FIG. 4O were measured. n=3. (N) SIRT1 activity was measured in fresh IWAT from same groups of mice indicated in FIG. 4P. n=5. (O) Mitotracker staining of IWAT from 30 weeks AMLN diet-fed mice. Scale bar=50 μm. Data are mean±SEM. * P<0.05;  P<0.01; *P<0.001.

Figure 11A:
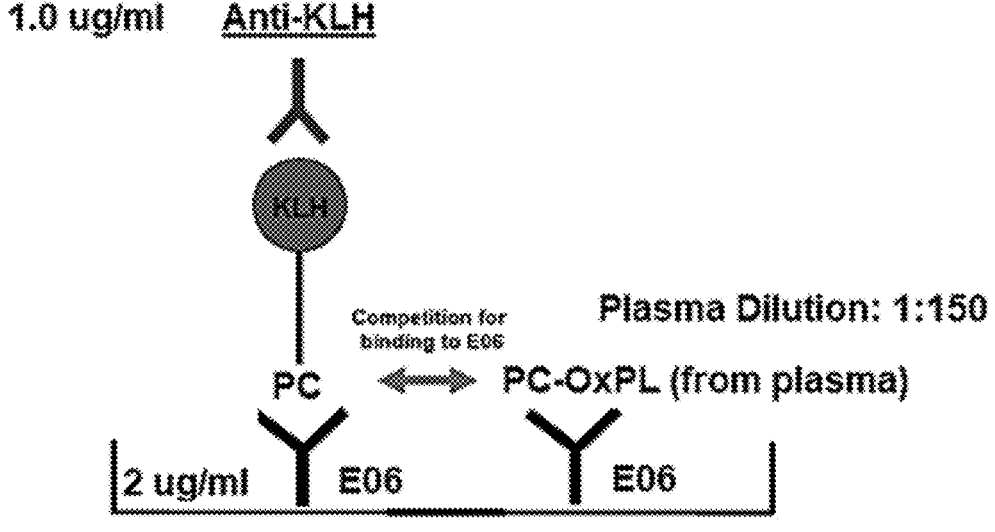
Figure 11B:
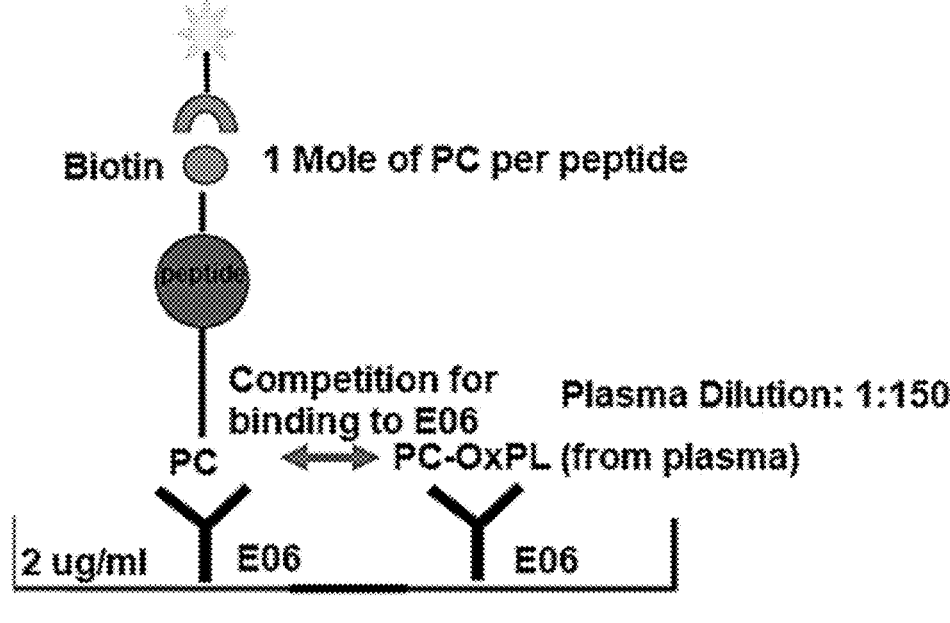

FIG. 11A-C shows various configurations of exemplary assays of the disclosure. (A) depicts and anti-OxPL antibody (EO6) plated on a substrate, and a competitive assay using PC-KLH, which is developed (read-out) by using a labelled anti-KLH antibody. (B) depicts and anti-OxPL antibody (EO6) plated on a substrate, and a competitive assay using PC-biotin, which is developed (read-out) by using a labelled streptavidin molecule. (C) depicts the binding partner of the PC-tag being plated on the substrate such that labeled OxPL antibodies compete for the PC-tagged substrate and the sample PC-OxPL.

FIG. 12 shows the effect of weight-loss resulting from bariatric surgery on OxPL in a subject.

DETAILED DESCRIPTION

As used herein and in the appended claims, the singular forms "a," "an," and "the" include plural referents unless the context clearly dictates otherwise. Thus, for example, reference to an "antibody" includes a plurality of antibodies and reference to "oxidized phospholipid" includes reference to one or more oxidized phospholipids and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The term "about" as used herein can allow for a degree of variability in a value or range, for example, within 10%, within 5%, or within 1% of a stated value or of a stated limit of a range. When a range or a list of sequential values is given, unless otherwise specified any value within the range or any value between the given sequential values is also disclosed.

The terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and may also include certain antibody fragments (e.g., single chain antibodies, scFv). An antibody can be human, humanized and/or affinity matured.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragments" comprise only a portion of an intact antibody, wherein the portion typically retains at least one, more commonly most or all, of the functions normally associated with that portion when present in an intact antibody. Examples of antibody fragments include Fab, Fab', $F(ab')_2$, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, is linked directly or indirectly to a substrate.

The term "anti-OxPL antibody" or "an antibody that binds to OxPL" or "anti-OxPL binding domain" refers to an antibody, non-immunoglobulin binding agent or other molecule that is capable of binding OxPL with sufficient affinity such that the antibody, molecule or agent can reversibly or irreversibly attach to or bind OxPL and is useful as a diagnostic and/or therapeutic agent in targeting OxPL. One exemplar anti-OxPL antibody is EO6. Other such anti-OxPL binding domains are readily identifiable or are known in the art.

The term "anti-MDA-derived-OxPL" or "anti-MAA-derived-OxPL" refers to antibodies that bind to unique epitopes on OxPL that comprise MDA or MAA epitopes, respectively.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of this disclosure.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples. The source of the biological sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments, the biological sample is obtained from a blood, fluid or liver biopsy. For example, in one embodiment, the sample is from the portal vein of the liver or from the lobular portion of the liver. The biological sample may contain compounds which are not naturally intermixed with the tissue or sample in nature such as preservatives, anticoagulants, buffers, fixatives, nutrients, antibiotics, or the like.

The term "detectably labeled phoshocholine" or "detectably labeled PC" or "PC-tagged molecule" refers to a phosphocholine molecule linked (e.g., covalently linked) to a moiety (e.g., peptide, polypeptide, antigen, fluorescent molecule, luminescent molecule, enzyme etc.) that can be detected using any number of means including antibody detection of the moiety, luminescence, fluorescence, enzyme reaction with a substrate, radioactive detection etc.). For example, a detectably labeled phosphocholine can be a phosphocholine covalently linked to a keyhole limpet hemocyanin (KLH) moiety (PC-KLH). The KLH moiety can be detected using an anti-KLH antibody. In another embodiment, the detectably labeled phophocholine can be a phosphocholine covalently linked to a biotin or streptavidin moiety and detected via binding of biotin to streptavidin. In some instances that phosphocholine is indirectly linked to the label (e.g., the label and phosphocholine are separated by a spacer moiety or linker moiety). In one embodiment, the phosphocholine is linked to a peptide which is linked at the opposite end to a label (e.g., biotin or streptavidin). The specific sequence of a peptide linker is irrelevant to the disclosure and can comprise any sequence such that the phosphocholine and label are separated from one another and can each bind or interact with the desired binding partner or substrate. For example, a PC-tagged molecule can have the general formula of Formula I:

covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the $V_H$-$V_L$ dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

A Fab fragment contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains have a free thiol group. F(ab')$_2$ antibody fragments originally were produced as pairs of Fab' fragments which have hinge cysteines between them. Other chemical couplings of antibody fragments are also known.

"Framework" or "FR" residues are those variable domain residues other than the hypervariable region residues as herein defined.

The term "hypervariable region," "HVR," or "HV," when used herein refers to the regions of an antibody variable domain which are hypervariable in sequence and/or form structurally defined loops. Generally, antibodies comprise six HVRs; three in the $V_H$ chain (H1, H2, H3), and three in the $V_L$ chain (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, Methods in Molecular Biology 248:1-25 (Lo, ed., Human Press, Totowa, N.J., 2003). Indeed, naturally occurring camelid antibodies con- Formula I Biotin-A(GGGGS)₃AAA-[Tyr]-acid ... PC The term "Fc region" as used herein refers to the C-terminal region of an immunoglobulin heavy chain, including native sequence Fc regions and variant Fc regions.

A "native sequence Fc region" comprises an amino acid sequence that is identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

"Fv" is the minimum antibody fragment, which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be sisting of a heavy chain only are functional and stable in the absence of light chain. See, e.g., Hamers-Casterman et al., Nature 363:446-448 (1993); Sheriff et al., Nature Struct. Biol. 3:733-736 (1996).

The term "interact" as used herein is meant to include detectable relationships or associations (e.g. biochemical interactions) between molecules, such as interactions between protein-protein (e.g., antibody-protein), protein-lipid (e.g., antibody-lipid), protein-nucleic acid, antibody-OxPL and the like.

An "isolated" antibody is one that has been identified and separated and/or recovered from a component of its environment (e.g., natural environment, cell culture etc.). Contaminant components of its environment are materials that would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, and typically more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. An isolated antibody includes the antibody in situ within recombinant cells since at least one component of the antibody's natural environment will not be present. Ordinarily, however, an isolated antibody will be prepared by at least one purification step.

The word "label" when used herein refers to a compound or composition which is conjugated or fused directly or indirectly to a reagent such as a nucleic acid probe or an antibody or phosphocholine etc. and facilitates detection of the reagent to which it is conjugated or fused. The label may itself be detectable (e.g., radioisotope labels, a magnetic metal (e.g., paramagnetic) or fluorescent labels) or, in the case of an enzymatic label, may catalyze chemical alteration of a substrate compound or composition which is detectable.

The "light chains" of antibodies (immunoglobulins) from any vertebrate species can be assigned to one of two clearly distinct types, called kappa ($\kappa$) and lambda ($\lambda$), based on the amino acid sequences of their constant domains.

The term "marker" refers to a biological factor (e.g., OxPL) in a sample of a subject, wherein such markers vary among individuals and can be associated with a particular disease or disease risk or disease progression. In some embodiments, the abundance, expression or presence of a marker may change during disease progression or treatment. The change in such markers are useful in diagnostics and prognostics.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier term "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to improve its production in cell culture, to create a multispecific antibody, etc., and that an antibody comprising the altered target binding sequence is also a monoclonal antibody for purposes of this disclosure. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier term "monoclonal" indicates the character of the antibody as being obtained from a substantially homogeneous population of antibodies, and is not to be construed as requiring production of the antibody by any particular method. For example, a monoclonal antibodies to be used in accordance with the disclosure may be made by a variety of techniques, including, for example, the hybridoma method (e.g., Kohler and Milstein, Nature, 256: 495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immuno-globulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

As used herein a "normal control" refers to a subject that is not obese (i.e., is at the recognized normal values for BMI for their age and height, e.g., 18 to 25 when calculated as $kg/m^2$), does not have fatty liver disease, does not have steatohepatitis, NAFLD, NASH, cirrhosis or liver disease. Thus, in the context of the disclosure a "normal control" refers to the amount of OxPL in a subject or a population of subjects that are not obese, lack liver disease, do not have steatosis, do not have cirrhosis, do not have NASH or NAFLD. These "amount of OxPL" can be expressed as RLUs, nM or mg/dL.

As used herein an "obese control" refers to a subject that does not have fatty liver disease, does not have steatohepa-titis, does not have NAFLD, does not have NASH, does not have cirrhosis or liver disease but whose body weight determined by BMI ($kg/m^2$) is 25-30, or 30 or greater, and more particularly, is above the 95 percentile for their age. Thus, in the context of the disclosure an "obese control" is refers to the amount of OxPL in a subject or a population of subject that are obese but do not have liver disease, do not have steatosis, do not have cirrhosis, do not have NASH or NAFLD.

The term "oxidized LDL" is used to describe a wide variety of LDL preparations that have been oxidatively modified including ex vivo under defined conditions, or isolated from biological sources.

"Oxidized phospholipids (OxPL)" refer to phospholipids with a phosphocholine (PC) headgroup. OxPL are highly pro-inflammatory and proatherogenic. Phosphocholine, a polar head group on certain phospholipids, has been exten-sively implicated in cardiovascular disease. Reactive oxygen species generated during coronary inflammation causes the oxidation of low density lipoprotein (LDL) to generate oxidized LDL (OxLDL). In fact, cardiovascular diseases (CVD) such as atherosclerosis, unstable angina, or acute coronary syndrome have been shown to be associated with elevated plasma levels of OxLDL (Itabe and Ueda. 2007). LDL is a circulating lipoprotein particle that contains lipids with a PC polar head group and proteins.

During oxidation of LDL, PC containing neo-epitopes that are not present on unmodified LDL are generated. Newly exposed PC on OxLDL is recognized by scavenger receptors on macrophages, such as CD36, and the resulting macrophage-engulfed oxLDL proceeds towards the formation of proinflammatory foam cells in the vessel wall. Oxidized LDL is also recognized by receptors on endothelial cell surfaces and has been reported to stimulate a range of responses including endothelial dysfunction, apoptosis, and the unfolded protein response. PC neo-epitopes are also exposed on LDL following modification with phospholipase A2 or amine reactive disease metabolites, such as aldehydes generated from the oxidation of glycated proteins. These alternately modified LDL particles are also pro-inflammatory factors in CVD.

Oxidized phospholipids (OxPL) (phospholipids with a phosphocholine (PC) headgroup) are highly pro-inflammatory and are present in a wide spectrum of inflammatory diseases, including atherosclerosis, rheumatoid arthritis, diabetic nephropathy, CNS diseases including multiple sclerosis, fatty liver diseases including non-alcoholic fatty liver disease (NAFLD) and non-alcoholic steatohepatitis (NASH), and a spectrum of acute and chronic pulmonary diseases. For example, OxPL are present in the lungs of both mice and humans infected with a wide variety of viral and bacterial pathogens. OxPL are abundant in bronchial alveolar lavage (BAL) of mice with these infections as well as in acute respiratory distress syndrome following acid installation, or in BAL of mice with COPD secondary to smoking. OxPL are proinflammatory mediators for macrophages, by inducing IL-6 for example, or alternatively inhibit the capacity of macrophages to phagocytize bacteria. OxPL are prevalent in livers of patients and mice with NASH, and have been shown to be involved in the pathogenesis in murine models of NASH. OxPL are also extensively present in atherosclerotic lesions, and in vulnerable plaques of human coronary arteries. They are also released into the circulation during interventional procedures such as PCI and stenting, where they likely mediate downstream proinflammatory and vasoactive effects.

Antibodies towards phosphocholine (PC) have been shown to bind oxidized, or otherwise modified, LDL and block the pro-inflammatory activity of OxLDL in in vivo models or in vitro studies (Shaw et al. 2000; Shaw et al. 2001).

In the context of the disclosure, "population" refers to any selected group of individuals, such as individuals that live in a particular geographic region, country or state; age-related groups; sex-related groups; weight-related groups; risk factor groups, disease related groups etc. In some cases, the population is a group of subjects, such as a group of subjects that participated in a clinical study. In another embodiment, a population can comprise an ethnic group, an age group or can be based on sex.

The term "propensity to disease," also "predisposition" or "susceptibility" to disease or any similar phrase, means that certain markers are associated with or predictive of a subject's incidence of developing a particular disease (e.g., a liver disease, NAFLD, NASH etc.). The biomarker (e.g., the presence of a particular ratio or level of phospholipid or apoprotein) are thus over-represented or underexpressed (depending upon the marker) in frequency in individuals with disease as compared to healthy individuals.

A "risk factor" is a factor identified to be associated with an increased risk of a disease or disorder. For example, an increase in the presence of OxPL compared to a control or as changed in the same subject over time, is indicative or a risk of NAFLD and/or NASH.

As used herein a "steatosis control" refers to a subject that may or may not be obese, but has been diagnosed with steatosis of the liver. "Steatosis" demonstrates elevated OxPL. Thus, in the context of the disclosure a "steatosis control" refers to the amount of OxPL in a subject or a population of subject that have been clinically diagnosed with steatosis.

As used herein a "steatohepatitis control" refers to a subject that may or may not be obese (although typically obese), but has been diagnosed with steatosishepatitis of the liver. Non-alcholic steatohepatitis demonstrates elevated OxPL. Thus, in the context of the disclosure a "steatohepatitis control" refers to the amount of OxPL in a subject or a population of subject that have been clinically diagnosed with steatohepatitis.

An "individual," "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

The term "substantially" as used herein refers to a majority of, or mostly, as in at least about 51%, 60%, 70%, 80%, 90%, 95%, 96%, 97%, 98%, 99%, 99.5%, 99.9%, 99.99%, or at least about 99.999% or more.

The term "substantially similar" or "substantially the same," as used herein, denotes a sufficiently high degree of similarity between two numeric values, such that one of skill in the art would consider the difference between the two values to be of little or no biological and/or statistical significance within the context of the biological characteristic measured by the values. The difference between said two values is, for example, less than about 50%, less than about 40%, less than about 30%, less than about 20%, less than about 10%, less than about 5%, less than about 2% and/or less than about 1%.

The phrase "substantially reduced," "substantially increased," or "substantially different," as used herein, denotes a sufficiently high degree of difference between two numeric values such that one of skill in the art would consider the difference between the two values to be of statistical significance within the context of the biological characteristic measured by said values. The difference between said two values is, for example, greater than 5%, greater than about 10%, greater than about 20%, greater than about 30%, greater than about 40%, and/or greater than about 50%.

The term "treating" as used herein is intended to encompass curing as well as ameliorating at least one symptom of a disease or at least one abnormality associated with a disorder. Treating a liver disorder can take place by administering a liver disorder therapeutic. Treating a liver disorder can also take place by modifying risk factors that are related to the liver disorder.

A "treatment plan" refers to at least one intervention undertaken to modify the effect of a risk factor upon a patient. A treatment plan for a liver disorder or disease can address those risk factors that pertain to liver disorders or diseases. A treatment plan can include an intervention that focuses on changing patient behavior, such as diet modification. A treatment plan can include an intervention whereby a therapeutic agent is administered to a patient. As examples, cholesterol levels can be lowered with proper medication, and diabetes can be controlled with insulin. A treatment plan can include an intervention that is diagnostic.

Non-alcoholic fatty liver disease (NAFLD) is the most common cause of chronic liver disease in children. NAFLD includes a range of disease states from benign steatosis to non-alcoholic steatohepatitis (NASH). The disease may cause cirrhosis with the need for liver transplantation as well as other problems such as metabolic and cardiovascular disease. Although the pathogenesis of NAFLD is still unclear it is likely that insulin resistance, increased oxidative stress and lipid peroxidation play roles. Levels of intracellular glutathione, which protects against oxidative stress, are low in NAFLD. Two distinct histological forms of NASH have been described.

Type 1 NASH occurs in adults and some children and is characterized by steatosis, lobular inflammation, ballooning degeneration and perisinusoidal fibrosis. Type 2 NASH is found most commonly in children and is characterized by steatosis, portal inflammation, and portal fibrosis. Schwimmer et al. (Hepatgology, 42(3):641-649, 2005; incorporated herein by reference) described various criteria and biomarkers used to differentiate NASH Type 1 from NASH Type 2. In particular, Schwimmer et al. discloses that subjects with NASH Type 1 had higher AST, ALT and triglyceride levels compared to patients with NASH Type 2. However, the strongest factor demonstrating a difference in the two types of NASH are best found upon histological examination. As stated above, Type 1 NASH demonstrates a prevalent lobular inflammation in the liver in contrast with a prevalent portal inflammation in Type 2 NASH. Thus, the disclosure contemplates that one of the key differentiating factors that can be used in the methods disclosed herein is identifying, by histological examination, the presence of Type 1 vs. Type 2 NASH.

As mentioned non-alcoholic fatty liver disease (NAFLD) represents a spectrum of disease occurring in the absence of alcohol abuse. It is characterized by the presence of steatosis (fat in the liver) and may represent a hepatic manifestation of the metabolic syndrome (including obesity, diabetes and hypertriglyceridemia). The increased generation of free fatty acids for hepatic re-esterification and oxidation results in accumulation of intrahepatic fat and increases the liver's vulnerability to secondary insults. NAFLD is linked to insulin resistance, it causes liver disease in adults and children and may ultimately lead to cirrhosis (Skelly et al., J Hepatol 2001; 35: 195-9; Chitturi et al., Hepatology 2002; 35(2):373-9). The severity of NAFLD ranges from the relatively benign isolated predominantly macrovesicular steatosis (i.e., nonalcoholic fatty liver or NAFL) to non-alcoholic steatohepatitis (NASH) (Angulo et al., J Gastroenterol Hepatol., 17 Suppl:S186-90, 2002). NASH is characterized by the histologic presence of steatosis, cytological ballooning, scattered inflammation and pericellular fibrosis (Contos et al., Adv Anat Pathol., 9:37-51, 2002). Hepatic fibrosis resulting from NASH may progress to cirrhosis of the liver or liver failure, and in some instances may lead to hepatocellular carcinoma. Because OSEs are inflammatory their presence in liver tissue can lead to increased inflammation and contribute to the progression of liver disease including NASH.

For example, NASH subjects have evidence of increased oxidative stress in the liver, often driven by Kupfer cells and non-enzymatic pathways. In addition, NASH subject have a reduced level of IgM antibodies to OSE compared to normal control (Hendrikxx et al., BMC Med. 14:107, 2016). In addition, Bieghs et al. shows that immunization with heat-inactivated pneumococci, which induce the production of anti-OxLDL antibodies due to molecular mimicry, led to a reduction in hepatic inflammation in NASH-induced mice (Hepatol., 56(3):894-903, 2012). In addition, protection from MDA epitopes resulted in decreased hepatic inflammation in Ldlr$^{-/-}$ mice fed a western diet and treated with a murine anti-MDA antibody (LR04).

The LDL particle is exquisitely sensitive to oxidative damage due to its complex lipid-protein composition and a large number of polyunsaturated acyl chains. The mechanisms of LDL oxidation in vivo include reactions catalyzed by 12/15-lipoxygenase (12/15-LO), myeloperoxidase (MPO), nitric oxide synthases and NADPH oxidases, as well as those mediated by heme and hemoglobin (Hb). Small amounts of Hb are constantly leaking from damaged erythrocytes, particularly in the vascular regions with turbulent flow, such as arterial bifurcations and aortic curvatures, within the intima of the atrial wall and in vasa vasorum of atherosclerotic lesions. The presence of OSEs in clinically relevant human lesions provides a strong rationale to target such epitopes in plasma and in atherosclerotic plaques for clinical applications.

Oxidation of low-density lipoprotein (LDL), as well as oxidized phospholipids on apolipoprotein B-100 (OxPL-apoB), which mainly reflect oxidized phospholipids associated with lipoprotein(a), have been identified as hallmarks of high cardiovascular risk (see, e.g., WO2014/018643, the disclosure of which is incorporated herein by reference). When LDL undergoes oxidation, the byproducts of lipid peroxidation generate many pro-inflammatory chemical modifications of both the lipid and protein moieties, collectively termed oxidation-specific epitopes (OSEs). Several of these OSEs, such as oxidized phospholipids and malondialdehyde epitopes, are well defined chemically and immunologically. They represent danger-associated molecular patterns (DAMPs) and induce a pro-inflammatory response. DAMPs are recognized by the innate immune system via pattern recognition receptors, including scavenger receptors IgM natural antibodies and complement factor H (CFH), that bind, neutralize and/or facilitate their clearance. Additionally, prior work has shown that OSEs can be imaged in zebrafish, mice, and rabbit lipid/atherosclerosis models with murine or human OSE-targeted antibodies using nuclear and MRI techniques. However, the potential immunogenicity of these approaches may limit clinical application.

Innate natural antibodies (NAbs) provide the first line of host defense against common oxidation-specific epitopes (OSE) on endogenous neo-epitopes (OxLDL and apoptotic cells) and exogenous epitopes of pathogens, and maintain host homeostasis. OSEs are ubiquitous, formed in many inflammatory tissues, including atherosclerotic lesions, and are a major target of IgM NAbs. The prototypic IgM NAb EO6, which binds the phosphocholine (PC) headgroup in oxidized phospholipids (OxPL), blocks uptake of OxLDL by macrophages. However, MDA-OSEs are not recognized by EO6 and provide the ability for additional diagnostics or therapeutics with respect to those disease or disorders with more prevalent MDA-related-OSEs.

The IgM natural antibody EO6, which binds the PC headgroup of OxPL, but does not bind unoxidized PL, has been cloned. EO6 blocks the uptake of OxLDL by macrophages and inhibits proinflammatory properties of OxPL (Friedman et al., 2002; Shaw et al., 2000). To determine the role of OxPL in vivo in the context of atherosclerosis, transgenic mice have been generated in the Ldlr$^{-/-}$ background that expressed a single-chain variable fragment of EO6 (EO6-scFv) (Que et al., 2018; see also WO2014/

131034, the disclosure of which are incorporated herein by reference). WO2014/131034 provides antibody and antibody sequences that can bind OxPL with the binding specificity of EO6. Because the EO6-scFv lacks the Fc effector functions of antibodies, biological effects observed are predicted to be due solely to blocking biological effects of OxPL. The EO6-scFv was driven by the Apoe promoter and secreted from the liver and macrophages and present in plasma at a concentration of 20-30 ug/ml. EO6-scFv bound to OxLDL and OxPL epitopes and inhibited both inflammation and atherosclerosis (Que et al., 2018). Shiri-Sverdlov and colleagues reported an inverse correlation of IgM to OxPL in human patients with NASH (Hendrikx et al., 2016). However, it is unknown if OxPL might be pathogenically involved in NASH and its complications such as fibrosis and liver damage. Thus, the EO6-scFv transgenic mice were used to determine the roles of OxPL in NASH.

Malondialdehyde (MDA) is a prominent aldehyde product of lipid peroxidation, as well as of eicosanoid metabolism, which can form adducts with the lysine residues of apoB or other proteins. MDA-modified LDL has also been isolated and characterized from the plasma of patients with coronary heart disease.

Malondialdehyde-acetaldehyde (MAA) is a stable and dominant adduct that can form on various proteins and on OxLDL molecules.

The detection of early forms of oxidized LDL in the plasma has been facilitated by the development of monoclonal antibodies (mAbs) specific for the epitopes of oxidized ApoB or oxidized lipids bound to ApoB. The three well-established mAbs used for immunoassays of oxidized LDL are: (i) FOH1a/DLH3, which was generated by immunizing mice against human coronary atheroma, and which recognizes the phosphorylcholine moiety of oxidized PC, but not of normal, PC; (ii) 4E6, which was generated by immunizing mice with $Cu^{2+}$-oxidized LDL, and which recognizes the MDA-modified lysine epitopes of ApoB; and (iii) EO6, which was established from the B cell clones of nonimmunized ApoE-deficient mice, and also recognizes the phosphocholine moiety of oxidized but not normal PC.

The disclosure provides both diagnostics and therapeutics for NALFD and NASH. In both the diagnostics and therapeutics, antibody and antibody fragments that bind OxPL are used. These antibody and antibody fragment have the binding affinity of, or substantially similar to, the EO6 antibody.

An exemplary biochemical test for identifying total OxPL employs a standardized test format, such as the Enzyme Linked Immunosorbent Assay or ELISA test, although the information provided herein may apply to the development of other biochemical or diagnostic tests and is not limited to the development of an ELISA test (see, e.g., Molecular Immunology: A Textbook, edited by Atassi et al. Marcel Dekker Inc., New York and Basel 1984, for a description of ELISA tests).

In one embodiment, the disclosure provides a method of determining OxPL (e.g., total OxPL) in a biological sample (e.g., serum, plasma, blood etc.) from a subject. The method includes providing an antibody or antibody fragment or non-immunoglobulin binding molecule, that binds to OxPL, at a known concentration (e.g., 2 µg/ml), spiking a biological sample with a phosphocholine-detectably labeled composition of known concentration; contacting the antibody or antibody fragment or non-immunoglobulin binding molecule with the spiked sample, determining the amount of detectably labeled phosphocholine in the sample, determining the amount of OxPL in the sample and comparing the quantified amounts to standard curves to determine the concentration of OxPL in the biological sample. For example, the method can be considered a competition assay to measure phosphocholine on oxidized phospholipids using an antibody (e.g., EO6) in serum, plasma or cell culture. In one embodiment, the antibody to phosophocholine is plated on microtiter well and a fixed amount of PC-linker-KLH (or PC-linker-biotin) is added to microtiter wells in absence or presence of serum or plasma. In one embodiment, the PC-linker-KLH ("PC-KLH") or PC-linker-biotin ("PC-biotin") is spiked into the biological sample to be assayed. In another embodiment, the "linker" is a random peptide sequence. After washing, the amount of PC-KLH bound is determined with anti-KLH antibody linked to a signal generating moiety (e.g., luminescent, fluorescent, colorimetric etc.). In another embodiment, the PC-biotin bound is determined with streptavidin linked to a signal generating moiety (e.g., luminescent, fluorescent, colorimetric etc.). A standard curve of PC-KLH or PC-biotin is used to quantify the amount of bound PC-KLH or PC-biotin. Because this is a competition immunoassay using, e.g., the EO6, anti-OxPL antibody that binds the PC headgroup of OxPL, it will bind to OxPL in plasma when the OxPL is free and/or covalently bound to soluble proteins. If soluble oxPL is present in plasma—either free or covalently bound—it will also bind to the plated antibody (e.g., EO6), thus proportionately reducing the binding of the fixed amount of PC-KLH or PC-biotin. A standard curve of PC-KLH or PC-biotin is used to quantify the OxPL in plasma. The amount of OxPL can be quantified by the fact that as the concentration of, e.g., plasma PC-OxPL increases the signal from the competitor (e.g., PC-KLH or PC-biotin) decreases. Thus, using the "read-out" of the amount of PC-tagged competitor in the assay one can determine the amount of PC-OxPL in the plasma or other biological sample.

It will be recognized that the competition assay described above can be modified by "reversing" the plated molecule. For example, in another embodiment, an anti-KLH antibody or streptavidin can be plated on a microtiter plate. The plate is then contacted with a sample that is spiked with PC-KLH or PC-biotin. The plate is washed and developed with an antibody that binds to phosphocholine (e.g., EO6) labeled with a signal generating moiety (a detectable label). See FIG. 11A-C for exemplary variations of the described assay. Other variations will be readily apparent to one of skill in the art.

The methods of the disclosure provide the ability to measure total OxPL in serum/plasma using, e.g., an ELISA assay or ELISA competition assay. The competitive ELISA as described herein is able to measure the concentration of OxPL in mouse and human serum. In another embodiment, limiting amounts of antibody to OxPL (e.g., EO6-IgM (330001 Avanti Polar Lipids Inc.)) was coated in wells of microtiter plates and then a fixed concentration of PC-KLH (PC-1013-5, Biosearch Tech) or PC-biotin was added in the absence and presence of serum/plasma and the extent of PC-KLH or PC-biotin binding to plated antibody (e.g., EO6) determined using anti-KLH antibody or streptavidin each labeled with a detectable label, respectively. The presence of OxPL in serum/plasma will compete with PC-KLH for binding to EO6. In a specific embodiment, a limited amount of EO6-IgM antibody (2 µg/mL in PBS) was used to coat immunograde White U Bottom 96 Well Plates (Phenix Research, NC) overnight at 4° C. The plates were blocked by 1% fatty acid free BSA for 1 h at room temperature. Human or mouse serum/plasma (1:150) were incubate for 1 h at room temperature in the EO6 coated plates to allow prebinding. This was followed by PC-KLH (1 µg/mL) addition to the wells for 1 h at room temperature. After each 1 hour of incubation, the wells were washed 3 times with TBS. Alkaline phosphatase-conjugated anti-KLH antibody (source 600-405-466 Rockland Inc.) was then applied to detect bound PC-KLH using Lumi-Phos 530. Data were collected as relative light units (RLU) RLU/100 ms in a Synergy HTX Multi-Mode Reader (BioTek, VT). A standard curve of PC-KLH without serum/plasma competitor was run in parallel on each plate to allow calculation of concentration of immunodetectable OxPL in the samples. All determinations were done in triplicate.

The diagnostic methods of the disclosure allow for the immunochemical determination of the quantity of total oxidized phospholipid (OxPL) (phosphocholine containing OXPL) in plasma, serum or fluid such as cell culture. This would include any soluble OxPL as well as OxPL bound (both covalently to proteins, as well as bound non-covalently, such as to lipoproteins). The disclosure shows that using this method the measurement of OxPL is elevated by 3-4 fold in serum or plasma of murine models of NASH and in human patients with NASH.

Although certain examples described herein use PC-KLH as a standard competitor it should be recognized that other tags in place of KLH can be used. For example, any epitope tag can be used in place of KLH and an antibody specific to the epitope tag can be used to detect bound PC-tag. Moreover, other "binding pairs" such as biotin-streptavidin and the like can be used.

Prior assay methods measured OxPL on apoB-100 containing lipoproteins and that for the most part this measures OxPL on Lipoprotein (a) particles, which contain apoB-100 and are enriched in OxPL. These prior assays do not measure OxPL on non-apoB particles.

As described further herein, the disclosure demonstrates that OxPL levels can be used to identify and differentiation patients with liver disease. For example, the disclosure demonstrates that OxPL increase in a graded fashion in patients with biopsy proven histology from obese normal to steatosis and to steatohepatitis.

The diagnostic methods of the disclosure can be used to measure total OxPL levels in subject/patients with a variety measuring the amount of PC-tags in the sample and comparing the amount to a standard curve. The curve provide an indication of the total amount of OxPL. The total amount of OxPL in the sample can then be used to compare OxPL value amounts for a particular disease state (e.g., a normal control lacking any liver disease, NASH oxPL levels, NAFLD oxPL levels, improvement in obesity etc.) or may be compared to prior levels from the same subject.

In a further embodiment, one or more additional markers of liver function may be measured. In another embodiment, the one or more markers of liver function are selected from the group consisting of alanine aminotransferase (ALT), alkaline phosphatase (ALP), aspartate aminotransferase (AST), gamma-glutamyl transpeptidase (GGT), triglycerides, and lipoproteins (e.g., LDL). In a further embodiment, an ALT level of about 60-150 units/liter is indicative of fatty liver disease. In yet another or further embodiment, an ALP level of about 150-250 units/liter is indicative of fatty liver disease. In yet another of further embodiment, an AST level of about 40-100 units/liter is indicative of fatty liver disease. In still another or further embodiment, a GGT level of 50-100 units/liter is indicative of fatty liver disease. In still another of further embodiment, a triglyceride level above 150 mg/dL and/or high LDL level is indicative of fatty liver disease. In yet another or further embodiment, a resistin level of greater than 8 ng/ml is indicative of fatty liver disease. In still yet another or further embodiment, an adiponectin level decreased by at least about 20% from age and sex matched normal subjects is indicative of fatty liver disease.

In another embodiment, the disclosure provides methods of monitoring weight-loss or the progression of weight-loss associated with bariatric surgery. The method comprises measuring total OxPL in a biological sample from a subject undergoing treatment for weight-loss before and at one or more time points following the start of weight-loss treatment. Improvement in weight-loss treatment is reflected by a reduction in total OxPL. For example, Table 1 provides an exemplary measurements of OxPL in subjects undergoing bariatric surgery (see also FIG. 12).

TABLE 1

| | Bariatric surgery, N = 39 | | | | |
|---|---|---|---|---|---|
| | Baseline | 6 months | P | 12 months | P |
| Total OxPL, nmol/L | 1774 (1339-2041) | 1325 (1146-1525) | <0.001 | 1363 (1119-1653) | <0.001 |
| OxPL-plasminogen, nM | 187.2 (126.9-258.2) | 119.5 (104.3-158.9) | 0.003 | 134.4 (105.5-173.2) | 0.001 |
| Plasminogen, mg/dl | 12.5 (11.3-14.7) | 10.7 (8.5-12.7) | 0.006 | 9.2 (7.9-10.8) | <0.001 | of diseases and disorders associated with OSE and OxPL. Such diseases and disorders include, but are not limited to, cardiovascular disease, artherosclerosis, rheumatoid arthritis, lung tissue injury (e.g., caused by smoking), brain lesions, apoptosis, senescence and fatty liver disease (e.g., NASH) and obesity.

An embodiment of the disclosure is a method of determining the progression of or existence of NASH or NAFLD in a patient. The method includes measuring the amount of total OxPL in a sample from a subject comprising spiked PC-tags by bringing into contact an antibody that binds OxPL wherein the antibody binds to OxPL and PC-tags and In another embodiment, an article of manufacture is provided. The article may include packaging material containing an antibody or antibody fragment specific for OxPL, one or more standard levels of a tagged-phosphocholine standard, an antibody against the tag, and a lebel for labeling antibodies, and the like. The packaging material may include a label or package insert indicating that the article of manufacture can be used for calculating a risk level or progression of liver diseases based upon total oxPL in a sample from a subject.

The methods of the disclosure can be used with an array (i.e., "biochip" or "microarray") that includes immobilized reagents such as antibodies or fragments against OxPL that facilitate the detection of total OxPL in a biological sample.

The term "array," generally refers to a predetermined spatial arrangement of binding islands, biomolecules, or spatial arrangements of binding islands or biomolecules. Arrays according to the disclosure that include biomolecules (e.g., antibodies or antibody fragments) immobilized on a surface may also be referred to as "biomolecule arrays." Arrays according to the disclosure that comprise surfaces activated, adapted, prepared, or modified to facilitate the binding of biomolecules to the surface may also be referred to as "binding arrays." The disclosure also contemplates surfaces bearing multiple arrays, referred to as "multiple arrays" or "repeating arrays." The use of the term "array" herein may encompass biomolecule arrays, binding arrays, multiple arrays, and any combination thereof, the appropriate meaning will be apparent from context. The biological sample can include fluid or solid samples from any tissue of the body including plasma.

An array of the disclosure or a solid phase comprises a substrate. By "substrate" or "solid support" or other grammatical equivalents, herein is meant any material appropriate for the attachment of biomolecules and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, TEFLON®, etc.), polysaccharides, nylon or nitrocellulose, resins, silica or silica-based materials including silicon and modified silicon, carbon, metals, inorganic glasses, plastics, ceramics, and a variety of other polymers. In addition, as is known the art, the substrate may be coated with any number of materials, including polymers, such as dextrans, acrylamides, gelatins or agarose. Such coatings can facilitate the use of the array with a biological sample derived from serum or plasma.

A planar array of the disclosure can contain addressable locations (e.g., "pads", "addresses," or "micro-locations") of biomolecules in an array format. The size of the array will depend on the composition and end use of the array. Arrays containing from about 2 different biomolecules to many thousands can be made. In some embodiments, the compositions of the disclosure may not be in an array format; that is, for some embodiments, compositions comprising a single biomolecule may be made as well. In addition, in some arrays, multiple substrates may be used, either of different or identical compositions. Thus, for example, large planar arrays may comprise a plurality of smaller substrates. Parallel microfluidic devices comprising arrays would be useful for parallel measurements of OxPL and total OxPL content of a biological sample or for the measurement of OxPL and a separate marker for NAFLD or NASH as described herein.

In one embodiment, a substrate is labeled with a biomolecule that binds to OxPL, the sample is then contact with a sample comprising known amounts of spiked phosphocholine tagged with a detectable epitope or label under conditions that OxPL including the tagged PC in the sample are bound to the biomolecule, the bound molecules are then washed (to remove unbound material) and a second, labeled, biomolecule that binds to the tag on the PC is then contacted with the bound OxPL such that the amount of bound PC-tags in the sample can be quantified. The amount of tag is then compared to standard curve(s) to determine the competitive displacement of tagged PC by OxPL in the biological sample. The curve(s) will then provide an indication as to the amount of total OxPL in the biological sample.

As an alternative to planar arrays, bead based assays in combination with flow cytometry have been developed to perform multiparametric immunoassays. In bead based assay systems the biomolecules can be immobilized on addressable microspheres. Each biomolecule for each individual immunoassay is coupled to a distinct type of microsphere (i.e., "microbead") and the immunoassay reaction takes place on the surface of the microspheres. Dyed microspheres with discrete fluorescence intensities are loaded separately with their appropriate biomolecules. The different bead sets carrying different binding agents can be pooled as necessary to generate custom bead arrays. Bead arrays are then incubated with the sample in a single reaction vessel to perform the immunoassay. Product formation of the biomarker with their immobilized binding agent can be detected with fluorescence based reporter systems. Biomarkers can either be labeled directly by a fluorogen or detected by a second fluorescently labeled antibody.

The signal intensities derived from captured biomarkers are measured in a flow cytometer. The flow cytometer first identifies each microsphere by its individual color code. Second the amount of captured biomarkers on each individual bead is measured by the second color fluorescence specific for the bound target. This allows multiplexed quantitation of multiple targets from a single sample within the same experiment. Sensitivity, reliability and accuracy are compared to standard microtiter ELISA procedures. With bead based immunoassay systems serum components can be simultaneously quantified from biological samples. An advantage of bead-based systems is the individual coupling of the capture biomolecule to distinct microspheres.

Surfaces useful according to the disclosure may be of any desired shape (form) and size. Non-limiting examples of surfaces include chips, continuous surfaces, curved surfaces, flexible surfaces, films, plates, sheets, tubes, and the like. Surfaces have areas ranging from approximately a square micron to approximately 500 cm². The area, length, and width of surfaces according to the disclosure may be varied according to the requirements of the assay to be performed. Considerations may include, for example, ease of handling, limitations of the material(s) of which the surface is formed, requirements of detection systems, requirements of deposition systems (e.g., arrayers), and the like.

In certain embodiments, it is desirable to employ a physical means for separating groups or arrays of binding islands or immobilized biomolecules: such physical separation facilitates exposure of different groups or arrays to different solutions of interest. Therefore, in certain embodiments, arrays are situated within wells of 96, 384, 1536, or 3456 microwell plates or within chambers of a microfluidic plate/system. In such embodiments, the bottoms of the wells may serve as surfaces for the formation of arrays, or arrays may be formed on other surfaces and then placed into wells.

Depending upon the format of the assay system and/or substrates used, the detection of bound reagents can be detected using any number of methods known in the art. Examples of such techniques include immunological techniques such as competitive binding assays and sandwich assays; fluorescence detection using instruments such as confocal scanners, confocal microscopes, or CCD-based systems and techniques such as fluorescence, fluorescence polarization (FP), fluorescence resonant energy transfer (FRET), total internal reflection fluorescence (TIRF), fluorescence correlation spectroscopy (FCS); colorimetric/spectrometric techniques; surface plasmon resonance, by which changes in mass of materials adsorbed at surfaces may be measured; techniques using radioisotopes, including conventional radioisotope binding and scintillation proximity assays so (SPA); mass spectroscopy, such as matrix-assisted laser desorption/ionization mass spectroscopy (MALDI) and MALDI-time of flight (TOF) mass spectroscopy; ellipsometry, which is an optical method of measuring thickness of protein films; quartz crystal microbalance (QCM), a very sensitive method for measuring mass of materials adsorbing to surfaces; scanning probe microscopies, such as AFM and SEM; and techniques such as electrochemical, impedance, acoustic, microwave, and IR/Raman detection. See, e.g., Mere L, et al., "Miniaturized FRET assays and microfluidics: key components for ultra-high-throughput screening," Drug Discovery Today 4(8):363-369 (1999), and references cited therein; Lakowicz J R, Principles of Fluorescence Spectroscopy, 2nd Edition, Plenum Press (1999).

Arrays of the disclosure suitable for identifying liver disease, NAFLD, NASH, disease progression and/or the efficacy of a treatment may be included in kits. In another embodiment, a pre-packaged diagnostic kit for determining the presence, risk of, or progression of liver disease is provided. The kit may include an array as described above, instructions for using the array, and instructions for calculating risk based upon the level of total OxPL in a test sample when compared to standardized samples.

In other embodiments, a method for identifying progression or regression of liver disease (e.g., from NAFLD to NASH or vice-a-versa). The method includes obtaining a first sample comprising plasma from a subject; administering a therapy to the subject; obtaining a second sample from the subject following administration of the therapy; determining the level of total OxPL in the first sample and second sample and comparing the change in values to one another or to a normal control value wherein an increase in OxPL is indicative of disease progression. The information may be provided to a caregiver in various means including directly, paper print-out over, computer screen or over the internet to a remote location.

For diagnostic applications, the assay provides a molecule which can be used to detect the amount of bound PC-tag in the sample. Such molecules are referred to as a detectable moiety or detectable label. The detectable moiety can be any label which is capable of producing, either directly or indirectly, a detectable signal. For example, the detectable moiety may be a radioisotope, such as $^{3}$H, $^{14}$C, $^{32}$P, $^{35}$S, or $^{131}$I; a fluorescent or chemiluminescent compound, such as fluorescein isothiocyanate, rhodamine, or luciferin; a magnetic or paramagnetic element or compound, or an enzyme, such as alkaline phosphatase, beta-galactosidase or horseradish peroxidase. In some embodiments, therapeutic or diagnostic radioisotopes or other labels (e.g., PET or SPECT labels) can be incorporated in the agent for conjugation to antibodies as described herein. Examples of a radioisotope or other labels include, but are not limited to, $^{11}$C, $^{13}$N, $^{15}$N, $^{15}$O, $^{35}$B, $^{18}$F, $^{33}$P, $^{47}$Sc, $^{51}$Cr, $^{57}$Co, $^{58}$Co, $^{59}$Fe, $^{62}$Cu, $^{64}$Cu, $^{67}$Cu, $^{67}$Ga, $^{68}$Ga, $^{75}$Se, $^{76}$Br, $^{77}$Br, $^{86}$Y, $^{89}$Zr, $^{90}$Y, $^{94}$Tc, $^{95}$Ru, $^{97}$Ru, $^{99}$Tc, $^{103}$Ru, $^{105}$Rh, $^{105}$Ru, $^{107}$Hg, $^{109}$Pd, $^{111}$Ag, $^{111}$In, $^{113}$In, $^{121}$Te, $^{122}$Te, $^{123}$I, $^{124}$I, $^{125}$I, $^{125}$Te $^{126}$I, $^{131}$In, $^{133}$I, $^{142}$Pr, $^{143}$Pr, $^{153}$Pb, $1^{53}$Sm, $^{161}$Tb, $^{165}$Tm, $^{166}$Dy, $^{166}$H, $^{167}$Tm, $^{168}$Tm, $^{169}$Yb, $^{177}$Lu, $^{186}$Re, $^{188}$Re, $^{189}$Re, $^{197}$Pt, $^{198}$Au, $^{199}$Au, $^{201}$Tl, $^{203}$Hg, $^{211}$At, $^{212}$Bi, $^{212}$Pb, $^{213}$Bi, $^{223}$Ra, $^{224}$Ac, or $^{225}$Ac.

Any method known in the art for conjugating the antibody or fragment or binding conjugate (e.g., biotin and streptavidin) to the detectable moiety may be employed, including those methods described by Hunter, et al., Nature 144:945

(1962); David, et al., Biochemistry 13:1014 (1974); Pain, et al., J. Immunol. Meth. 40:219 (1981); and Nygren, J. Histochem. and Cytochem. 30:407 (1982).

In other embodiments, the disclosure provides databases and computerized methods of analyzing and storing data associated with treatment regimens for liver disease (e.g., NALFD, NASH etc.) and related diseases. A database generated by the methods and analyses described herein can be included in, or associated with, a computer system for determining whether a treatment is successful. The database can include a plurality of digitally encoded "reference" (or "control") profiles. Each reference profile of the plurality can have a plurality of values, each value representing a level of, for example, total OxPL in blood or serum of an individual having, or predisposed to having, a liver disease or disorder. Alternatively, a reference profile can be derived from an individual who is normal. Both types of profiles can be included in the database for consecutive or simultaneous comparison to a subject profile. The computer system can include a server containing a computer-executable code for receiving a profile and identifying from the database a matching reference profile that is diagnostically relevant to the subject profile. The identified profile can be supplied to a caregiver for diagnosis or further analysis.

Using standard programs, electronic medical records (EMR) can be accumulated to provide a database that combines, for example, index data with additional information such as the age of a patient or any other parameter useful for predicting whether or not a subject will or is responding to a treatment. Patient information can be randomly assigned a numerical identifier to maintain anonymity with testing laboratories and for security purposes. All data can be stored on a network that provides access to multiple users from various geographic locations.

Thus, the various techniques, methods, and aspects of the disclosure described herein can be implemented in part or in whole using computer-based systems and methods. Additionally, computer-based systems and methods can be used to augment or enhance the functionality described herein, increase the speed at which the functions can be performed, and provide additional features and aspects as a part of, or in addition to, those of the disclosure described herein.

Diagnostic formulations/preparations comprising components of the assays described herein (e.g., an antibody or fragment thereof or a PC-tagged molecule of the disclosure) are prepared for storage by mixing the antibody or fragment having the desired degree of purity with optional physiologically acceptable carriers, excipients or stabilizers (Remington: The Science and Practice of Pharmacy 20th edition (2000)), in the form of aqueous solutions, lyophilized or other dried formulations. Acceptable carriers, excipients, or stabilizers are nontoxic if used for purposes of administration at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants or polyethylene glycol (PEG).

The antibody and antibody fragments disclosed herein bind to OxPL. In addition, the antibodies can bind to OxPL and block their pro-inflammatory effects. Such proinflammatory effects include OxPL-associated disease and disorders including, for example, cardiovascular disease, atherosclerosis, rheumatoid arthritis, lung tissue injury (e.g., caused by smoking), brain lesions, apoptosis, senescence and fatty liver disease (e.g., NASH). The in vivo use of an antibody or antibody fragment (humanized, human and non-humanized) of the disclosure or a human, humanized and non-human antibody of the disclosure can be used to (a) block biological affects cause by OxPL, (b) treat any one or more of cardiovascular disease, atherosclerosis, rheumatoid arthritis, lung tissue injury (e.g., cause by smoking), brain lesions, apoptosis, senescence and fatty liver disease (e.g., NASH) by blocking the effects of OxPL, (c) detect and/or diagnose inflammatory disease or disorders by detecting total OxPL in a sample from or tissue in a subject.

EXAMPLES

Animals. Ldlr$^{-/-}$ (L) mice in the C57BL/6J background were purchased from Jackson laboratory. E06-scFv Ldlr$^{-/-}$ (EL) mice were generated by crossing E06-scFv (Que et al., 2018) to Ldlr$^{-/-}$ mice all on C57BL/6 background. All mice were bred and maintained at the UCSD pathogen-free animal facility and were used in accordance with the Guide for Care and Use of Laboratory Animals of the National Institute of Health. The protocols were approved by the Institutional Animal Care and Use Committee (IACUC) of UCSD. All mice were housed in a temperature-controlled environment with 12-h dark, 12-h light cycles and given free access to water and food, except for fasting period. Only male mice were used for experiments. When indicated, mice (Ldlr$^{-/-}$ or C57BL/6) were fed an AMLN diet consisting of 40 kcal % Fat/20 kcal % Fructose/2% Cholesterol from Research Diet (D09100301 Research Diets Inc) starting at 8 weeks old of age for 20-30 weeks to generate NASH model and for 48 weeks for HCC model. For experimental neoplasia assessment, which includes tumor size limits (not exceeding 2 cm for a single tumor) and monitoring parameters, tumor volumes were calculated as (width$^2$×length)/2, and for multiple liver tumors the volumes of single tumor were added for a total tumor volume (Shalapour et al., 2017). In the CCl$_4$ model, indicated mice were injected intraperitoneally with CCl$_4$ (0.5 ml/kg body weight, 1:5 diluted in corn oil) twice a week for 4 weeks, and mice were sacrificed 72 hours after the last injection. In the STAM model, male L and EL mice were subcutaneously injected with 200 µg streptozotocin (STZ) 2 days after birth and fed with high fat diet consisting of 60% of calories from fat (D12492 Research Diets Inc.) starting at 4 weeks of age for 4 weeks.

For all experiments, Ldlr$^{-/-}$ and E06-scFvLdlr$^{-/-}$, C57BL/6 and E06-scFvC57BL/6 mice were littermates and cage mates. The E06-scFv were all heterozygotes. Animals in each cohort were produced from 20 breeding pairs to minimize the birthdate range. Identification codes were assigned to each mouse and the investigators were blinded to treatment or genotype during experiments. For metabolic study, mice were subject to CLAMS indirect calorimetry and dual energy DEXA scanning at ACP phenotyping core of UCSD. Oxygen consumption rate (OCR) and energy expenditure (EE) per kilogram of body weight were determined.

Analysis of covariance (ANCOVA) (Tschop et al., 2011) was performed to test the difference of OCR and EE between groups (body weight as covariant) with IBM SPSS Statistics. EE was calculated as a function of OCR and carbon dioxide production according to the following formular: energy expenditure (kcal/hr)=(3.941xVO$_2$ (ml/hr)+1.106xVCO$_2$ (ml/hr))/1000 (Owen et al., 2014). Rectal temperature was measured by Model 4600 Thermometer (Alpha Technics). Serum insulin was measured with Ultra-Sensitive Mouse Insulin ELISA kit (Crystal Chem).

Human liver sections and plasma. Human liver samples used in the study were obtained by Dr. Kisseleva via collaboration with Lifesharing (www.lifesharing.org). Classification of liver histology was performed by an experienced liver pathologist in a double blinded manner, and categorized as normal, steatosis, and NASH induced liver fibrosis stage 1, 2, and 4. Plasma samples for measurement of OxPL were obtained from human outpatient samples and from a previously published clinical study (Gorden et al., 2015). All human samples were collected under protocols approved by the UCSD Human Research Protections Program.

Primary hepatocyte isolation: Primary hepatocytes were isolated from 6-week-old Ldlr$^{-/-}$ and E06-scFvLdlr$^{-/-}$ mice by a 2-step collagenase perfusion method. Briefly, HBSS (Life Technologies Co.; no Calcium and Magnesium, 0.5 mM EDTA, 25 mM HEPES) was used to perfuse liver at 10 mL/min speed until the liver turns into pale. Afterward, the liver was perfused with HBSS digestion buffer (Life Technologies Co.; 30 mg/100 mL collagenase I, 2 tablet/100 mL protease inhibitor) at 15 mL/min speed for 18 min. After sequential flows, cells were smashed through 100 µm strainer and washed with Williams' Medium E (Gibco, Grand Island, NY). Hepatocytes were isolated by density gradient centrifugation using percoll (Pharmacia, Sweden). Hepatocytes with 95% viability were cultured in Williams' Medium E supplemented with 5% serum, 0.5% penicillin/streptomycin and 15 mM HEPES at 37° C. in a 5% CO$_2$ incubator overnight before use in experimentation.

Non-parenchymal cells (NPC) isolation from the mouse liver: Liver NPC were processed for fluorescence activate cell sorting of Kupffer cells, with modifications from previous published methodology (Mederacke et al., 2015; Muse et al., 2018; Seki et al., 2007). In brief, liver was perfused with pre-warmed HBSS (no calcium and magnesium, 0.5 mM EGTA, 0.75 mM EDTA, 20 mM HEPES, 1 µM flavopiridol) for 3 min at a speed of 7 mL/min through inferior vena cava. This was followed by 60 ml of digestion buffer (HBSS, 0.1 mg/ml Liberase TM, 20 µg/ml DNaseI, 20 mM HEPES, 1 µM flavopiridol) at the speed of 7 ml/min for 8 min. Liver was then dissected and incubated in 50 ml conical tube containing 20 ml of digestion buffer for 20 additional minutes at 37° C. with gentle rotation using a Miltenyi MACSmix tube rotator. Cells were then smashed through 70 µm cell strainer. Hepatocytes were removed by a 2 low-speed centrifugation steps at 50 g for 2 min. Cells were then washed with wash buffer (HBSS containing 20 µg/ml DNaseI, 2% FBS, 20 mM HEPES). NPCs were separated from debris by pelleting for 15 min at 600 g by density gradient centrifugation using 20% isotonic Percoll (Pharmacia, Sweden). Cells were then washed with 28% Optiprep (Sigma Aldrich) and carefully underlaid beneath 3 mL of wash buffer. The gradient was centrifuged a 1400 g for 25 min and cells enriched at the interface were saved and subjected to isotonic erythrocyte lysis. Later, enriched NPCs were washed, suspend in PBS and then stained for indicated antibodies for flow cytometer.

Histology: Mice were euthanized by CO2 inhalation. Tissues were dissected, and then fixed in sucrose fix working solution (4% paraformaldehyde, 20 mM sodium phosphate buffer, 2 mM EDTA, 7.5% sucrose). Paraffin/OCT-embedding tissues were sectioned and subject to H&E staining in the La Jolla Atherosclerosis Morphology Core. Fast Green (Fisher Scientific)/Sirius Red (Sigma Aldrich Inc.) staining was carried out on paraffin sections to assess liver fibrosis. Oil Red O staining was conducted on frozen-sections embedded in OCT to determine hepatic steatosis. Stained tissue was visualized with NanoZoomer Slide Scanner. Signal intensity was determined by ImageJ (NIH, Maryland, USA) analysis of H&E, Oil Red O and Fast Green/Sirius Red stained tissues. As described in the text, in some studies, formal histological analyses of features of NASH in various models were blindly assessed by an experienced pathologist according to Kleiner Scoring System (Kleiner et al., 2005).

Immunostaining and TUNEL staining: Paraffin embedded tissue sections were subjected to de-paraffinization and rehydration, and then were immersed in 95° C. antigen retrieval buffer (10 mM sodium citrate, 0.05% Tween 20, pH6.0) for 30 min. Cells were fixed with 10% buffered formalin for 10 min at room temperature and permeabilized with 0.02% Triton X-100 for 5 min. Tissue sections or cells were blocked with 1% normal donkey serum for 30 min. For E06 staining, the sections or cells were blocked sequentially by donkey serum and biotin/avidin blocking. Sections were incubated with primary antibodies for 12 h at 4° C. F4/80 (AbD Serotec) and biotinylated E06 staining (Que et al., 2018) were conducted on indicated liver/adipose paraffin sections to analyze macrophage infiltration and OxPL accumulation. Mitochondria in the liver and adipose tissue were stained with 200 nM Mitotracker Red (Life Technologies) for 45 min at room temperature. Hepatic apoptosis was determined by TUNEL staining of liver sections from mice on AMLN diet with ApoBrdU DNA Fragmentation Assay Kit (K401 BioVision Inc) according to the manufacturer's instruction. Nuclei were stained with DAPI. IHC stained tissue was visualized with NanoZoomer Slide Scanner. Fluorescence stained sections were examined using Zeiss LSM 880 with FAST Airyscan (Zessi, Germany).

Hepatic hydroxyproline measurement: Liver tissue was homogenized in distilled water (100 μl/10 mg tissue). 100 82 l of 10 mol/L concentrated NaOH was added to each 100 82 l samples and hydrolyzed at 120° C. for 1 hour. Supernatants were cooled on ice and neutralized with 10 mol/L concentrated HCl, followed by 10000 g centrifugation for 5 min. The supernatants were then collected without lipid content. Hepatic hydroxyproline was measured with Hydroxyproline Assay Kit (Abcam) according to the manufacturer's instruction.

Measurement of E06-scFv titers in culture supernatants: E06-scFv titers in the culture supernatants of primary hepatocytes were determined by chemiluminescent ELISA assays. The principle of assay is that the E06-scFv has a His6 epitope tag. In brief, 96-well round-bottom MicroFluor plates (Phenix Research, NC) were coated with PC-KLH (PC-1013-5, Biosearch Tech) at 5 μg/ml (50 82 l per well) in PBS overnight at 4° C. Culture media of primary hepatocytes were collected after 12 hours of culture, centrifuge at 1000 g for 10 min and the supernatant collected for E06-scFv titer test. After the plates were washed and blocked with 1% BSA in Tris-buffered saline (TBS) for 60 min, 40 82 l of culture media were added to the wells, and incubated for 60 min at room temperature. Bound E06-scFv was detected with anti-His6-tag antibody conjugated to alkaline phosphatase (Sigma-Aldrich), in TBS buffer containing 1% BSA, followed by three rinses with TBS and the addition of 25 μl of 50% LumiPhos 530 (Lumigen) as luminescent substrate. The light emissions were measured, and counts expressed as relative light units over 100 ms (RLU/100 ms) using a Dynex Luminometer (BioTek, VT). All determinations were done in triplicate.

Measurement of Total-OxPL in serum/plasma by ELISA: A competitive ELISA was established to measure the concentration of OxPL in mouse and human serum. Limiting amounts of E06-IgM (330001 Avanti Polar Lipids Inc) was coated in wells of microtiter plates and then a fixed concentration of PC-KLH (PC-1013-5, Biosearch Tech) was added in the absence and presence of serum/plasma and the extent of PC-KLH binding to plated E06 determined using anti-KLH antibody. The presence of OxPL in serum/plasma will compete with PC-KLH for binding to E06. In brief, a limited amount of E06-IgM antibody (2 μg/mL in PBS) was used to coat immunograde White U Bottom 96 Well Plates (Phenix Research, NC) overnight at 4° C. The plates were blocked by 1% fatty acid free BSA for 1 h at room temperature. Human or mouse serum/plasma (1:150) were incubate for 1 h at room temperature in the E06 coated plates to allow pre-binding. This was followed by PC-KLH (1 μg/mL) addition to the wells for 1 h at room temperature. After each 1 hour of incubation, the wells were washed 3 times with TBS. Alkaline phosphatase-conjugated anti-KLH antibody (source 600-405-466 Rockland Inc) was then applied to detect bound PC-KLH using Lumi-Phos 530. Data were collected as RLU/100 ms in a Synergy HTX Multi-Mode Reader (BioTek, VT). A standard curve of PC-KLH without serum/plasma competitor was run in parallel on each plate to allow calculation of concentration of immunodetectable OxPL in the samples. All determinations were done in triplicate.

Triglyceride and Cholesterol measurement: Blood/Tissue triglyceride and cholesterol levels were determined using the Triglyceride Quantification Colorimetric/Fluorometric Kit (k622 Biovision Inc.) and total Cholesterol and Cholesterol Ester Colorimetric/Fluorometric Kit (k603 Biovision Inc.) according to the manufacturer's instruction respectively. All values were analyzed from 12 hours fasted mice.

Free fatty acid and glycerol measurement: Blood free fatty acid and glycerol levels were measured with NEFA HR color reagent (Wako Life Sciences) and Free Glycerol Determination kit (Sigma) respectively, according to the manufacturer's instructions. All mice serum were from mice fasted for 12 hours.

Glucose and Insulin tolerance tests: Fasting blood glucose was measured after 12 hours fast, using Easy Step Blood Glucose Monitoring System. Mice were then intraperitoneally injected with D-[+]-glucose (Sigma) at a dose of 1 g/kg BW for ALMN diet-fed mice. Blood glucose levels were measured at 15, 30, 45, 60, 90 and 120 min after injection. For insulin tolerance test, fasting blood glucose was measured after 4 hours fast, using Easy Step Blood Glucose Monitoring System. Mice were then intraperitoneally injected with insulin (Humulin R) at a dose of 1.2 U/kg BW for AMLN diet-fed mice. Blood glucose levels were measured at 15, 30, 45, 60, 90 and 120 min after injection.

RNA-seq library preparation: Total RNA was isolated from mice livers homogenized with TRIzol reagent and purified using Quick RNA mini prep columns and RNase-free DNase digestion according to the manufacturer's instructions (Life Technologies Co.). RNA quality was assessed by an Agilent 2100 Bioanalyzer. Sequencing libraries were prepared in biological replicates from polyA enriched mRNA. RNA-seq libraries were prepared from poly(A)-enriched mRNA as previously described (Oishi et al., 2017). Libraries were size selected by gel extraction, quantified using a Qubit dsDNA HS Assay Kit (Thermo Fisher Scientific) and sequenced on a Hi-seq 4000 or a NextSeq 500 (Illumina, San Diego, CA) according to the manufacturer's instructions.

RNA-seq analysis: RNA-seq analysis was conducted as previously described (Link et al., 2018). FASTQ files from sequencing experiments were mapped to the mouse mm10 genome. STAR with default parameters was used to map RNA-seq experiments (Dobin et al., 2013). To compare differential gene expression between indicated groups, HOMER's analyzeRepeats with the option rna and the parameters-condenseGenes, -noadj, and -count exons was used on two-three replicates per condition (Heinz et al., 2010a). Each sequencing experiment was normalized to a total of $10^7$ uniquely mapped tags by adjusting the number of tags at each position in the genome to the correct fractional amount given the total tags mapped. Sequence experiments were visualized by preparing custom tracks for the UCSC genome browser. Differential gene expression was assessed with DESeq2 using HOMER's getDiffExpression.pl with the parameters −p-adj 0.05 and −log 2 fold 0.585 (for 1.5-fold differently expressed genes) (Love et al., 2014). For all genes the TPM (transcript per kilobase million) values were plotted and colored according to fold change. For various ontology analyses, either HOMER or Metascape was used (Tripathi et al., 2015).

PGC1α ChIP-seq of hepatic nuclei: Livers from AMLN diet-fed Ldlr$^{-/-}$ and E06-scFvLdlr$^{-/-}$ mice were crosslinked by a two-step perfusion method. Briefly, 1 mg/mL disuccinimidyl glutarate (DSG) in PBS was used to perfuse the liver for 30 min, followed by 1% PFA in PBS for 10 min. Afterward, the livers were perfused with 20 mL 0.125M glycine to quench the crosslinking. After sequential flows, livers were Dounce homogenized and filtered through 70 μm strainer and washed with NF buffer (10 mM Tris-HCl, pH8.0, 1 mM EDTA, 5 mM MgCl$_2$, 0.1M Sucrose, 0.5% Triton X-100). Liver homogenate were then centrifugation at 1200 g for 7 min, then washed with 10 mL HBSS (adding 1% BSA, 1 mM EDTA) and filtered through 30 μm strainer. Hepatic nuclei were then washed again with 15 mL HBSS (adding 1% BSA, 1 mM EDTA) followed by centrifugation and the pellet was saved for ChIP-seq. ChIP from hepatic nuclei was performed as described previously (Oishi et al., 2017). Briefly, nuclei were suspended in 130 ul RIPA-NR lysis buffer (20 mM Tris/HCl pH7.5, 1 mM EDTA, 0.5 mM EGTA, 0.1% SDS, 0.4% Na-Deoxycholate, 1% NP-40 alternative, 0.5 mM DTT, 1× protease inhibitor cocktail (Sigma), 1 mM PMSF) and chromatin was sheared by sonication using a Covaris E220 for 18 cycles with the following setting: time, 60 s; duty, 5.0; PIP, 140; cycles, 200; amplitude, 0.0; velocity, 0.0; dwell, 0.0. Immunoprecipitation was carried out with 2.5 μg each of the indicated PGC1α antibodies (sc-517380 from Santa Cruz Biotechnology and NBP1-04676 from Novus Biologicals) with slow rotation at 4° C. overnight. Libraries were PCR amplified for 12-15 cycles, size selected by gel extraction, and sequenced on a NextSeq 500 to a depth of 10-20 million reads.

ChIP-seq analysis: ChIP-seq analysis was conducted as previously described (Link et al., 2018). FASTQ files from sequencing experiments were mapped to the mouse mm10 genome using Bowtie2 with default parameters (Langmead and Salzberg, 2012). HOMER was used to convert aligned reads into "tag directories" for further analysis (Heinz et al., 2010b). ChIP-seq experiments were performed in replicate with corresponding input experiments. Peaks were called with HOMER for each tag directory with relaxed peak finding parameters −L 0 −C 0 −fdr 0.9 against the corresponding input directory. IDR (Li et al., 2011) was used to test for reproducibility between replicates, and only peaks with IDR<0.05 were used for downstream analysis. The pooled tag directory from two replicates was used for track visualization. To quantify transcription factor (TF) binding, peak files were merged with HOMER's mergePeaks and annotated with raw tag counts with HOMER's annotatePeaks using parameters -noadj, -size given. Subsequently, DESeq2 (Love et al., 2014) was used to identify the differentially bound TF with >2 fold-change and p-adj<0.05, unless stated otherwise in the text. The UCSC genome browser (Kent et al., 2002) was used to visualize ChIP-seq data.

Each sequencing experiment was normalized to a total of $10^7$ uniquely mapped tags by adjusting the number of tags at each position in the genome to the correct fractional amount given the total tags mapped. Sequence experiments were visualized by preparing custom tracks for the UCSC genome browser.

Transmission electron microscopy: Mice were perfused with 10 ml of modified Karnovsky's fixative (2.5% glutaraldehyde and 2% paraformaldehyde in 0.15 M sodium cacodylate buffer, pH 7.4) carefully. Liver were then dissected and fixed for at least 4 hours, postfixed in 1% osmium tetroxide in 0.15 M cacodylate buffer for 1 hour and stained en bloc in 2% uranyl acetate for 1 hour. Samples were dehydrated in ethanol, embedded in Durcupan epoxy resin (Sigma-Aldrich), sectioned at 50 to 60 nm on a Leica UCT ultramicrotome, and picked up on Formvar and carbon-coated copper grids. Sections were stained with 2% uranyl acetate for 5 minutes and Sato's lead stain for 1 minute. Grids were viewed using a JEOL 1200EX II (JEOL, Peabody, MA) transmission electron microscope and photographed using a Gatan digital camera (Gatan, Pleasanton, CA), or viewed using a Tecnai G2 Spirit BioTWIN transmission electron microscope equipped with an Eagle 4 k HS digital camera (FEI, Hilsboro, OR).

ROS and Mitochondrial membrane potential measurement: Total ROS was determined with Total ROS detection Kit (ENZ-51011 Enzo Life Sciences Inc.) and mitochondrial ROS levels using MitoSOX (Invitrogen) following the manufacturers' instructions. Mitochondrial membrane potential (Ψm) was measured using TMRM as previously described (Shimada et al., 2012).

Ex vivo/in vitro fatty acid oxidation assay: Liver or adipose tissues were dissected, weighted, quickly rinsed in PBS. Minced tissues were placed in 96-well tissue culture plate. For cultured cells, PBS was used to rinse the cells. Fatty Acid Oxidation was measured with combination of Fatty Acid Oxidation Assay Kit (Abcam) and Oxygen Consumption Assay Kit (Abcam) according to the manufacturer's instruction. 150 μl reaction medium and 10 μl oxygen consumption reagent were added to each well. Wells were sealed with pre-warmed high sensitivity mineral oil. Fluorescence was measured at 37° C. for 30 min by Tecan Infinite M200 Pro.

Immunoprecipitation: Liver tissue was homogenized in PBS with freshly added protease inhibitors tablet (Roche). Immunoprecipitation was performed with anti-SOD2 antibody (Abcam) overnight at 4C followed by incubation with Protein A/G agarose beads for 4 h at 4° C. Protein A/G beads were washed with PBS for 6 times. Protein was eluted with SDS loading buffer.

Western blot: Immunoprecipated MnSOD complex was resolved by SDS-PAGE and transferred to nitrocellulose membranes (Bio-Rad). Nitrocellulose membranes were sequentially blocked by 5% milk and Avidin/Biotin blocking buffer. Biotinlyzed-E06 antibody was used to detect OxPL modification on MnSOD. E06 signal was visualized on film using horseradish peroxidase-conjugated NeutrAvidin (Life Technologies) and SuperSignal West Pico Chemilunminescent Substrate (Thermo Scientific).

In vitro modification of SOD and SOD activity: Recombinant human MnSOD (Abcam, ab82656) was incubated with POVPC (Avanti Polar Lipids, 870606) (molar ration 1:40) or vehicle at 37° C. overnight. 300 μg/mL NaBH3CN was added to stabilize reversible OxPL adducts. Both native and POVPC modified MnSOD were dialyzed extensively against PBS. SOD activity of recombinant and modified MnSOD and liver and cell lysates was measured with Superoxide Dismutase Activity Assay Kit (Abcam) according to the manufacturer's instruction.

NAD/NADH ratio measurement: Tissue NAD/NADH ratio was measured with NAD/NADH Assay kit (Abcam) according to manufacturer's instruction. Tissues were dissected, rinsed in PBS, and homogenized in NAD/NADH extraction buffer from the kit. After centrifugation, supernatants were collected for measurements.

Serum cytokine analysis: Serum cytokine levels of mice, including TNF-α, GM-CSF, MIP-1β and RANTES, were measured used a Bio-Plex Pro™ Mouse Cytokine 23-Plex panel using the Bio-Plex® Protein Array system (Bio-Rad Laboratories, Hercules, CA, USA) following manufacturer instructions.

LDL uptake assay. Fluorescence-labelled LDL (Dil-OxLDL/Dil-nLDL) were used. HepG2 cells were serum starved for four hours. 10 μg/mL Dil-OxLDL or Dil-nLDL were incubated with HepG2 cells for 3 hours. Cells were washed 3 times with cold PBS and fixed with 10% buffered formalin for 10 min at room temperature. Cellular uptake of OxLDL/nLDL were measured by fluorescence intensity or confocal microscopy. Fluorescence intensity was measured (absorption/emission: 554/571 nm). In some experiments, nuclei were co-stained with DAPI, and confocal imaging was conducted to capture images of indicated groups of HepG2 cells.

Fatty acid uptake assay. Fluorescence-labelled fatty acid (BODIPY-fatty acids) was used. HepG2 cells were serum starved for four hours. 1 μM BODIPY-fatty acids (BODYPI-FA) was pre-conjugated with 1% BSA at 37 C for 1 hour. BODIPY-FA/BSA pre-incubated with IgM isotype control or E06 IgM were incubated with HepG2 cells for 30 min. Cells were washed 3 times with cold PBS and fixed with 10% buffered formalin for 10 min at room temperature. Cell uptake of BODIPY-FA were measured by fluorescence intensity or confocal microscopy. Fluorescence intensity was measured (absorption/emission: 500/510 nm). In some experiments, nuclei were co-stained with DAPI, and confocal imaging was conducted to capture images of indicated groups of HepG2 cells.

Measurement of mtDNA copy number. Total liver DNA of AMLN diet-fed Ldlr$^{-/-}$ and E06-scFv Ldlr$^{-/-}$ mice was isolated using PureLink DNA Mini Kit (K182002, Life Technologies) according to manufacturer's instruction. mtDNA was quantified by qPCR using primers specific for the mitochondrial D-loop region or a specific region of mtDNA that is not inserted into nuclear DNA (non-NUMT) (Malik et al., 2016). Nuclear DNA encoding Tert and B2m was used for normalization. Primer sequences are as follows:

32

```
                                          (SEQ ID NO: 1)
D-loop F:        5'-AATCTACCATCCTCCGTGAAACC-3';

(SEQ ID NO: 2)
D-loop R:        5'-TCAGTTTAGCTACCCCCAAGTTTAA-3';

(SEQ ID NO: 3)
Tert F:          5'-CTAGCTCATGTGTCAAGACCCTCTT-3';

(SEQ ID NO: 4)
Tert R:          5'-GCCAGCACGTTTCTCTCGTT-3';

(SEQ ID NO: 5)
B2m F:           5'-ATGGGAAGCCGAACATACTG-3';

(SEQ ID NO: 6)
B2m R:           5'-CAGTCTCAGTGGGGGTGAAT-3';

(SEQ ID NO: 7)
non-NUMT F:      5'-CTAGAAACCCCGAAACCAAA-3';
and (SEQ ID NO: 8)
non-NUMT R:      5'-CCAGCTATCACCAAGCTCGT-3'.
```

Statistical Analyses: All data of animal and human studies are shown as mean±SEM. Replicates are indicated in figure legends. N represents the number of experimental replicates. F-test was performed to determine the equality of variance. When comparing two groups, statistical analysis was performed using a two-tailed Student's t-test, except when the f-test suggested that variances were statistically different. For analysis of more than two groups, analysis of variance (ANOVA) was used to determine equality of variance. Comparisons between groups were performed with Tukey-Krammer post-hoc analysis (Zhao et al., 2018). For all tests, $P<0.05$ was considered statistically significant.

Figure 1A:
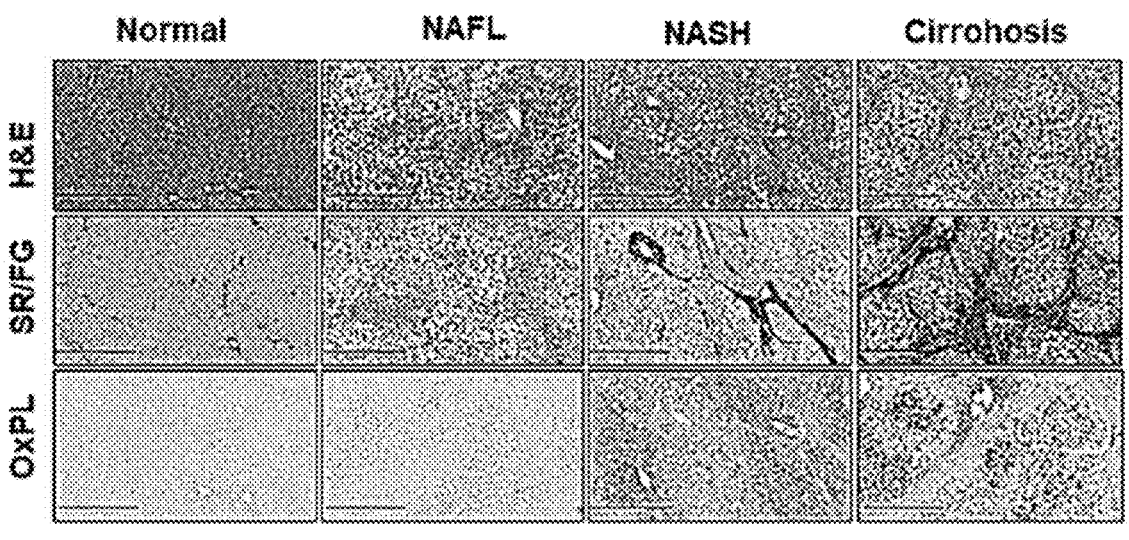
Figure 1D:
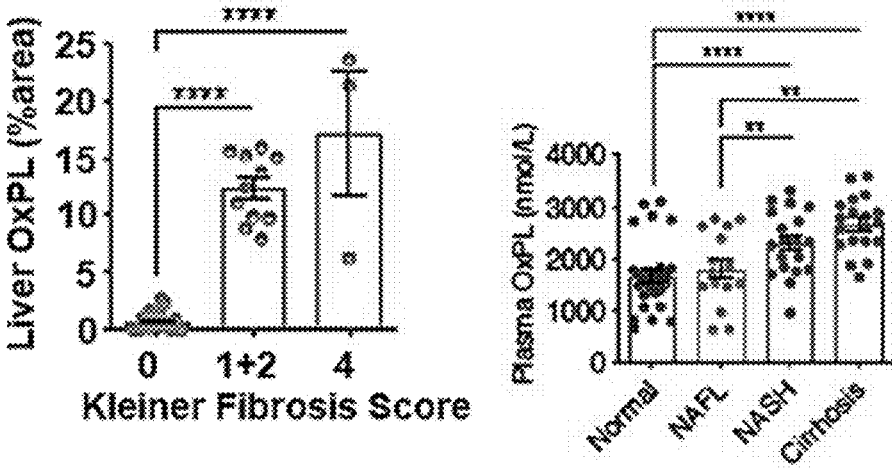
Figure 1D:
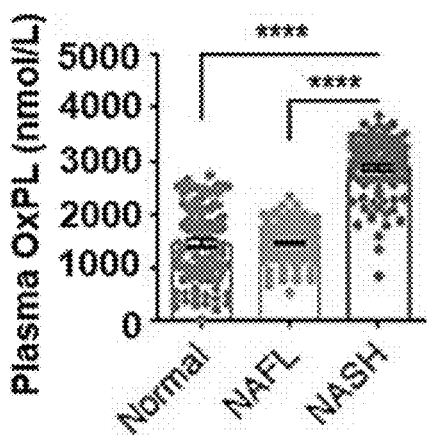

OxPL accumulate in liver and serum of human and mouse NASH. To determine if OxPL accumulate during the pathogenesis of human NASH, E06 was used to stain OxPL in human liver sections, which were diagnosed in blinded fashion by a liver-experienced pathologist into the following categories: normal, steatosis (NAFL), and NASH induced liver fibrosis stage 1, 2, and 4. H&E and Sirius Red/Fast Green (SR/FG) staining were conducted to indicate the extent of hepatic steatosis and fibrosis respectively. OxPL content was increased in liver sections from NASH (n=11, steatosis and Kleiner fibrosis score 1-2) and NASH-associated cirrhosis (n=3, steatosis, Kleiner fibrosis score 4 and plural pseudo-lobules) subjects compared with normal (n=10, no steatosis and Kleiner fibrosis score 0) and NAFL (n=10, steatosis and Kleiner fibrosis score 0) subjects (FIG. 1A). Of note, OxPL distributed in locales surrounding the extensive fibrosis shown by SR/FG staining. The quantified liver OxPL staining area showed a positive correlation to fibrosis scores (FIG. 1B). Moreover, plasma of subjects in whom liver status had been previously determined by liver biopsy was examined (Gorden et al., 2015). Plasma OxPL was measured by a newly developed competitive ELISA. Elevated plasma OxPL levels were observed in both NASH (n=19) and cirrhosis (n=19) patients, and both groups were distinguished from normal (n=29) or NAFL groups (n=15) (FIG. 1C). In a third study, plasma of patients from an outpatient clinic who were diagnosed as normal were analyzed (n=107), NAFL (steatosis by ultrasound with normal liver ALT and AST levels, n=118) or NASH (steatosis and both elevated ALT and AST, n=100). In this cohort, plasma OxPL levels were significantly elevated in NASH subjects compared to normal or NAFL subjects (FIG. 1D). These preliminary data suggest that increased OxPL accumulate in both liver and plasma of humans with NASH.

Figures 1E, 1F, 1G:
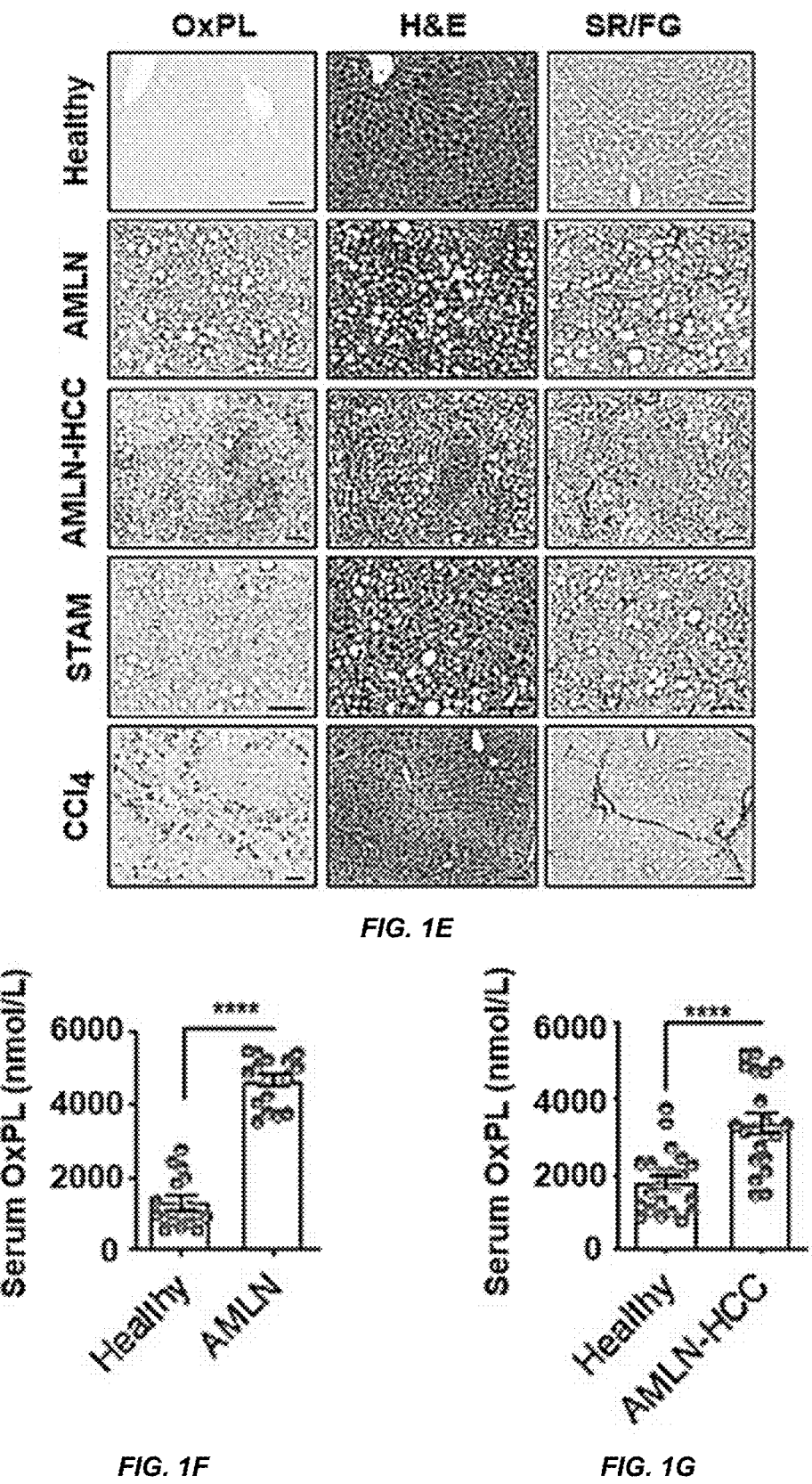

To determine if OxPL accumulate in murine NASH models, OxPL levels were examined in healthy mice and different NASH/liver damage models (The timeframe for each of the 4 NASH/liver damage models examined here are shown in FIG. 7A-D). Serial hepatic sections were stained with E06, H&E and Sirius Red/Fast Green (SR/FG) to indicate the extent of hepatic OxPL accumulation, steatosis, and fibrosis respectively in the same liver areas. Serum OxPL was also measured by the competitive ELISA. Ldlr$^{-/-}$ mice fed the AMLN diet for 30 weeks developed human NASH features, including steatosis, inflammation and pericellular fibrosis (FIG. 1E-AMLN). Of note, there was marked accumulation of OxPL in the liver (FIG. 1E-AMLN). Total-OxPL was significantly increased in the blood of these mice by about 3-fold (FIG. 1F). Moreover, these mice developed HCC with prolonged feeding of AMLN diet (FIG. 1E-AMLN-HCC). After 48 weeks of feeding, there was marked accumulation of OxPL in the liver, especially at the tumor sites shown by H&E staining (FIG. 1E-AMLN-HCC) and enhanced OxPL levels in serum (FIG. 1G). Similarly, high-fat diet (HFD)-fed streptozotocin-treated Ldlr$^{-/-}$ mice (STAN) developed NASH with mild fibrosis after only 4 weeks of feeding, and these mice also exhibited substantially elevated liver and blood OxPL (FIG. 1E-STAM, H). Intraperitoneal injection of CCl$_4$ enhances free radical formation and rapidly induces hepatic damage (Muriel, 2017; Shrestha et al., 2016). In this model of repeated CCl$_4$ administration over 4 weeks, there was OxPL accumulation in liver in areas coinciding with damaged hepatocytes and adjacent to the collagen fibers as shown by both H&E and SR/FG staining and serum OxPL levels were also increased ~3-fold (FIG. 1E—CCl$_4$, I).

Figures 1H, 1I, 2A, 2B, 2C:
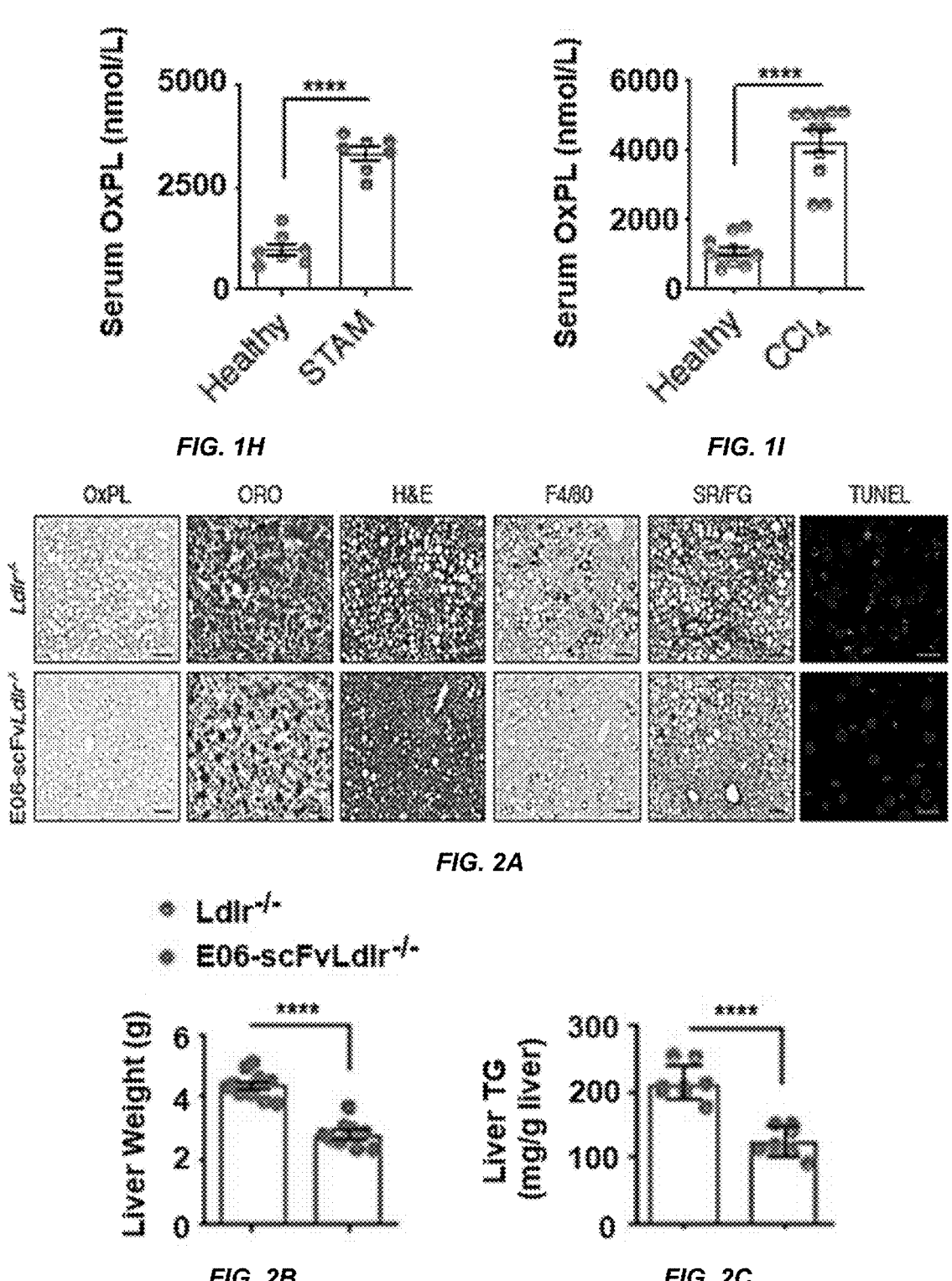
Figures 2D, 2E, 2F, 2G, 2H, 2I, 2J:
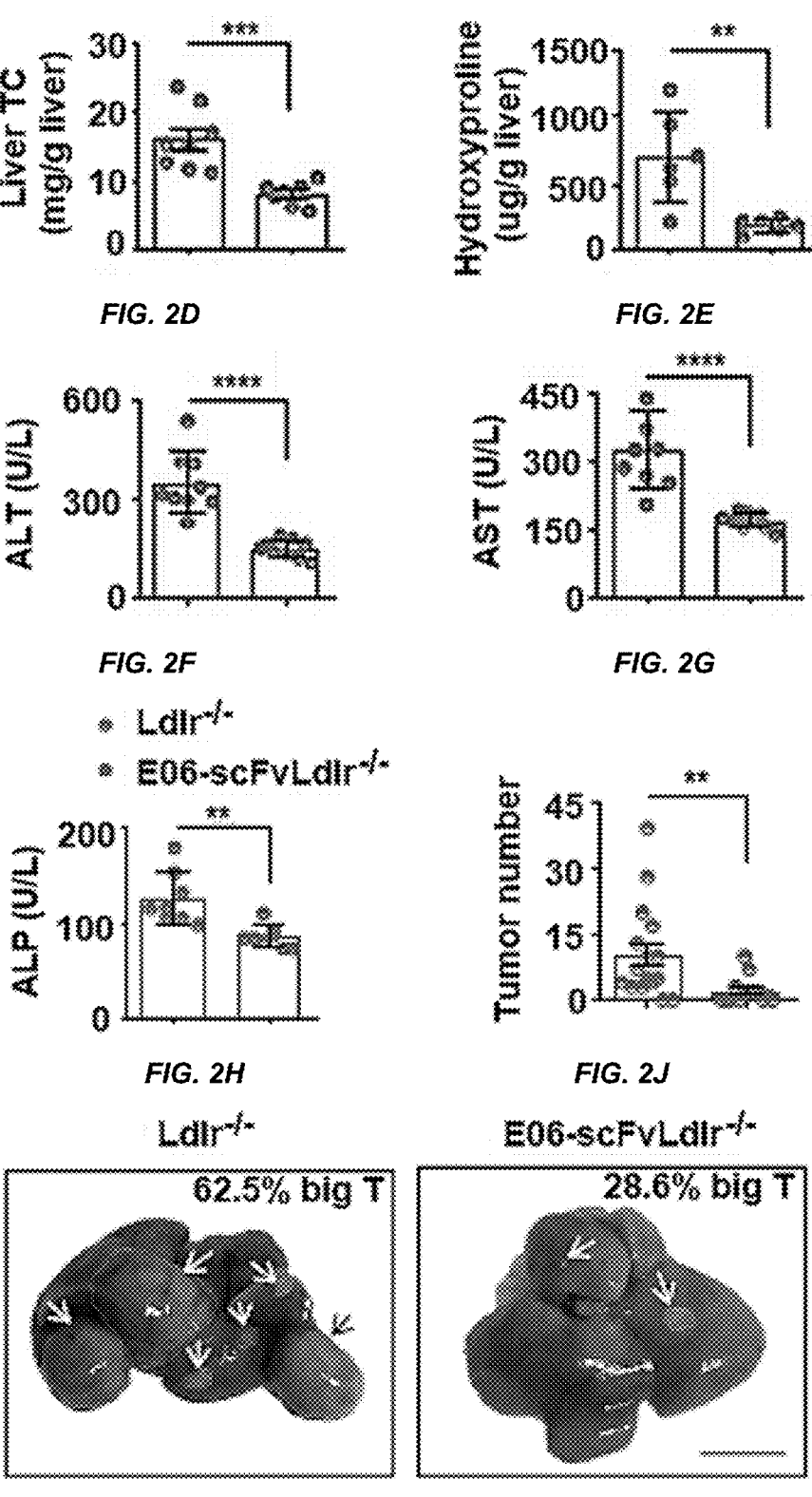
FIG. 2A-T shows neutralization of OxPL restrains AMLN diet-induced hepatic steatosis, inflammation and fibrosis, increases energy expenditure and attenuates AMLN diet-induced obesity. (A-H, L-T) Ldlr$^{-/-}$ and E06-scFvLdlr$^{-/-}$ mice were fed chow or AMLN diet for 30 weeks starting at 8 weeks of age. (A) Paraffin/OCT-embedded mouse liver sections were stained with E06 IgM antibody to determine OxPL; Oil Red O (ORO) to determine neutral lipid deposition; haemotoxylin and eosin (H&E) to determine liver histology; Antibody F4/80 to determine macrophage accumulation; Sirius Red/Fast Green (SR/FG) to determine collagen fiber deposition; and TUNEL to determine liver apoptosis. N=6. (for TUNEL staining, scale bar=20 μm). (B) Liver weight of indicated mice. N=10. (C-E) Content of liver triglyceride (C, TG), total cholesterol (D, TC) and hydroxyproline (E) of indicated mice. N=5-8. (F-H) Serum Alanine Aminotransferase (F, ALT), Aspartate Aminotransferase (G, AST) and Alkaline Phosphatase (H, ALP) of indicated mice. N=8-9. (I) Representative gross liver morphology and big tumor (big T, >0.4 cm) incidence in indicated mice after 48 weeks of AMLN diet, n=14-16. Scale bar=1 cm. (J, K) Tumor numbers (J) and volumes (K) of same mice as in (I). (L) Body weights of indicated mice at baseline (8 weeks old) and after 30 weeks of indicated diet feeding. N=6-10 per group. (M) Photo of representative indicated mice after 30 weeks of AMLN diet and H&E staining of respective IWAT. (N) Percentage of fat mass of mice as determined by DEXA imaging. N=4-6. (O-Q) IWAT (O), EWAT (P) or BAT (Q) mass in indicated mice. N=6-10. (R, S) Oxygen consumption rate over time (R, VO$_2$) and ANCOVA analyzed VO2 statistics (S, normalized to body weight) of respective mice of indicated groups. N=4-5. (T) ANCOVA analyzed energy expenditure (normalized to body weight) of mice in experiment shown in panel R and S. Data are mean±SEM. *, P<0.05; , P<0.01; *, P<0.001; **, P<0.0001. Scale bar=100 μm for all panels unless otherwise specified. See also FIG. 8**.
Figures 7C, 7D, 8A, 8B, 8C, 8D:
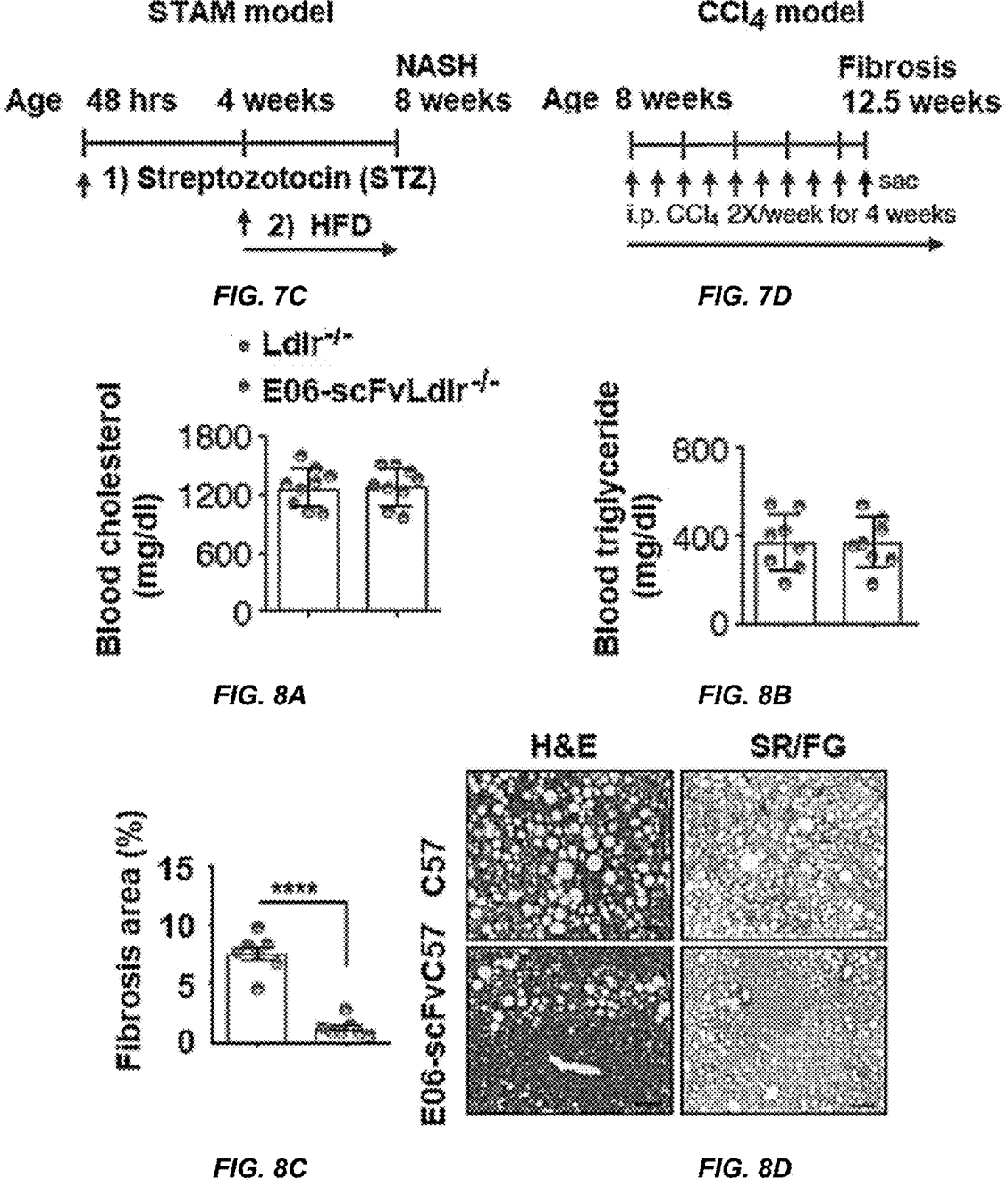

Neutralization of OxPL protects against NASH in multiple models. Experiments were performed to determine if the increased serum and liver OxPL promotes the pathogenesis of NASH. To accomplish this, the recently developed transgenic mice that express E06-scFv were used to neutralize OxPL in vivo (Que et al., 2018). Immunohistological staining with IgM E06 of livers from AMLN-fed E06-scFvLdlr$^{-/-}$ mice showed a reduction in hepatic content of immunological recognized OxPL compared to Ldlr$^{-/-}$ mice (FIG. 2A—OxPL). (A caveat is that hepatocytes are a major source of the E06-scFv). E06-scFvLdlr$^{-/-}$ and Ldlr$^{-/-}$ mice have similar levels of serum cholesterol (~1300 mg/dL) and triglyceride (~400 mg/dL) (FIGS. 8A and B). There was a substantial reduction in steatosis, which was confirmed by a significant reduction in liver weight, and by ~50% reduction in hepatic triglyceride and ~45% reduction in cholesterol content (FIG. 2A-D). E06-scFv substantially ameliorated hepatic inflammation as evidenced by decreased macrophage F4/80 staining (FIG. 2A). Of particular note, there was ~70% reduction of liver fibrosis as measured by SR/FG staining, and a ~70% reduction measured by hydroxyproline content (FIGS. 2A, 2E and 8C). Moreover, decreased TUNEL staining observed in livers of E06-scFvLdlr$^{-/-}$ mice support reduced hepatocyte death, which is reflected in lower serum ALT, AST and ALP levels (FIG. 2A, F-H). The histological features were blindly assessed by an experienced pathologist according to Kleiner Scoring System (Kleiner et al., 2005). Steatosis, inflammation, hepatocellular injury and fibrosis were all substantially decreased in AMLN-fed E06-scFvLdlr$^{-/-}$ mice compared to Ldlr$^{-/-}$ mice. The profound protective effect of neutralization of OxPL also extended to protection against hepatocellular carcinoma, as evidenced by a marked decrease of big tumor (T) incidence (>4 mm), tumor number and volume in the E06-scFvLdlr$^{-/-}$ mice fed with AMLN diet for 48 weeks (FIG. 2I-K).

Importantly, the protective effects on E06-scFv were validated in AMLN-fed C57BL/6 and E06-scFv C57BL/6 mice that had normal low LDL cholesterol levels (FIGS. 8D and E). In a similar intervention study in STAM mice, expression of E06-scFv improved both hepatic steatosis and fibrosis (FIG. 8F). These observations indicate that efficient neutralization of OxPL attenuates NASH in multiple models.

Figures 2P, 2Q, 2R, 2S, 2T:
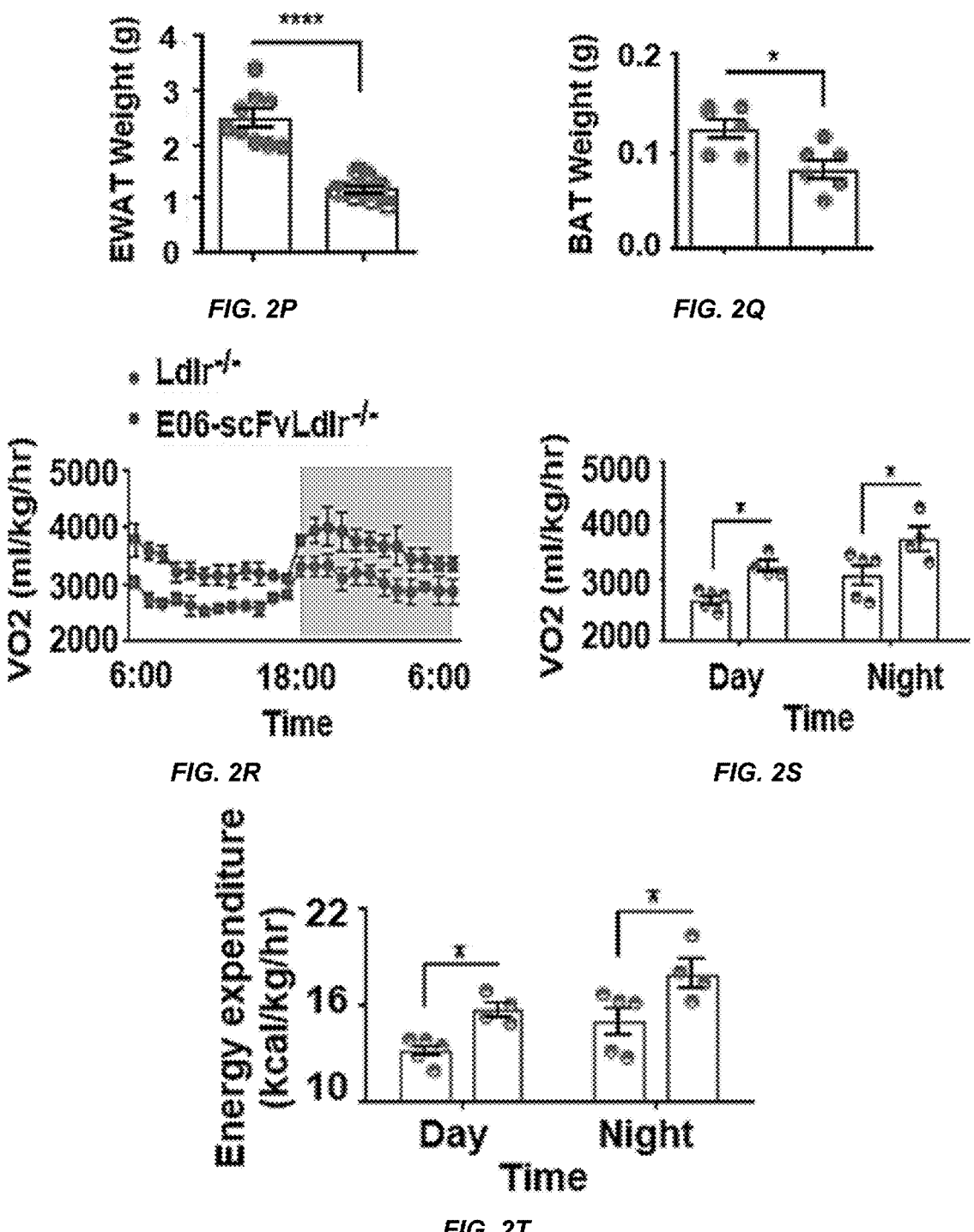

Neutralization of OxPL increases energy expenditure and attenuates diet-induced obesity. Neutralizing OxPL had no effect on body weight in chow-fed mice. However, when fed the AMLN diet, E06-scFvLdlr$^{-/-}$ mice gained less body weight compared to Ldlr$^{-/-}$ mice (FIG. 2L, M). Adipocyte size was smaller in AMLN diet-fed E06-scFvLdlr$^{-/-}$ mice (FIG. 2M, right), suggesting that OxPL neutralization attenuates AMLN diet-induced adipocyte hypertrophy. Dual energy X-ray absorptiometry (DEXA) scanning revealed that E06-scFvLdlr$^{-/-}$ mice had significantly less fat mass (FIG. 2N, FIG. 8G), which was confirmed by decreased weight of inguinal White Adipose Tissue (IWAT), epididymal White Adipose Tissue (EWAT), and Brown Adipose Tissue (BAT) in E06-scFvLdlr$^{-/-}$ mice (FIG. 2O-Q). ANCOVA analysis with total body weight as covariant, or lean body mass as covariant, both indicated increased oxygen consumption rate and energy expenditure in AMLN-fed E06-scFvLdlr$^{-/-}$ mice compared to Ldlr$^{-/-}$ mice (FIG. 2R-T, 8H-I). Note that no difference in oxygen consumption rate was observed when the mice were on chow diet (FIG. 8J). Neutralization of OxPL did not affect respiratory exchange rate (RER), physical activity or food intake (FIG. 8K-M). Neutralization of OxPL also did not affect serum nonesterified fatty acid (NEFA) or glycerol concentrations (FIG. 8N, O), nor did it alter glucose homeostasis, as indicated by similar fasting glucose and insulin levels (FIG. 8P, Q) and similar glucose tolerance and insulin sensitivity (FIG. 8R, S). These data suggest that insulin sensitivity was not affected by expression of E06-scFv in the context of the AMLN diet.

Neutralization of OxPL protects mitochondria and promotes mitochondrial biogenesis. To assess putative mechanisms by which targeting OxPL restrains NASH, RNA-seq of livers from AMLN-fed Ldlr$^{-/-}$ and E06-scFvLdlr$^{-/-}$ mice were performed. 1628 genes were significantly up-regulated (fold change>1.5, p-adj<0.05) in E06-scFvLdlr$^{-/-}$ livers (FIG. 3A, blue dots). Gene ontology analysis revealed that top enriched pathways in E06-upregulated genes were related to mitochondrial functions, such as oxidative phosphorylation, respiratory chain complex assembly, fatty acid metabolism, and fatty acid transport (FIG. 3B). The relative fold increase of 72 genes in the E06-scFvLdlr$^{-/-}$ mice most closely related to mitochondrial function (Mito function) is depicted relative to overall liver mRNA fold change (FIG. 3A, red dots). These 72 genes include 63 oxidative phosphorylation genes, 6 mitochondrial assembly genes, and 4 fatty acid transportation genes (FIG. 3C). Note that the expression of these genes was not regulated by E06 in chow diet-fed mice (FIG. 9). Collectively, these findings indicate that in the context of the AMLN diet, OxPL significantly down-regulates expression of genes regulating mitochondrial function, which E06-scFv effectively counteracts.

Figures 4E, 4F, 4G, 4H, 4I:
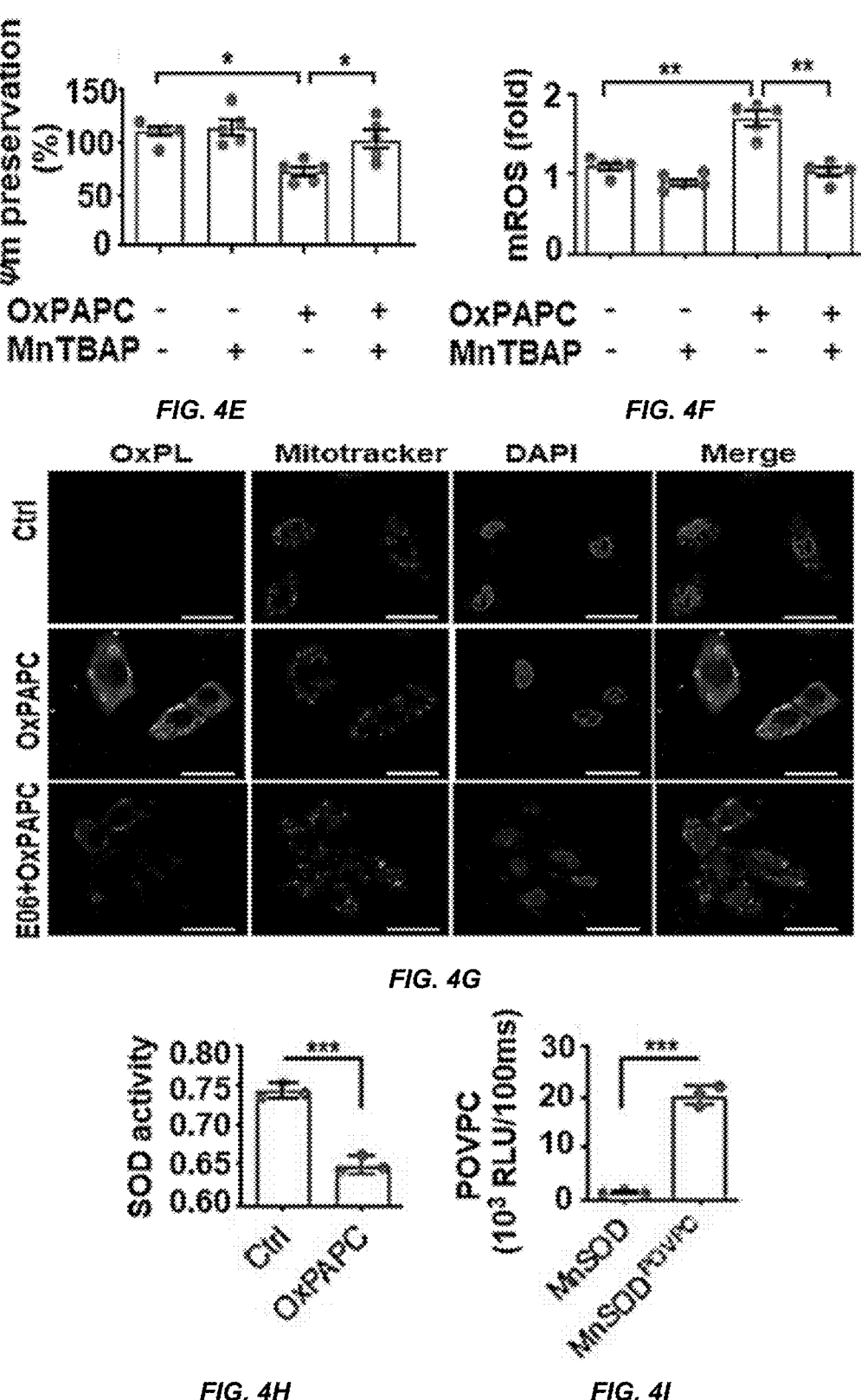

Oxidative stress plays an important role in NASH (Mansouri et al., 2018). The balance between oxidant and antioxidant agents controls redox state. ROS generation during chronic hepatic steatosis and inflammation leads to oxidative damage to mitochondrial proteins, membranes and impaired oxidative phosphorylation (Ucar et al., 2013). In this study, the experiments demonstrate that OxPL directly induces ROS accumulation. Ldlr$^{-/-}$ and E06-scFvLdlr$^{-/-}$ primary hepatocytes were treated with oxidized 1-palmitoyl-2-arachidonoyl-sn-glycero-3-phosphocholine (OxPAPC, a mixture of OxPL). OxPAPC treatment significantly increased total ROS (tROS) accumulation in Ldlr$^{-/-}$ hepatocytes, but not in E06-scFvLdlr$^{-/-}$ hepatocytes (FIG. 4A), which secrete E06-scFv into the medium (after 12 hours, about 1/6 the concentration found in serum of E06-scFv mice) (FIG. 10A). Additionally, OxPAPC diminished mitochondrial membrane potential (FIG. 4B) and stimulated mitochondrial ROS (mROS) accumulation (FIG. 4C) in Ldlr$^{-/-}$ but not in E06-scFvLdlr$^{-/-}$ hepatocytes, indicating sustained mitochondrial damage induced by OxPL. As a result, Ldlr$^{-/-}$ hepatocytes exhibited significantly compromised fatty acid oxidation in response to OxPAPC, which was preserved in E06-scFvLdlr$^{-/-}$ hepatocytes (FIG. 4D). To confirm that OxPL-induced mitochondrial damage can be attributed in part to ROS, hepatocytes were pretreated with the ROS scavenger MnTBAP, a cell-permeable MnSOD/SOD2 mimetic. MnTBAP pretreatment restored OxPL-diminished mitochondrial membrane potential (FIG. 4E). MnTBAP abrogated both mitochondrial and total ROS accumulation in hepatocytes exposed to OxPAPC (FIG. 4F, FIG. 10B). These results indicate that OxPL induces hepatocyte mitochondrial dysfunction and damage by increasing ROS accumulation.

Given that MnTBAP abolished OxPAPC-induced mROS accumulation, it was queried whether one mechanism by which OxPAPC might induce mROS accumulation is by binding to MnSOD, thereby decreasing its antioxidant activity. To test this hypothesis, primary hepatocytes were acutely treated with OxPAPC for one hour, which significantly increased intracellular and mitochondrial OxPAPC levels, as detected by E06, whereas pre-incubation of OxPAPC with E06 antibody significantly reduced the amount of OxPAPC entering the cells (FIG. 4G). The specificity of E06 neutralizing OxPL epitopes was further validated. Incubation of Dil-OxLDL with hepatocytes led to substantial uptake, whereas preincubation in the presence of E06 IgM antibody reduced its uptake (FIG. 10C, E). In contrast, E06 did not affect fatty acid (BODIPY-fatty acids) uptake (FIG. 10D, F) or that of native LDL (FIG. 10G). These data indicate that E06 specifically blocks OxPL epitopes from entering hepatocytes. Further, OxPAPC substantially reduced SOD activity within 1 hour (FIG. 4H), indicating regulation of SOD by OxPL. Reactive OxPL such as 1-palmitoyl-2-(5'-oxo-valeroyl)-sn-glycero-3-phosphocholine (POVPC) can form covalent adducts with proteins, which are recognized by E06 (Friedman et al., 2002). To test whether OxPL could affect MnSOD activity through direct modification of MnSOD, recombinant MnSOD was incubated with POVPC to generate POVPC adducts with MnSOD. Compared to native MnSOD, POVPC modified MnSOD was strongly bound by E06 in an ELISA format (FIG. 4I). Moreover, POVPC modified MnSOD had significantly decreased activity (FIG. 4J). To determine the relevance of these observations to NASH livers, MnSOD was immunoprecipitated from liver lysates of chow-fed and AMLN diet-fed Ldlr$^{-/-}$ and E06-scFvLdlr$^{-/-}$ mice, and performed western blots with E06. OxPL-modified MnSOD was not detectable in livers of chow-fed mice, but was readily observed in AMLN-diet fed Ldlr$^{-/-}$ mice, and this modification was abrogated by the expression of E06-scFv (FIG. 4K). Measurement of SOD activity in liver homogenates indicated that SOD activity was substantially reduced in the liver of AMLN diet-fed Ldlr$^{-/-}$ mice compared to E06-scFvLdlr$^{-/-}$ mice, but not in chow-fed mice (FIG. 4L), even though expression of Sod2 was not altered. In STAM-NASH model, SOD activity in livers of E06-scFvLdlr$^{-/-}$ mice was also significantly higher compared to that in Ldlr$^{-/-}$ mice (FIG. 10H). Taken together, these data suggest that OxPL can directly modify and inhibit MnSOD activity to promote accumulation of mitochondrial ROS. In addition, these are complex events and it is likely that indirect effects are involved in regulation of SOD as well. To confirm the redox status in vivo, the amount of plasma malondialdehyde (MDA) epitopes (products of lipid peroxidation) were measured using thiobarbituric acid-reactive substances (TBARS) assay. Plasma MDA levels were significantly lower in E06-scFvLdlr$^{-/-}$ mice than in Ldlr$^{-/-}$ mice, indicative of reduced generalized lipid peroxidation and oxidative stress (FIG. 4M). Using electron microcopy (EM), liver mitochondrial morphology was directly assessed in Ldlr$^{-/-}$ and E06-scFvLdlr$^{-/-}$ mice fed AMLN diet. Mitochondria of Ldlr$^{-/-}$ mice exhibited disrupted outer membranes and ballooned or rounded cristae (arrows) compared with mitochondria in E06-scFvLdlr$^{-/-}$ mice (FIG. 4N), indicative of protection of mitochondrial damage by E06. Note also there were less lipid droplets (asterisks) in the livers of E06-scFvLdlr$^{-/-}$ mice compared to Ldlr$^{-/-}$ mice.

As improvement of mitochondrial function would be predicted to increase respiration (Wu et al., 1999), NAD/NADH ratios were examined in AMLN diet-fed mice, and demonstrated that the NAD/NADH ratio was significantly higher in livers from E06-scFvLdlr$^{-/-}$ mice (FIG. 4O). This was accompanied by increased activity of SIRT1, an NAD-dependent protein deacetylase, in E06-scFvLdlr$^{-/-}$ mice (FIG. 4P). SIRT1 deacetylates peroxisome proliferator initiated receptor gamma and coactivator 1 alpha (PGC1α), a central regulator promoting mitochondria biogenesis, to enhance its activity, thus promoting mitochondrial biogenesis (Canto et al., 2009; Katsyuba et al., 2018). To assess whether PGC1α exhibits enhanced activity to induce mitochondrial biogenesis, ChIP-seq was performed to analyze the local regulatory landscapes of mitochondrial genes that were more highly expressed in E06-scFvLdlr$^{-/-}$ livers. The analysis demonstrates that PGC1α recruitment onto promoters and enhancers of these E06-upregulated genes was significantly induced in E06-scFvLdlr$^{-/-}$ livers (FIG. 4Q), exemplified by Ndufs8, Uqcr10, Cox6b1 and Atp5d, spanning mitochondrial respiratory chain complexes (FIG. 4R, the tick marks show E06-upregulated peaks). Consistent with enhanced expression of mitochondrial genes (FIG. 3C), an increase of mitochondrial number in the liver of AMLN diet-fed E06-scFvLdlr$^{-/-}$ mice was confirmed by MitoTracker staining (FIG. 4S) and mitochondrial DNA (mtDNA) copy number determined by mtDNA markers (D-loop and non-NUMT) to nuclear DNA markers (Tert and B2m) (FIG. 10I-J). Taken together, the data suggest that in the context of the AMLN diet, E06-scFv reduced OxPL mediated oxidative stress and mitochondrial damage, and led to an increased NAD/NADH ratio, which in turn activated SIRT1/PGC1α pathway to up-regulate mitochondrial biogenesis in a feedforward loop. Ex vivo experiments demonstrated that fatty acid oxidation in E06-scFvLdlr$^{-/-}$ livers was significantly higher (FIG. 4T). Consequently, improvement of mitochondrial function and increased mitochondrial biogenesis contributed to reduced lipid accumulation in the livers of E06-scFvLdlr$^{-/-}$ mice compared to Ldlr$^{-/-}$ mice (FIG. 4S, circles; FIG. 2A-D). Consistent with improved mitochondrial function and enhanced PGC1α activity, which plays an important role in defending against oxidative stress, higher expression was observed of antioxidant enzymes in E06-scFvLdlr$^{-/-}$ livers (FIG. 10K).

Since reduced fat mass and increased energy expenditure was observed in E06-scFvLdlr$^{-/-}$ mice on the AMLN diet, mitochondrial oxidative phosphorylation was also measured in IWAT. Both fatty acid oxidation and the NAD/NADH ratio were significantly increased in IWAT of E06-scFvLdlr$^{-/-}$ mice (FIG. 10L-M). This was accompanied by increased SIRT1 activity in adipose tissue of E06-scFvLdlr$^{-/-}$ mice (FIG. 10N). Staining of IWAT with MitoTracker revealed a substantial increase of mitochondria in adipocytes of E06-scFvLdlr$^{-/-}$ mice (FIG. 10O).

The apparent increase in mitochondrial function in both hepatocytes and adipose tissue on the AMLN diet suggested the possibility that E06-scFvLdlr$^{-/-}$ mice might also have improved thermogenic capacity despite the decreased white and brown adipose tissue mass due to less lipid accumulation. Indeed, the E06-scFvLdlr$^{-/-}$ mice demonstrated improved cold tolerance compared to Ldlr$^{-/-}$ mice (FIG. 10P). Collectively, these findings suggest that neutralizing OxPL improves mitochondrial function by reducing mitochondrial oxidative damage and increasing mitochondrial biogenesis.

Neutralization of OxPL suppresses AMLN diet-induced liver and systemic inflammation. Enhanced inflammation is widely recognized as a key driver of NASH and infiltration of inflammatory leukocytes plays essential roles in NASH (Alisi et al., 2017). To understand a potential role of OxPL in inflammatory immune cell populations in the AMLN-diet fed mice, flow cytometry was performed on hepatic non-parenchymal cell populations isolated from AMLN diet-fed Ldlr$^{-/-}$ and E06-scFvLdlr$^{-/-}$ mice. The final gating strategy to distinguish infiltrating blood monocytes and tissue macrophages. Importantly, staining for leukocytes with CD45, CD146, Fixvia-NIR, Ly6G, CX3CR1, as well as measuring Vitamin A autofluorescence excluded contamination with liver sinusoidal endothelial cells, dead cells, neutrophils and stellate cells respectively.

Figure 5B:
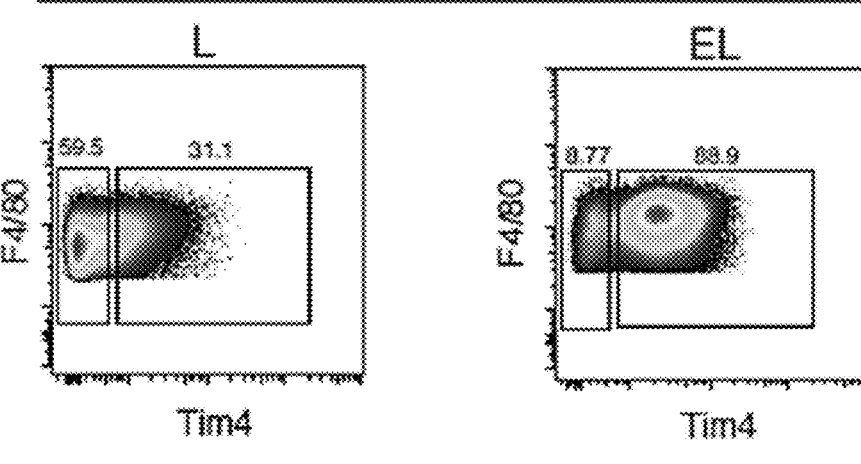
Figure 5C:
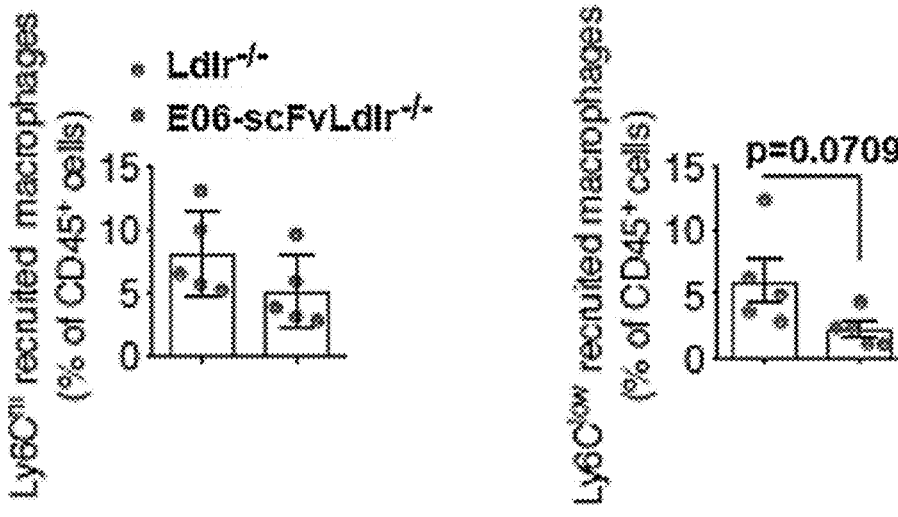
Figure 5D:
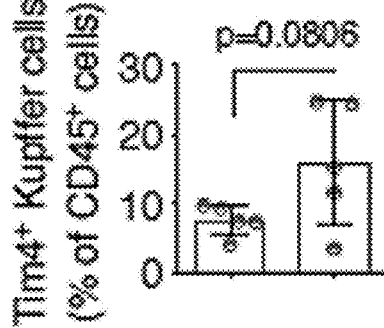

The data demonstrated that neutralization of OxPL tended to reduce recruitment of monocyte-derived macrophage characterized as Ly6C$^{hi}$CD45$^+$F4/80$^-$CD11b$^{hi}$Ly6G$^-$CD146$^-$Live and Ly6C$^{low}$CD45$^+$F4/80$^-$ CD11b$^{hi}$Ly6G$^-$CD146$^-$Live cells (FIG. 5A, C). Circulating pro-inflammatory cytokines mediating Ly6C$^{hi}$ monocyte infiltration and differentiation (RANTES, M-CSF, MIP-1b, TNF$\alpha$) were significantly decreased in E06-scFvLdlr$^{-/-}$ mice (FIG. 5E-H). Of interest, in parallel to the findings of decreased hepatic inflammation and apoptosis in the E06-scFvLdlr$^{-/-}$ mice (FIG. 2A), a significantly lower proportion of Tim4$^-$ macrophages were observed (FIG. 5B, D), which are thought to be a macrophage population derived from infiltrating monocytes during inflammation. Meanwhile, the proportion of resident Tim4$^+$ Kupffer cells (KC) that mediate engulfment of apoptotic cells moderately increased in E06-scFvLdlr$^{-/-}$ mice (FIG. 5B, D). The shift of Tim4$^-$ to Tim4$^+$ macrophages suggests less inflammation in the E06-scFvLdlr$^{-/-}$ mice.

Figures 5E, 5F, 5G, 5H, 5I:
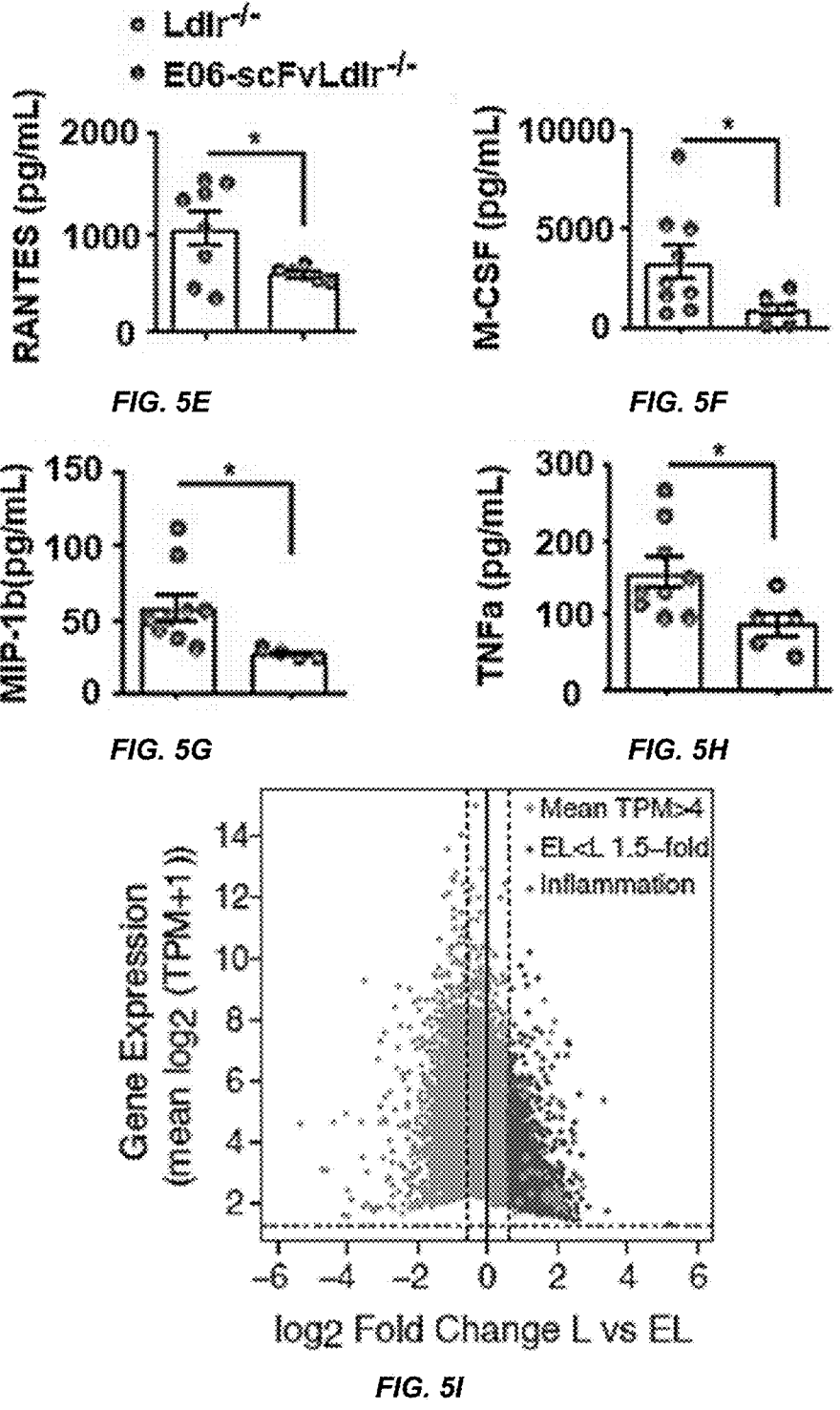
Figures 5J, 5K:
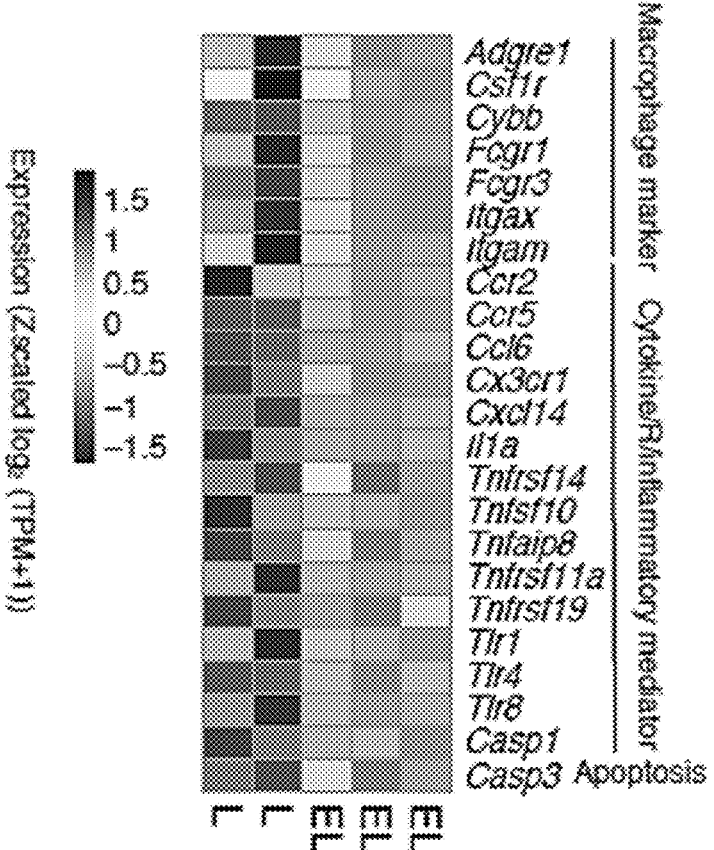

In support of a generally decreased inflammatory state in the E06-scFvLdlr$^{-/-}$ mice, RNA-seq analysis of whole liver revealed 1230 genes significantly down-regulated at a cutoff of 1.5-fold and a p-adj of 0.05 (FIG. 5I, red dots). Gene ontology analysis of reduced genes demonstrated that the top enriched pathways were linked to inflammation related categories including adhesion, cytokine production, leukocyte migration and myeloid leukocyte activation (FIG. 5J). The 23 genes downregulated in E06-scFvLdlr$^{-/-}$ mice corresponding to the inflammatory response term are colored in green (FIG. 5I). Expression of 7 macrophage marker genes (Adgre1, Csf1r, Cybb, Fcgr1, Fcgr3, Itgax, Itgam), 15 cytokine/receptor/inflammatory mediator genes (Ccr2, Ccr5, Cc16, Cx3cr1, Cxcl14, Il1a, Tnfrsf14, Tnfsf10, Tnfaip8, Tnfrsfl1a, Tnfrsfl9, Tlr1, Tlr4, Tlr8 and Casp1) and apoptotic gene Casp3 were reduced in liver of E06-scFvLdlr$^{-/-}$ mice (FIG. 5K). As noted above, a variety of inflammatory cytokines/chemokines were decreased in the E06-scFvLdlr$^{-/-}$ mice (FIG. 5E-H). Collectively, these findings suggest that OxPL neutralization decreased the inflammatory content of liver and improved systemic inflammation in AMLN diet-fed mice.

Figures 6A, 6B:
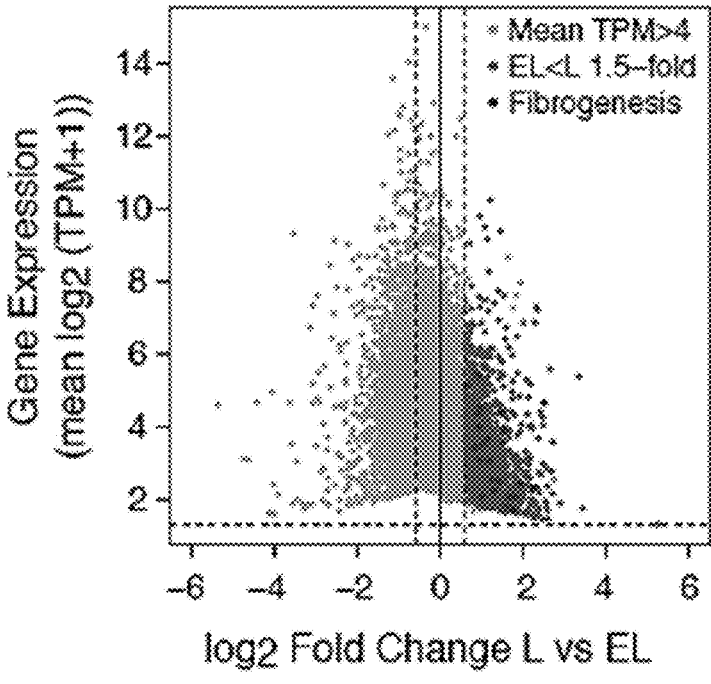

Targeting OxPL prevents hepatic fibrosis. The accumulation of extracellular matrix and collagen in the liver leads to fibrosis and cirrhosis and end stage liver disease, which are the most common fatal hepatic consequences of NASH (Friedman et al., 2018). Prevention of fibrosis is the major goal in therapeutic regimens being developed to treat NASH (Younossi et al., 2018b). Consistent with the marked decrease in hepatic collagen deposition in the E06-scFvLdlr$^{-/-}$ mice (FIG. 2A, E), RNA-seq analysis of livers from mice on the AMLN diet revealed that OxPL neutralization caused a significant decrease in 28 genes related to fibrogenesis, (shown in purple dots in FIG. 6A) in comparison to overall liver mRNA gene changes that decreased (red dots in FIG. 6A) (fold change>1.5, p-adj<0.05). Gene ontology analysis of down-regulated genes of E06-scFvLdlr$^{-/-}$ liver also showed significant functional enrichment for fibrogenic related categories among the top enriched pathways, such as cell migration, extracellular matrix (ECM) organization, collagen formation and PDGF signaling (FIG. 6B). Relative expression values of 15 ECM/receptor (R) genes, 6 growth factor/receptor genes and 7 ECM remodeling gene from liver of both Ldlr$^{-/-}$ and E06-scFvLdlr$^{-/-}$ mice are shown in FIG. 6C.

Figures 6G, 6H, 6I:
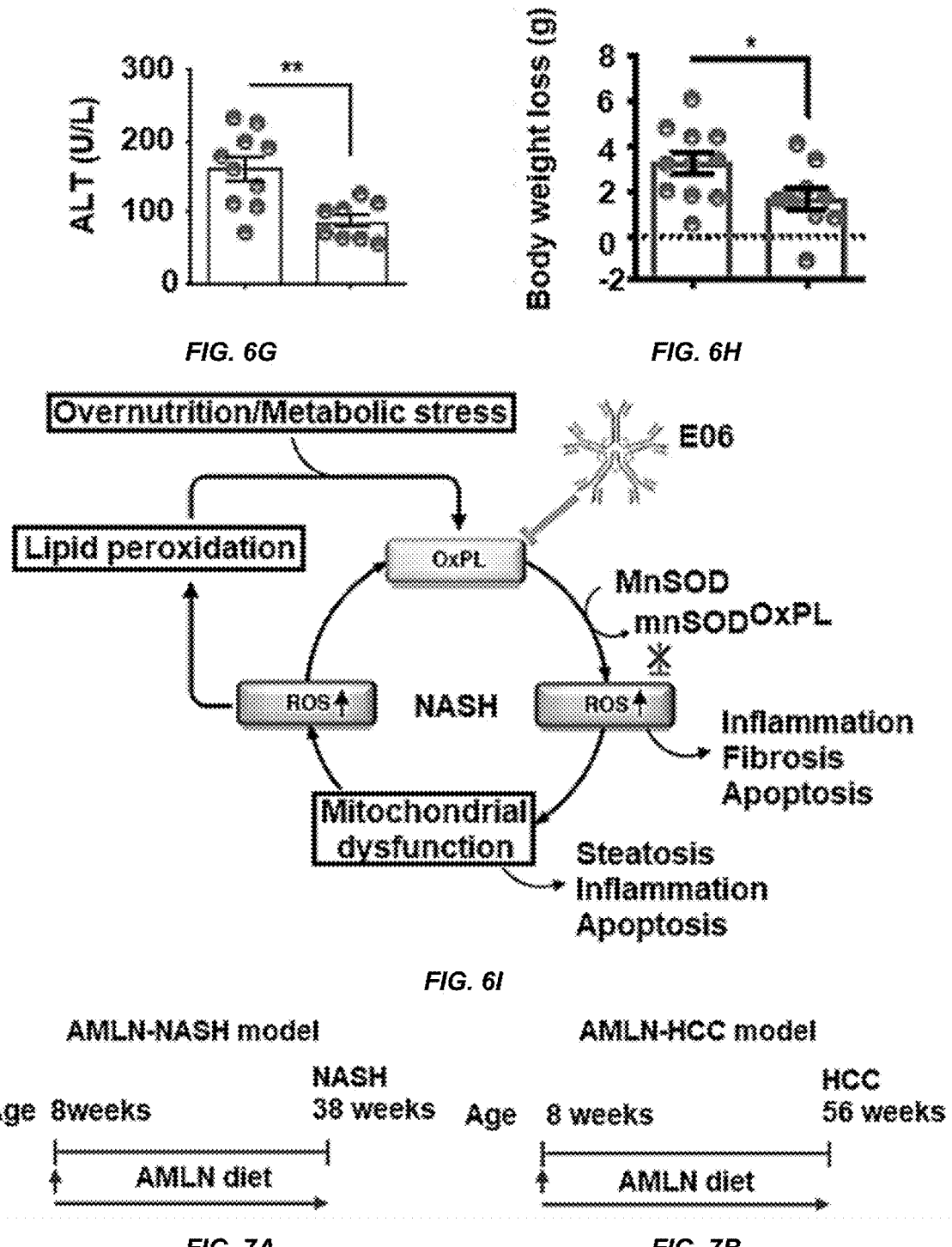

Given that ROS production, an essential contributor to most types of liver fibrosis, was reduced in hepatocytes of E06-scFv expressing mice, experiments were performed to determine whether neutralization of OxPL could directly attenuate fibrogenesis in a liver damage model that was independent of hyperlipidemia or hepatic steatosis, but induces strong free radical formation and lipid peroxidation (Ayala et al., 2014; Muriel, 2017; Shrestha et al., 2016). Liver injury in Ldlr$^{-/-}$ and E06-scFvLdlr$^{-/-}$ mice was induced by intraperitoneal injection of CCl$_4$. Fibrotic septa between parenchymal nodules were attenuated in E06-scFvLdlr$^{-/-}$ mice compared to Ldlr$^{-/-}$ mice, paralleling less OxPL accumulation along the necrotic area (FIG. 6D). Liver hydroxyproline content and expression of fibrogenic genes (Acta2, Col1a1, Col3a1, Tgfb1, Ddr2) were significantly reduced in E06-scFvLdlr$^{-/-}$ mice. The histological features of the respective CCl$_4$ treated cohorts were assessed by a blinded experienced pathologist according to Kleiner Scoring System (Kleiner et al., 2005). Inflammation, hepatocellular injury and fibrosis were all decreased in CCl$_4$-treated E06-scFvLdlr$^{-/-}$ mice compared to Ldlr$^{-/-}$ mice. Moreover, SOD activity in CCl$_4$-treated E06-scFvLdlr$^{-/-}$ mice was higher than that in Ldlr$^{-/-}$ mice. The serum triglycerides and cholesterol were similar in both Ldlr$^{-/-}$ and E06-scFvLdlr$^{-/-}$ mice, e.g. triglyceride of 170 mg/dL and cholesterol levels of 50 mg/dL (FIG. 6E, F). Serum ALT was significantly lower in E06-scFvLdlr$^{-/-}$ mice compared to Ldlr$^{-/-}$ mice (FIG. 6G). Additionally, E06-scFvLdlr$^{-/-}$ mice lost less weight (FIG. 6H), indicating a relative protection from the toxic effects of the CCl$_4$.

To investigate whether OxPL have direct effect on stellate cells, the direct driver of liver fibrosis (Koyama and Brenner, 2017; Tsuchida and Friedman, 2017), human stellate cells were stimulated with OxPAPC. Notably, OxPAPC treatment resulted in a significant increase in fibrogenic gene expression (Acta2, Col1a1, Tgfb1, Timp1). Given that OxPL promote ROS accumulation, hepatic inflammation and damage (FIG. 2, 4, 6), all of which activates stellate cells to induce fibrosis (Koyama and Brenner, 2017; Richter and Kietzmann, 2016; Richter et al., 2015), these data suggest that OxPL contribute to liver fibrosis through both direct and indirect pathways.

There are a variety of mouse models that have been used to study NASH, each of which displays one or more features of human NASH and consequences such as fibrosis, cirrhosis and development of HCC (Friedman et al., 2018; Tsuchida et al., 2018). As presented herein, various NASH models in the Ldlr$^{-/-}$ mouse fed the AMLN diet were used (40 kcal % Fat, 20 kcal % Fructose and 2% Cholesterol), a diet widely used as a preclinical model for identifying pharmacological interventions with greater likelihood of translating to the clinic (Clapper et al., 2013; Friedman et al., 2018). Animals fed the AMLN diet develop both histologic and metabolic features of human NASH (Clapper et al., 2013). By combining the AMLN diet on the Ldlr$^{-/-}$ background, experiments were performed to investigate the role of OxPL in NASH in a metabolic syndrome model.

The disclosure shows that targeting OxPL by E06-scFv restrained multiple aspects of NASH, including steatosis, inflammation, fibrosis, cell death and its progression to HCC. Further, in vivo studies indicated that targeting OxPL improved AMLN diet-induced mitochondrial dysfunction, which reduced hepatic lipid accumulation and attenuated AMLN diet-induced obesity. OxPL induced mitochondrial damage and ROS accumulation, in part through covalent modification of manganese superoxide dismutase (MnSOD/SOD2), inactivating its activity. Neutralization of OxPL decreased hepatic inflammation as indicated by decreased numbers of recruited macrophages, decreased inflammatory gene expression and reduced serum cytokine levels. OxPL was shows to accumulate in livers and plasma of human patients with NASH. Taken together, these findings reveal a causal role of OxPL in the pathogenesis of NASH. Targeting OxPL may be an effective therapeutic strategy to ameliorate NASH.

The disclosure demonstrates that OxPL accumulate in blood and liver of human subjects with NASH and cirrhosis as well as in three diverse models of NASH and liver fibrosis in mice. The accumulation of OxPL that occurred in the AMLN diet fed Ldlr$^{-/-}$ mice occurred in the context of exaggerated hyperlipidemia and steatosis that mimics the clinical setting most often found in human NASH. However, OxPL also accumulated in the serum and liver of CCl$_4$ treated Ldlr$^{-/-}$ mice, a model of liver fibrosis associated with neither hyperlipidemia nor hepatic steatosis, but is thought to be primarily driven by free radical formation. Moreover, in humans, the elevated plasma and liver OxPL content were closely associated with NASH rather than steatosis. In aggregate, these observations suggest that OxPL accumulation is closely associated with progression of NAFL to NASH and that measurement of plasma OxPL may represent a potential non-invasive approach to improve the clinical distinction between NAFL and NASH.

The disclosure further demonstrates that the accumulation of OxPL was causally related to NASH and its complications. Targeting OxPL with the E06-scFv antibody restrained all measured manifestations of NASH in the AMLN-fed murine models, including steatosis, inflammation, fibrosis, hepatocyte cell injury and death, and its progression to HCC.

OxPL are a complex set of oxidized moieties that mediate pathological effects through multiple mechanisms and it is difficult to separate out the relative importance of these myriad effects, many of which are interrelated. The disclosure demonstrates that at least one major mechanistic effect of neutralizing OxPL in the context of the AMLN diet was the promotion of improved mitochondrial function in both liver and adipose tissue. Over nutrition and metabolic stress promoted increases in OxPL, which in turn promoted ROS accumulation and mitochondrial dysfunction. Both elevated ROS and mitochondrial dysfunction contribute to hepatic steatosis, inflammation, apoptosis and fibrosis in NASH. Moreover, in damaged mitochondria, deficiency of electron transport enhances superoxide generation, which in turn would promote lipid peroxidation and enhanced OxPL formation. Therefore, OxPL induced a pathogenic feedforward loop in NASH—as depicted in FIG. 6I. Neutralizing OxPL by E06 abolished the activation of this feedforward loop, resulting in the amelioration of hepatic steatosis, inflammation, apoptosis and fibrosis. Furthermore, neutralization of OxPL also attenuated fibrogenesis in the CCl$_4$ free-radical induced liver fibrosis model, which was devoid of hyperlipidemia or steatosis, and also decreased fibrosis in AMLN-fed C57BL/6 mice, which have low cholesterol levels. These observations suggest that OxPL are one of the long postulated second hit "lipotoxic factors" that promote NASH and its complications, including factors possibly related to HCC formation. Because OxPL are also pathogenically involved in atherogenesis, targeting OxPL as a therapeutic strategy should decrease not only NASH and its complications but atherosclerosis as well.

Defects of mitochondrial function and biogenesis are essential reasons for exacerbated hepatic steatosis and liver damage in NASH pathogenesis (Aharoni-Simon et al., 2011; Finkel, 2012; Nassir and Ibdah, 2014; Rector et al., 2010; Win et al., 2018). In the studies, extensive data in isolated hepatocytes are provided that OxPL induced profound mitochondrial damage and dysfunction, which neutralizing OxPL abrogated. The disclosure further demonstrates that besides improvement of mitochondrial function, neutralizing OxPL also increased mitochondrial biogenesis in livers of AMLN fed mice. An improvement of mitochondrial function and biogenesis in white adipose tissue was shown, leading to enhanced whole-body oxygen consumption rate and increased energy expenditure, which resulted in decreased weight gain and enhanced cold tolerance despite decreased white and brown adipose tissue.

To explore the mechanisms by which OxPL could impair hepatocyte mitochondrial function, the disclosure demonstrates that OxPL could covalently modify MnSOD and impair its activity. The in vivo relevance of this was supported by the demonstration of OxPL-modified MnSOD in NASH liver, but not in normal liver or in AMLN fed E06-scFvLdlr$^{-/-}$ liver. The importance of enhanced mROS generated by OxPL was supported by evidence that the MnSOD mimetic MnTBAP abrogated the OxPL-induced loss of mitochondrial membrane potential and mROS generation (FIG. 4E, F). As noted above, mitochondrial damage would lead to aggravated ROS production in a feedforward loop (FIG. 6I). Therefore, neutralizing OxPL abolished the initiation of this feedforward loop to prevent ROS accumulation and mitochondrial dysfunction. Moreover, OxPL neutralization increased the NAD/NADH ratio because of improved oxidative phosphorylation, and consistent with the role of NAD to be a cofactor that directly activates SIRT1, which shows that neutralizing OxPL increased SIRT1 activity in AMLN diet-fed E06-scFvLdlr$^{-/-}$ mice (FIG. 4P). In turn, since SIRT1 deacetylates and activates PGC1α, the increased NAD/NADH ratio would be predicted to promote mitochondrial biogenesis in E06-scFvLdlr$^{-/-}$ mice. Indeed, gene expression supporting mitochondrial biogenesis was enhanced. Further, PGC1α ChIP-seq data demonstrating enhanced localization to enhancer/promoter regions of key mitochondrial genes. Together with electron microscopy, Mitotracker staining data, and direct measurement of mitochondrial DNA, these data support the pathway outlined leading to an increase of mitochondrial biogenesis in E06-scFvLdlr$^{-/-}$ mouse liver (FIG. 4). Taken together, improvement of mitochondrial function by neutralizing OxPL in the context of the AMLN diet led to increased mitochondrial biogenesis in an NAD/SIRT1/PGC1α-mediated feedforward axis.

Numerous studies have indicated that OxPL induce inflammatory gene expression and pro-inflammatory cytokine production (Huber et al., 2002; Que et al., 2018; Romanoski et al., 2011; Serbulea et al., 2018b; Van Lenten et al., 2001). The disclosure also shows that another major effect of neutralization of OxPL was a decreased proportion of pro-inflammatory Ly6C$^{hi}$ monocytes-derived macrophage in the liver, reduced pro-inflammatory gene expression and reduced levels of circulating inflammatory cytokines, including RANTES, M-CSF, MIP-1b, and TNFα (FIG. 5). These observations indicate that OxPL directly (or indirectly) mediate both systemic and hepatic inflammation during NASH. Moreover, decreased apoptotic cell in livers of E06-scFvLdlr$^{-/-}$ mice, along with decreased serum transaminases in blood, were all consistent with improved NASH. Neutralization of OxPL, which are known as potent inducers of cell injury and apoptosis is partially responsible for this but in addition, a moderately increased proportion of resident Tim4$^+$ KC in E06-scFvLdlr$^{-/-}$ mice was observed, which mediate engulfment of apoptotic cells (FIG. 5). In turn, there was a lower proportion of Tim4$^-$ macrophages (FIG. 5B, D), which are thought to be a macrophage population derived from infiltrating monocytes during inflammation. The decrease in cell death likely further leads to decreased inflammation. Injured and dying cells are known to release microparticles and extracellular vesicles that are enriched in OxPL, (Tsiantoulas et al., 2015; Yang et al., 2018; Zanoni et al., 2017) which in turn can promote ROS production leading to more OxPL production. As a result, OxPL activate a feedforward loop to induce hepatocyte apoptosis and inflammation.

Development of fibrosis leading to cirrhosis and liver failure is a feared complication of NASH and a major target of all therapeutic regimens. The disclosure also demonstrates that another major effect of targeting OxPL was to inhibit fibrosis in the AMLN diet-induced NASH model, in the CCl$_4$-induced liver fibrosis model not associated with hyperlipidemia, and in AMLN-fed C57BL/6 mice with low LDL values. Fibrogenesis is thought to be driven by activated hepatocytes and KC, leading to differentiation of resident hepatic stellate cells (HSC) into myofibroblasts, which in turn overproduce matrix. The disclosure shows that stimulation of a human HSC line by OxPAPC in fact activates the fibrogenic pathway. As noted from the RNA-seq data, there was a marked decrease in the E06-scFv mice of key fibrogenic genes, as well as in growth factors/receptors. In addition, OxPL can likely indirectly induce immune cell-mediated fibrosis by recruitment of leukocytes, especially inflammatory macrophages, which can further induce fibrosis via TGFβ and PDGF and ROS production. OxPL accumulate within alveolar macrophages in bleomycin induced lung fibrosis, which then display enhanced production of TGFβ. Direct instillation of OxPAPC into the mouse lung induced foam cell formation. In addition to direct activation of HSC, OxPL activation of KC or hepatocytes leads to enhanced TGFβ production, which also initiates HSC activation that promote fibrosis. OxPL might thus contribute to the pulmonary toxicity of bleomycin that promotes fibrosis. Future studies will be needed to test these hypotheses. Understanding the cellular and molecular mechanisms by which OxPL promote fibrosis may have widespread therapeutic implications aside from liver fibrosis, for example, in diseases such as radiation and bleomycin induced lung fibrosis.

The cellular and molecular mechanisms by which OxPL mediate the pathological effects demonstrated here are complex but have been shown to induce cellular responses in immune cells including activation of CD36, TLR2/1 and TLR2/6, TLR4, CD14 and combinations of these receptors (Bieghs et al., 2012; Binder et al., 2016; Imai et al., 2008; Kadl et al., 2011; Lee et al., 2012; Miller et al., 2011; Podrez et al., 2002; Seimon et al., 2010; Wakusawa et al., 1997). The disclosure shows another mechanism by which reactive OxPL can alter normal cellular metabolism in hepatocytes-namely by the direct covalent modification of proteins. The distinct cellular pathways mediating individual effects will need to be studied by combinations of in vitro and in vivo studies in relevant cell populations of E06-scFv mice. These effects may also differ with different OxPL species, as for example, Leitinger and colleagues have shown that fragmented OxPL are responsible for reprogramming of macrophage metabolism, whereas full-length OxPL were more responsible for proinflammatory gene expression (Serbulea et al., 2018a; Serbulea et al., 2018b). Further studies will also be needed to address the etiology of the increased OxPL that accumulate in both liver and blood of both the murine models and the human subjects with NASH. Enhanced inflammation and lipid peroxidation occur with the marked hyperlipidemia associated with the AMLN diet (Dhibi et al., 2011), and this no doubt leads to enhanced non-enzymatic lipid peroxidation and OxPL generation and accumulation. On the other hand, CCl$_4$ is known to initiate free radical formation and also led to OxPL accumulation even in the absence of steatosis or hyperlipidemia. Of further relevance, it has been shown that activation of TLR4 on macrophages in culture leads to secretion of OxPL into the media (Popat et al., 2017) and similarly, TLR2 activation also leads to macrophage release of OxPL. In turn, as shown in the studies, OxPL stimulated both total and mROS production and accumulation in hepatocytes, which would promote lipid peroxidation and further OxPL generation. Thus, it is likely that there are a series of interacting "vicious cycles" that feedforward to lead to sustained enhanced OxPL accumulation, which in turn promote NASH and its complications (FIG. 6I).

The data demonstrate that OxPL is increased in plasma and livers of humans with NASH and that targeting OxPL in relevant mouse models restrains NASH and its complications of steatosis, inflammation, hepatocyte injury and cell death, fibrosis and possibly HCC formation. The studies to date have used transgenic mice that constitutively express the E06-scFv antibody at a concentration of 20-30 ug/ml or less, which seems sufficient to prevent many of the consequences of NASH observed in these varying models. Importantly, translational studies in which an appropriate IgG version of E06 is infused into mice to show prevention of NASH, as well as regression of NASH in models with existing disease, will be required to show the importance of these studies for therapeutic purposes. The E06 antibody used in these studies is an innate natural antibody present in mice. Similar natural antibodies that target OxPL exist in humans, suggesting the feasibility of translating this approach to humans.

A number of embodiments have been described herein. Nevertheless, it will be understood that various modifications may be made without departing from the spirit and scope of this disclosure. Accordingly, other embodiments are within the scope of the following claims.

---

What is claimed is:

1. A method for determining and or distinguishing a disease or disorder associated with oxidized phospholipids (OxPL) in a subject, the method comprising:

a) obtaining a sample from the subject;

b) spiking the sample with labeled phosphocholine (labeled-PC) to obtain a spiked sample;

c) contacting the spiked sample with a substrate comprising known quantity of an antibody, antibody fragment or non-immunoglobulin binding domains that bind to OxPL under conditions such that OxPL and labeled-PC bind to the known quantity of antibody, antibody fragment or non-immunoglobulin binding domains;

d) washing the substrate to remove unbound OxPL and labeled-PC;

e) contacting bound labeled-PC with an agent that measures the amount of labeled-PC;

f) comparing the levels of labeled-PC to a standard curve; and g) identifying an amount of total OxPL in the sample based upon the standard curve, wherein the amount is indicative of a disease or disorder associated with OxPL.

2. The method of claim 1, wherein the sample is blood, plasma or serum.

3. The method of claim 1, wherein a label of the labeled-PC is selected from the group consisting of an antigenic epitope, a protein, a peptide, a fluorescent molecule, a luminescent molecule, an enzyme, and a radiolabel.

4. The method of claim 3, wherein the labeled-PC comprises PC linked to an antigenic epitope.

5. The method of claim 4, wherein the antigenic epitope is KeyHole Limpet Hemocyanin (KLH).

6. The method of claim 3, wherein the labeled-PC comprises a PC linked to biotin or streptavidin via a peptide linker.

7. The method of claim 4, wherein the labeled-PC is detected by using an antibody that binds to the antigenic epitope.

8. The method of claim 7, wherein the antibody binds to KLH.

9. The method of claim 6, wherein the labeled-PC is detected by biotin-streptavidin interaction.

10. The method of claim 1, further comprising preparing a standard curve of labeled-PC using a substrate and various known quantities of labeled-PC.

11. The method of claim 1, wherein the antibody, antibody fragment or non-immunoglobulin binding domains that bind to OxPL is an E06 antibody or a fragment thereof.

12. The method of claim 1, wherein the disease or disorder associated with OxPL is liver disease.

13. The method of claim 7, wherein the liver disease is non-alcoholic fatty liver disease (NALFD) and/or non-alcoholic steatohepatitis (NASH).

14. A method for determining and distinguishing a liver disease associated with OxPL in a subject, the method comprising:
    a) obtaining a sample from the subject;
    b) spiking the sample with labeled phosphocholine (labeled-PC) to obtain a spiked sample;
    c) contacting the spiked sample with a substrate comprising a known quantity of antibody, antibody fragment or non-immunoglobulin binding domains that bind to OxPL under conditions such that OxPL and labeled-PC bind to the known quantity of antibody, antibody fragment or non-immunoglobulin binding domains;
    d) washing the substrate to remove unbound OxPL and labeled-PC;
    e) contacting bound labeled-PC with an agent that measures the amount of labeled-PC;
    f) comparing the levels of labeled-PC to a standard curve; and
    g) identifying an amount of total OxPL in the sample based upon the standard curve, wherein the amount is indicative of whether the subject has liver disease.

15. The method of claim 14, wherein the sample is blood, plasma or serum.

16. The method of claim 14, wherein a label of the labeled-PC is selected from the group consisting of an antigenic epitope, a protein, a peptide, a fluorescent molecule, a luminescent molecule, an enzyme, and a radiolabel.

17. The method of claim 16, wherein the labeled-PC comprises PC linked to an antigenic epitope.

18. The method of claim 17, wherein the antigenic epitope is KeyHole Limpet Hemocyanin (KLH).

19. The method of claim 16, wherein the labeled-PC comprises a PC linked to biotin or streptavidin via a peptide linker.

20. The method of claim 17, wherein the labeled-PC is detected by using an antibody that binds to the antigenic epitope.

21. The method of claim 7, wherein the antibody binds to KLH.

22. The method of claim 6, wherein the labeled-PC is detected by biotin-streptavidin interaction.

23. The method of claim 14, further comprising preparing a standard curve of labeled-PC using a substrate and various known quantities of labeled-PC.

24. The method of claim 14, wherein the antibody, antibody fragment or non-immunoglobulin binding domains that bind to OxPL is an E06 antibody or a fragment thereof.

25. The method of claim 14, wherein the liver disease is NALFD and/or NASH.

26. A method of monitoring an obesity/weight loss treatment in a subject, the method comprising:
    a) obtaining a plurality of samples from the subject prior to and during treatment;
    b) spiking the plurality of samples with labeled phosphocholine (labeled-PC) to obtain a spiked sample;
    c) contacting the spiked sample with a substrate comprising known quantity of an antibody, antibody fragment or non-immunoglobulin binding domains that bind to OxPL under conditions such that OxPL and labeled-PC bind to the known quantity of antibody, antibody fragment or non-immunoglobulin binding domains;
    d) washing the substrate to remove unbound OxPL and labeled-PC;
    e) contacting bound labeled-PC with an agent that measures the amount of labeled-PC;
    f) comparing the levels of labeled-PC to a standard curve; and
    g) identifying an amount of total OxPL in the sample based upon the standard curve, wherein the amount is indicative of a change in total OxPL in the subject during treatment.

* * * * *